(12) United States Patent
Osumi et al.

(10) Patent No.: US 7,148,397 B2
(45) Date of Patent: Dec. 12, 2006

(54) SOLANUM BULBOCASTANUM LATE BLIGHT RESISTANCE GENE AND USE THEREOF

(75) Inventors: Teruko Osumi, Blacksburg, VA (US); William R. Belknap, Albany, CA (US); David R. Rockhold, El Cerrito, CA (US); Mary M. Maccree, Encinitas, CA (US); Kent F. McCue, El Cerrito, CA (US); Kenneth L. Deahl, Silver Spring, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 183 days.

(21) Appl. No.: 10/647,268

(22) Filed: Aug. 20, 2003

(65) Prior Publication Data

US 2004/0237137 A1 Nov. 25, 2004

Related U.S. Application Data

(60) Provisional application No. 60/407,100, filed on Aug. 29, 2002.

(51) Int. Cl.
*C12N 15/09* (2006.01)
*C12N 15/29* (2006.01)
*C12N 15/82* (2006.01)
*A01H 5/00* (2006.01)

(52) U.S. Cl. .................... 800/279; 800/278; 800/298; 800/317; 435/69.1; 435/468; 536/23.6

(58) Field of Classification Search ............... 800/278, 800/279, 298, 317; 435/320.1, 468, 69.1; 536/23.26, 23.6
See application file for complete search history.

(56) References Cited

U.S. PATENT DOCUMENTS 6,100,449 A * 8/2000 Fluhr et al. ................. 800/279

OTHER PUBLICATIONS

Parker et al. The Plant Cell (1996), vol. 8, pp. 2033-2046.*
Naess et al. Theor Appl. Genet (2000) 101:697-704.*
Van der Vossen et al (2003) 36:867-882.*
Williams et al. Nucleic Acids Research, vol. 18, No. 22 p. 6531-6535.*
Song et al. Genome 43: 199-204 (2000).*
Helgeson et al. Theor Appl Genet (1998) 96:738-742.*
Thieme et al. Euphytica (1997) 97:189-200.*
Bradeen, J.M. et al., "Concomitant reiterative BAC walking and fine genetic mapping enable physical map development for the broad-spectrum late blight resistance region, *RB*," *Mol. Gen. Genomics* (2003) 269:603-611.
Helgeson, J.P. et al., "Somatic hybrids between *Solanum bulbocastanum* and potato: a new source of resistance to late blight," *Theor Appl Genet* (1998) 96:738-742.
Naess, S.K. et al., "Resistance to late blight in *Solanum bulbocastanum* is mapped to chromosome 8," *Theor Appl Genet* (2000) 101:697-704.
Naess, S.K. et al., "Analysis of the introgression of *Solanum bulbocastanum* DNA into potato breeding lines," *Mol Genet Genomics* (2001) 265:694-704.
Song, J., F. Dong, and J. Jiang, "Construction of a bacterial artificial chromosome (BAC) library for potato molecular cytogenetics research," *Genome* (2000) 43:199-204.
Song, J. et al., "Gene *RB* cloned from *Solanum bulbocastanum* confers broad spectrum resistance to potato late blight," *PNAS* (2003) 100(16):9128-9133.
Database Genbank, NCBI, Accession No. AY303170, Song et al. (2003).
Database Genbank, NCBI, Accession No. AY303171, Song et al. (2003).
Database Genbank, NCBI, Accession No. AY336128, Song et al. (2003).

* cited by examiner

*Primary Examiner*—Medina A. Ibrahim
(74) *Attorney, Agent, or Firm*—Margaret A. Connor; Curtis P. Ribando; John D. Fado

(57) ABSTRACT

A *Solanum bulbocastanum* gene has been cloned from a late blight-resistance locus and its sequence provided, together with the sequence of the encoded protein. DNA encoding the resistance protein has been introduced into potato plants and confers resistance to *Phytophthora infestans*, the causal agent of late blight. The resistance protein is in the class of Nucleotide Binding Site-Leucine-Rich Repeat Proteins (NBS-LRRP), and the gene in *S. bulbocastanum* is flanked by related NBS-LRRP gene sequences.

14 Claims, 17 Drawing Sheets

Sbul1 Genomic Transgene
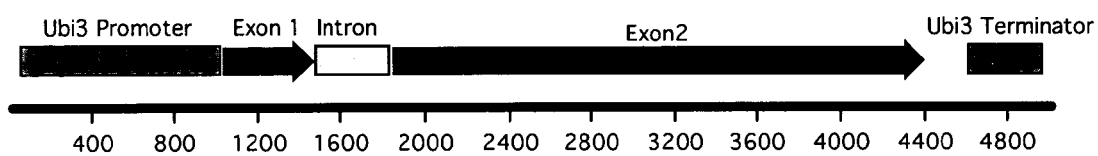
Sbul1 cDNA Transgene
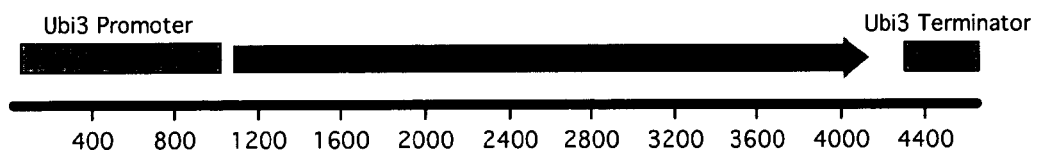
FIG. 4

Alignment of *Sbu1* (SEQ ID NO:4) and *Sbu2* (SEQ ID NO:6)
deduced Amino Acid sequences

```
Sbu1:   MAEAFLQVLLDNLTCFIQGELGLILGFKDEFEKLQSTFTTIQAVLEDAQKKQLKDKAIEN
Sbu2:   MAEAFLQVLLDNLTCFIQGEVGLILGFKDEFEKLQSTFTTIQAVLEDAQKKQLKDKAIEN

Sbu1:   WLQKLNAAAYEADDILDECKTEAPIRQKKNKYGCYHPNVITFRHKIGKRMKKIMEKLDVI
Sbu2:   WLQKLNAAVYEADDILDECKTEAPIRQKKNKYGCYHPNVIAFRHKIGKRMKKIMEKLDVI

Sbu1:   AAERIKFHLDERTIERQVATRQTG---Intron-------PVLNEPQVYGRDKEKDEIVK
Sbu2:   AAERIKFHLAERTTERQVATRQTG---Intron-------PVLNEPQVYGRDKEKDEIVK Sbu1:   ILINNVSNAQTLPVLPILGMGGLGKTTLAQMVFNDQRVIEHFHPKIWICVSEDFNEKRLI
Sbu2:   ILINIVSDAQTLSVLPILGMGGLGKTTLAQMVFNDQRVIEHFLPKIWICVSEDFNEKRLI Sbu1:   KEIVESIEEKSLGGMDLAPLQKKLRDLLNGKKYLLVLDDVWNEDQDKWAKLRQVLKVGA
Sbu2:   KEIVESIEEKSLGDMDLAPLQKKLQDLLNGKKYLLVLDDIWNEDQDKWAKLREVLKVGA Sbu1:   SGASVLTTTRLEKVGSIMGTLQPYELSNLSQEDCWLLFMQRAFGHQEEINLNLVAIGKEI
Sbu2:   SGASILTTTRLEKVGSIMQTLQPYELSNLCQEDCWLLFMQRAFGHQEEINHNLVAIGKEI Sbu1:   VKKCGGVPLAAKTLGGILRFKREERQWEHVRDSEIWKLPQEESSILPALRLSYHHLPLDL
Sbu2:   VKKCGGVPLAAKTLGGILRFKRQERQWEHVRDSEIWKLPQEESSILPALKLSYHHLPLDL Sbu1:   RQCFTYCAVFPKDTEMEKGNLISLWMAHGFILSKGNLELENVGNEVWNELYLRSFFQEIE
Sbu2:   RQCFSYCAVFPKDTKMEKENLISLWMAHGFLLSKGNLELEDVGNEVWNELYLRSFFQEIE Sbu1:   VKSGQTYFKMHDLIHDLATSLFSASTSSSNIREIIVENYIHMMSIGFTKVVSSYSLSHL
Sbu2:   VTYGKTYFKMHDLIHDLATSLFSASASSNNIREINVKGYPHMMSIGFAKVVSFYSRSHF Sbu1:   QKFVSLRVLNLSDIKLKQLPSSIGDLVHLRYLNLSGNTSIRSLPNQLCKLQNLQTLDLHGC
Sbu2:   QKFVSLRVLNLSNLELKQLPSSIGDLVHLRYLNLSDNNRIRSLPKQLCKLQNLQTLDLRCC Sbu1:   HSLCCLPKETSKLGSLRNLLLDGCYGLTCMPPRIGSLTCLKTLSRFVVGIQKKSCQLGELR
Sbu2:   YRLSCLPKETSKLGSLRNLLLDRCHGLTCMPPRIGSLTCLKTLDRFAMG-REKSPQIGELR Sbu1:   NLNLYGSIEITHLERVKNDMDAKEANLSAKENLHSLSMKWDDDERPRIYESEKVEVLE
Sbu2:   NLNLYGSISITHLERVKNDMDAKEANLSSKENLHSLSMIWDEDERPHRYESEDVEVLE Sbu1:   ALKPHSNLTCLTIRGFRGIRLPDWMNHSVLKNVVSIEIISCKNCSCLPPFGELPCLKSLEL
Sbu2:   ALKPHSNLTCLTIIGFRGIRLPDWMNHSVLKNVVSLEISDCKNCSCLPPFGELPCLNSLQL Sbu1:   WRGSAEVEYVDSGFPTRRRFPSLRKLNIREFDNLKGLLKKEGEEQCPVLEEIEIKC
Sbu2:   WSGSAEVEYIDSGFPTRRRFPSLRKLIIGEFDNLKGLVKKEGEEQFPVLEEMEINW
```

FIG. 6A

```
Sbu11:    CPMFVIPTLSSVKKLVVSGDKSDAIGFSSISNLMALTSLQIRYNKEDASLPEEMFKSLANL
Sbu12:    CPMFVIPTLSSVNKLVVSGEESDAIGFSSISNLRALTSLNISYNSEATSLPEEMFKSLANL

Sbu11:    KYLNISFYFNLKELPTSLASLNALKHLEIHSCYALESLPEEGVKGLISLTQLSITYCEMLQ
Sbu12:    KYLNIYYFKNLKELPTNLASLNALKNLEIESCYALESLPEEGVKGLTSLTQLSITYCTMLQ

Sbu11:    CLPEGLQHLTALTNLSVEFCPTLAKRCEKGIGEDWYKIAHIPRVFIY*
Sbu12:    CLPEGLQHLTALTNLSVRDCPTLAKRCEKGIGEDWYKIAHIPDVFIR*
```

FIG. 6B

Alignment of *Sbu1* (SEQ ID NO:3) and *Sbu2* (SEQ ID NO:5)
gene sequences

```
Sbu1    CCAACATCTTACTTCATTTCAAAAAATATAGATTCATTGCGTACTCACAATACTCTATGGCTGAAGCTTTCCTTCAAGTT
                                                            MetAlaGluAlaPheLeuGlnVal>
                                                            _____EXON1_____>

Sbu2    CCAACATCTTACTTCATTTCAAAAAATATAGATTCATTGCtTcCTCACAATACTCTATGGCTGAAGCTTTCCTTCAAGTT>
        ||||||||||||||||||||||||||||||||||||||||*|*|||||||||||||||||||||||||||||||||||||
Sbu1    CCAACATCTTACTTCATTTCAAAAAATATAGATTCATTGCGTACTCACAATACTCTATGGCTGAAGCTTTCCTTCAAGTT

Sbu1    CTGTTAGACAATCTGACTTGTTTCATCCAAGGGGAACTTGGATTGATTCTTGGTTTTAAGGATGAGTTCGAAAAGCTTCA
        LeuLeuAspAsnLeuThrCysPheIleGlnGlyGluLeuGlyLeuIleLeuGlyPheLysAspGluPheGluLysLeuGln>
        _____EXON1_____>

Sbu2    CTGTTAGACAATCTGACTTGTTTCATCCAAGGGGAAgTTGGATTGATTCTTGGTTTTAAGGATGAGTTCGAAAAGCTTCA>
        |||||||||||||||||||||||||||||||||||||*|||||||||||||||||||||||||||||||||||||||||
Sbu1    CTGTTAGACAATCTGACTTGTTTCATCCAAGGGGAACTTGGATTGATTCTTGGTTTTAAGGATGAGTTCGAAAAGCTTCA

Sbu1    AAGCACGTTTACTACAATCCAAGCTGTGCTAGAAGATGCTCAGAAGAAGCAATTGAAGGACAAGGCAATAGAAAATTGGT
           SerThrPheThrThrIleGlnAlaValLeuGluAspAlaGlnLysLysGlnLeuLysAspLysAlaIleGluAsnTrp>
        _____EXON1_____>

Sbu2    AAGCACaTTTACTACAATCCAAGCTGTGCTAGAAGATGCTCAGAAGAAGCAATTGAAGGACAAGGCAATAGAAAATTGGT>
        ||||||*|||||||||||||||||||||||||||||||||||||||||||||||||||||||||||||||||||||||
Sbu1    AAGCACGTTTACTACAATCCAAGCTGTGCTAGAAGATGCTCAGAAGAAGCAATTGAAGGACAAGGCAATAGAAAATTGGT

Sbu1    TGCAGAAACTCAATGCTGCTGCATATGAGGCTGATGACATCTTGGACGAATGTAAAACTGAGGCACCAATTAGACAGAAG
        LeuGlnLysLeuAsnAlaAlaAlaTyrGluAlaAspAspIleLeuAspGluCysLysThrGluAlaProIleArgGlnLys>
        _____EXON1_____>

Sbu2    TGCAGAAACTCAATGCTGCTGtATATGAaGCTGAcGACATCTTGGACGAATGTAAAACTGAGGCACCAATTAGACAGAAG>
        |||||||||||||||||||||*||||||*|||||*|||||||||||||||||||||||||||||||||||||||||||
Sbu1    TGCAGAAACTCAATGCTGCTGCATATGAGGCTGATGACATCTTGGACGAATGTAAAACTGAGGCACCAATTAGACAGAAG

Sbu1    AAGAACAAATATGGGTGTTATCATCCAAACGTTATCACTTTTCGTCACAAGATTGGGAAAAGGATGAAAAAGATTATGGA
        LysAsnLysTyrGlyCysTyrHisProAsnValIleThrPheArgHisLysIleGlyLysArgMetLysLysIleMetGlu>
        _____EXON1_____>

Sbu2    AAGAACAAATATGGGTGTTATCATCCAAACGTTATCgCTTTcCGTCACAAGATTGGGAAAAGGATGAAAAAGATTATGGA>
        ||||||||||||||||||||||||||||||||||||*||||*||||||||||||||||||||||||||||||||||||
Sbu1    AAGAACAAATATGGGTGTTATCATCCAAACGTTATCACTTTTCGTCACAAGATTGGGAAAAGGATGAAAAAGATTATGGA
```

FIG. 7A

```
Sbu11     GAAACTAGATGTAATTGCAGCGGAACGAATTAAGTTTCATTTGGATGAAAGGACTATAGAGAGACAAGTTGCTACACGCC
          LysLeuAspValIleAlaAlaGluArgIleLysPheHisLeuAspGluArgThrIleGluArgGlnValAlaThrArg>
          ─────────────────────────────────────EXON1─────────────────────────────────────>

Sbu12     GAAACTAGATGTAATTGCAGCGGAACGAATTAAGTTTCATTTGGcTGAAAGGACTAcAGAGAGACAAGTTGCTACACGCC>
          |||||||||||||||||||||||||||||||||||||||||||*|||||||||||*||||||||||||||||||||||||
Sbu11     GAAACTAGATGTAATTGCAGCGGAACGAATTAAGTTTCATTTGGATGAAAGGACTATAGAGAGACAAGTTGCTACACGCC

Sbu11     AAACAGGTGCTCATCTTAGATATTTTTCTGAAAAAACAGCTTTATATCATCAAATTCATGTGTGTTTTGGGAATTCGTCT
          GlnThr>
          ────>
                                  ─────────────────────────INTRON──────────────────────────>

Sbu12     AAACAGGTGCTCATCTTAGATATTTTTCTaAAAAAACAGCTTTATATCATgAAATTCATGTGTGTTTgGGattTTtt>
          ||||||||||||||||||||||||||||*|||||||||||||||||||*|||||||||||||||||*||***||**
Sbu11     AAACAGGTGCTCATCTTAGATATTTTTCTGAAAAAACAGCTTTATATCATCAAATTCATGTGTGTTTTGGGAATTCG Sbu11     AATCTAAATGTTCGTCTCAAGTCTAAGTAGATAAGTGGATCCAGCTTTGGATTTATTAATCTATTAGCTAAATCTGTTTA
          ──────────────────────────────────────INTRON──────────────────────────────────>

Sbu12     AatctAAatgTtGTCTCAAGTCTAAGTAGATAAGTGGATCCAGaTTTGGATaTATTAATaTATTAtCTAAATtTGTTTc>
          |****||***|*|||||||||||||||||||||||||||||*|||||||*||||||*|||||*|||||*|||||*
Sbu11     ATCTAAATGTTCGTCTCAAGTCTAAGTAGATAAGTGGATCCAGCTTTGGATTTATTAATCTATTAGCTAAATCTGTTTA Sbu11     GTGAAGTTTTTAACATATATAACCTCAGATAAATCCATAGCTTACTCATAGGATTAGGATAGGCCCCCAAGTCTAAATGA
                         ─────────────────────────INTRON──────────────────────────────────>

Sbu12     GTGAAaTTTTTAACAgATAaAgCCT>
          |||||*|||||||||*|||*|*|||
Sbu11     GTGAAGTTTTTAACATATATAACCT

Sbu11     CAGGATAAAGCCAGAGTTGTTTTAGCTCTTATAAATTAACAATGATAATAATGTGAATTCAAAAAAGTGCATTTTTTTAA
                                  ─────────────────INTRON──────────────────────────────────>

Sbu12     acaGATAAAGCCtGAGTTGTTTTAGacaTTATAAATTAACAATGATAATAATGTGAATTCAAAAAAGTGCATTaTgTctg>
          ***||||||||*|||||||||||||***||||||||||||||||||||||||||||||||||||||||||||*|*|***
Sbu11     CAGGATAAAGCCAGAGTTGTTTTAGCTCTTATAAATTAACAATGATAATAATGTGAATTCAAAAAAGTGCATTTTTTTAA Sbu11     TTTGAAATATTTCTGCTGCTTCTCAAGCTTATCATTGTCTTTTTACTGTGCAAAATTCTACTTTGTATTTTGCTGACTC
                                  ─────────────────INTRON──────────────────────────────────>

Sbu12     agTGcAtTATgTCTGCTGCTTCTCAAGCTTATCATTGTCTcTTTAtTGTGCAAAATTCTtCTTcGTtTTTTGCTGACTC>
          **|*|*|||*|||||||||||||||||||||||||||||*||||*|||||||||||||*||*||*|||||||||||||
Sbu11     TTTGAAATATTTCTGCTGCTTCTCAAGCTTATCATTGTCTTTTTACTGTGCAAAATTCTACTTTGTATTTTGCTGACTC
```

FIG. 7B

```
Sbu11    CTACCGAGCTTGGGCCAGGTTTTGTTTTGAATGAACCACAAGTTTATGGAAGAGACAAAGAAAAGGACGAGATAGTGAAA
               GlyPheValLeuAsnGluProGlnValTyrGlyArgAspLysGluLysAspGluIleValLys>
                                              EXON2                                    >
         ____INTRON_____>

Sbu12    CTACtGAGCTTGGaCCAGGTTTTGTTTTaAATGAACCACAAGTTTATGGAAGAGACAAAGAAAAGGAtGAGATAGTGAAA>
         ||||*||||||||*|||||||||||||*||||||||||||||||||||||||||||||||||||*|||||||||||||
Sbu11    CTACCGAGCTTGGGCCAGGTTTTGTTTTGAATGAACCACAAGTTTATGGAAGAGACAAAGAAAAGGACGAGATAGTGAAA

Sbu11    ATCCTGATAAACAATGTTAGCAATGCCCAAACACTTCCAGTCCTCCCAATACTTGGTATGGGGGGACTAGGAAAGACGAC
           IleLeuIleAsnAsnValSerAsnAlaGlnThrLeuProValLeuProIleLeuGlyMetGlyGlyLeuGlyLysThrThr>
                                              EXON2                                    >

Sbu12    ATCCTGATAAACAtTGTTAGCgATGCCCAAACACTTtCAGTCCTCCCAATACTTGGTATGGGGGGAtTAGGAAAGACGAC>
         |||||||||||||*|||||||*|||||||||||||*||||||||||||||||||||||||||||||*|||||||||||
Sbu11    ATCCTGATAAACAATGTTAGCAATGCCCAAACACTTCCAGTCCTCCCAATACTTGGTATGGGGGGACTAGGAAAGACGAC

Sbu11    TCTTGCCCAAATGGTCTTCAATGATCAGAGAGTAATTGAGCATTTCCATCCCAAAATATGGATTTGTGTCTCGGAAGATT
           LeuAlaGlnMetValPheAsnAspGlnArgValIleGluHisPheHisProLysIleTrpIleCysValSerGluAsp>
                                              EXON2                                    >

Sbu12    aCTTGCCCAAATGGTCTTCAATGATCAGAGAGTAATTGAGCATTTCCtTCCCAAAATATGGATTTGTGTCTCGGAAGATT>
         *|||||||||||||||||||||||||||||||||||||||||||||*||||||||||||||||||||||||||||||||
Sbu11    TCTTGCCCAAATGGTCTTCAATGATCAGAGAGTAATTGAGCATTTCCATCCCAAAATATGGATTTGTGTCTCGGAAGATT

Sbu11    TTAATGAGAAGAGGTTGATAAAGGAAATTGTAGAATCTATTGAAGAAAAGTCACTTGGTGGCATGGACTTGGCTCCACTT
           PheAsnGluLysArgLeuIleLysGluIleValGluSerIleGluGluLysSerLeuGlyGlyMetAspLeuAlaProLeu>
                                              EXON2                                    >

Sbu12    TTAATGAGAAGAGGTTGATAAAGGAAATTGTAGAATCTATTGAAGAAAAGTCACTTGGTGaCATGGACTTGGCTCCACTT>
         |||||||||||||||||||||||||||||||||||||||||||||||||||||||||||*|||||||||||||||||||
Sbu11    TTAATGAGAAGAGGTTGATAAAGGAAATTGTAGAATCTATTGAAGAAAAGTCACTTGGTGGCATGGACTTGGCTCCACTT

Sbu11    CAAAAGAAGCTTCGGGACTTGCTGAATGGAAAAAAATATTTGCTCGTCTTAGATGATGTTTGGAATGAAGATCAAGATAA
           GlnLysLysLeuArgAspLeuLeuAsnGlyLysLysTyrLeuLeuValLeuAspAspValTrpAsnGluAspGlnAspLys>
                                              EXON2                                    >

Sbu12    CAAAAGAAGCTTCaGGACTTGCTGAATGGAAAAAAATATTTGCTtGTCTTAGATGAtATTTGGAATGAAGATCAAGATAA>
         |||||||||||||*|||||||||||||||||||||||||||||*|||||||||||*|||*|||||||||||||||||||
Sbu11    CAAAAGAAGCTTCGGGACTTGCTGAATGGAAAAAAATATTTGCTCGTCTTAGATGATGTTTGGAATGAAGATCAAGATAA
```

FIG. 7C

```
Sbu11    GTGGGCTAAGTTAAGACAAGTCTTGAAGGTTGGAGCAAGTGGCGCTTCTGTTCTAACCACTACTCGTCTTGAAAAGGTTG
         TrpAlaLysLeuArgGlnValLeuLysValGlyAlaSerGlyAlaSerValLeuThrThrThrArgLeuGluLysVal>
         _____EXON2_____>

Sbu12    GTGGGCTAAGTTAcGAgAAGTgTTGAAGGTTGGAGCAAGTGGtGCTTCTaTcCTAACCACTACTCGTCTTGAAAAGGTTG>
         ||||||||||||*||*||||*||||||||||||||||||||*||||||*|*||||||||||||||||||||||||||||
Sbu11    GTGGGCTAAGTTAAGACAAGTCTTGAAGGTTGGAGCAAGTGGCGCTTCTGTTCTAACCACTACTCGTCTTGAAAAGGTTG

Sbu11    GATCAATTATGGGAACATTGCAACCATATGAATTGTCAAATTTGTCTCAAGAAGATTGTTGGTTGTTGTTCATGCAACGT
         GlySerIleMetGlyThrLeuGlnProTyrGluLeuSerAsnLeuSerGlnGluAspCysTrpLeuLeuPheMetGlnArg>
         _____EXON2_____>

Sbu12    GATCAATTATGcaAACtTTGCAACCATATGAATTGTCAAAcTTGTgTCAAGAAGATTGcTGGTTGTTGTTCATGCAACGT>
         ||||||||||||**|||*|||||||||||||||||||||*||||*|||||||||||||*||||||||||||||||||||
Sbu11    GATCAATTATGGGAACATTGCAACCATATGAATTGTCAAATTTGTCTCAAGAAGATTGTTGGTTGTTGTTCATGCAACGT

Sbu11    GCATTTGGGCACCAAGAAGAAATAAATCTTAATCTTGTGGCTATCGGAAAGGAGATTGTGAAAAAATGTGGTGGTGTGCC
         AlaPheGlyHisGlnGluGluIleAsnLeuAsnLeuValAlaIleGlyLysGluIleValLysLysCysGlyGlyValPro>
         _____EXON2_____>

Sbu12    GCATTTGGGCACCAAGAAGAAATAAATCaTAATCTTGTGGCTATCGGAAAGGAGATaGTGAAAAAATGTGGTGGTGTGCC>
         |||||||||||||||||||||||||||*||||||||||||||||||||||||||*||||||||||||||||||||||||
Sbu11    GCATTTGGGCACCAAGAAGAAATAAATCTTAATCTTGTGGCTATCGGAAAGGAGATTGTGAAAAAATGTGGTGGTGTGCC

Sbu11    TCTAGCAGCTAAAACTCTTGGAGGTATTTTGCGCTTTAAGAGAGAAGAAAGACAGTGGGAACATGTGAGAGATAGTGAGA
         LeuAlaAlaLysThrLeuGlyGlyIleLeuArgPheLysArgGluGluArgGlnTrpGluHisValArgAspSerGlu>
         _____EXON2_____>

Sbu12    TCTAGCAGCTAAAACTCTTGGAGGTATTTTGCGaTTCAAGAGACAAGAAAGACAGTGGGAACATGTGAGAGATAGTGAGA>
         |||||||||||||||||||||||||||||||*||*||||||*||||||||||||||||||||||||||||||||||||
Sbu11    TCTAGCAGCTAAAACTCTTGGAGGTATTTTGCGCTTTAAGAGAGAAGAAAGACAGTGGGAACATGTGAGAGATAGTGAGA

Sbu11    TTTGGAAATTGCCTCAAGAAGAAAGTTCTATTCTGCCTGCCCTGAGACTTAGTTACCATCACCTTCCACTTGATTTGAGA
         IleTrpLysLeuProGlnGluGluSerSerIleLeuProAlaLeuArgLeuSerTyrHisHisLeuProLeuAspLeuArg>
         _____EXON2_____>

Sbu12    TTTGGAAATTGCCTCAAGAAGAAAGTTCTATTCTGCCgGCCCTGAaACTTAGTTACCATCAtCTTCCACTTGATTTGAGA>
         |||||||||||||||||||||||||||||||||||||*|||||||*|||||||||||||*|||||||||||||||||||
Sbu11    TTTGGAAATTGCCTCAAGAAGAAAGTTCTATTCTGCCTGCCCTGAGACTTAGTTACCATCACCTTCCACTTGATTTGAGA
```

FIG. 7D

```
Sbul1    CAATGCTTTACATATTGTGCAGTATTCCCAAAGGATACCGAAATGGAAAAGGGAAATCTAATCTCTCTCTGGATGGCACA
         GlnCysPheThrTyrCysAlaValPheProLysAspThrGluMetGluLysGlyAsnLeuIleSerLeuTrpMetAlaHis>
         _____EXON2_____>

Sbul2    CAATGCTTTtCATATTGTGCAGTATTCCCAAAGGATACCaAAATGGAAAAGGaAAATCTAATCTCTCTCTGGATGGCACA>
         ||||||||*|||||||||||||||||||||||||||||*|||||||||||*|||||||||||||||||||||||||||||
Sbul1    CAATGCTTTACATATTGTGCAGTATTCCCAAAGGATACCGAAATGGAAAAGGGAAATCTAATCTCTCTCTGGATGGCACA Sbul1    TGGTTTTATTTTATCGAAAGGAAACTTGGAGCTAGAGAATGTAGGTAATGAAGTATGGAATGAATTATACTTGAGGTCTT
         GlyPheIleLeuSerLysGlyAsnLeuGluLeuGluAsnValGlyAsnGluValTrpAsnGluLeuTyrLeuArgSer>
         _____EXON2_____>

Sbul2    TGGTTTTcTTTTATCGAAAGGAAACTTGGAGCTAGAGgATGTAGGTAATGAAGTATGGAATGAATTATACTTGAGGTCTT>
         |||||||*|||||||||||||||||||||||||||||*||||||||||||||||||||||||||||||||||||||||||
Sbul1    TGGTTTTATTTTATCGAAAGGAAACTTGGAGCTAGAGAATGTAGGTAATGAAGTATGGAATGAATTATACTTGAGGTCTT Sbul1    TCTTCCAAGAGATTGAAGTTAAATCTGGTCAAACTTATTTCAAGATGCATGATCTCATTCATGATCTGGCAACATCTCTA
         PhePheGlnGluIleGluValLysSerGlyGlnThrTyrPheLysMetHisAspLeuIleHisAspLeuAlaThrSerLeu>
         _____EXON2_____>

Sbul2    TCTTCCAAGAGATTGAAGTTAcATaTGGTaAAACTTATTTCAAGATGCATGATCTCATcCATGATtTGGCtACATCTCTA>
         ||||||||||||||||||||||*||*|||*||||||||||||||||||||||||||||*||||||*||||*|||||||||
Sbul1    TCTTCCAAGAGATTGAAGTTAAATCTGGTCAAACTTATTTCAAGATGCATGATCTCATTCATGATCTGGCAACATCTCTA Sbul1    TTTTCGGCAAGCACATCAAGCAGCAATATCCGAGAAATAATTGTAGAAAATTACATACATATGATGTCCATTGGTTTCAC
         PheSerAlaSerThrSerSerSerAsnIleArgGluIleIleValGluAsnTyrIleHisMetMetSerIleGlyPheThr>
         _____EXON2_____>

Sbul2    TTTTCGGCAAGCgCATCAAGCAaCAATATCCGtGAAATAAtGTAaAAggTTACcCACATATGATGTCgATTGGCTTtgC>
         |||||||||||*|||||||||*|||||||||*|||||||*|||**|||**|||||||||||||||*||||*||**|
Sbul1    TTTTCGGCAAGCACATCAAGCAGCAATATCCGAGAAATAATTGTAGAAAATTACATACATATGATGTCCATTGGTTTCAC Sbul1    TAAAGTGGTATCTTCTTACTCTCTTTCCCACTTGCAGAAGTTTGTCTCGTTGAGGGTGCTTAATCTAAGTGACATAAAAC
         LysValValSerSerTyrSerLeuSerHisLeuGlnLysPheValSerLeuArgValLeuAsnLeuSerAspIleLys>
         _____EXON2_____>

Sbul2    aAAAGTGGTgTCTTtTTACTCTCgTTCtCACTTcCAaAGTTTGTCTCGTTaAGGGTGCTTAATCTAAGTaACtTAgAAC>
         *||||||||*||||*|||||||*|||*|||||*||*|||||||||||||*||||||||||||||||||||*||*||*|||
Sbul1    TAAAGTGGTATCTTCTTACTCTCTTTCCCACTTGCAGAAGTTTGTCTCGTTGAGGGTGCTTAATCTAAGTGACATAAAAC
```

FIG. 7E

```
Sbu1        TTAAGCAGTTACCGTCTTCCATTGGAGATCTAGTACATTTAAGATACCTAAACTTGTCTGGCAATACTAGTATTCGTAGT
            LeuLysGlnLeuProSerSerIleGlyAspLeuValHisLeuArgTyrLeuAsnLeuSerGlyAsnThrSerIleArgSer>
            _____EXON2_____>

Sbu12       TcAAGCAGTTACCaTCTTCaATTGGgGATCTAGTACATTTAAGATACCTAAACTTGTCTGaCAATAaTAGaATTCGTAGT>
            |*||||||||||*||||*|||||*||||||||||||||||||||||||||||||||*||||*|||*||||||||||
Sbu1        TTAAGCAGTTACCGTCTTCCATTGGAGATCTAGTACATTTAAGATACCTAAACTTGTCTGGCAATACTAGTATTCGTAGT

Sbu1        CTTCCAAACCAGTTATGCAAGCTTCAAAATCTGCAGACTCTTGATCTACATGGCTGTCATTCACTTTGTTGTTTGCCAAA
            LeuProAsnGlnLeuCysLysLeuGlnAsnLeuGlnThrLeuAspLeuHisGlyCysHisSerLeuCysCysLeuProLys>
            _____EXON2_____>

Sbu12       CTTCCcAAgCAGTTATGCAAGCTTCAAAATCTGCAGACTCTTGATCTACgTtGtTGctAcagACTTTcTTGTTTGCCAAA>
            |||||*||*|||||||||||||||||||||||||||||||||||||||*|*|*||**|***||||*|||||||||||
Sbu1        CTTCCAAACCAGTTATGCAAGCTTCAAAATCTGCAGACTCTTGATCTACATGGCTGTCATTCACTTTGTTGTTTGCCAAA Sbu1        AGAAACAAGCAAACTTGGTAGTCTTCGAAATCTTTTACTTGATGGTTGCTATGGATTGACTTGTATGCCACCAAGGATAG
            GluThrSerLysLeuGlySerLeuArgAsnLeuLeuLeuAspGlyCysTyrGlyLeuThrCysMetProProArgIle>
            _____EXON2_____>

Sbu12       AGAAACAAGCAAACTTGGTAGTCTcCGAAATCTTTTACTTGATcGTTGCcATGGATTGACTTGTATGCCACCAAGGATAG>
            |||||||||||||||||||||||||*||||||||||||||||*||||*|||||||||||||||||||||||||||||
Sbu1        AGAAACAAGCAAACTTGGTAGTCTTCGAAATCTTTTACTTGATGGTTGCTATGGATTGACTTGTATGCCACCAAGGATAG

Sbu1        GATCTTTGACATGCCTTAAGACTCTAAGTAGATTTGTGGTGGGAATTCAGAAGAAAAGTTGTCAACTTGGTGAATTACGA
            GlySerLeuThrCysLeuLysThrLeuSerArgPheValValGlyIleGlnLysLysSerCysGlnLeuGlyGluLeuArg>
            _____EXON2_____>

Sbu12       GATCATTGACATGCCTTAAGACTCTAGATCGCTTTGCAATGGGAA---GGGAGAAAAGTCCTCAAATTGGTGAATTACGA
            ||||*||||||||||||||||||||||**|*|*||||***|||||****|*||||||||**||||*|||||||||||||
Sbu1        GATCTTTGACATGCCTTAAGACTCTAAGTAGATTTGTGGTGGGAATTCAGAAGAAAAGTTGTCAACTTGGTGAATTACGA

Sbu1        AACCTGAATCTCTATGGCTCAATTGAAATCACGCATCTTGAGAGAGTGAAGAATGATATGGATGCAAAAGAAGCCAATTT
            AsnLeuAsnLeuTyrGlySerIleGluIleThrHisLeuGluArgValLysAsnAspMetAspAlaLysGluAlaAsnLeu>
            _____EXON2_____>

Sbu12       AACCTGAATCTCTATGGCTCAATTcAATCACGCATCTTGAGAGAGTGAAGAATGATATGGATGCAAAAGAAGCCAATTT>
            ||||||||||||||||||||||||||**|||||||||||||||||||||||||||||||||||||||||||||||||
Sbu1        AACCTGAATCTCTATGGCTCAATTGAAATCACGCATCTTGAGAGAGTGAAGAATGATATGGATGCAAAAGAAGCCAATTT
```

FIG. 7F

```
Sbu11    ATCTGCAAAAGAAAATCTGCATTCTTTAAGCATGAAATGGGATGACGATGAACGTCCACGTATATATGAATCAGAAAAAG
         SerAlaLysGluAsnLeuHisSerLeuSerMetLysTrpAspAspAspGluArgProArgIleTyrGluSerGluLys>
         _____EXON2_____>

Sbu12    ATCTtCAAAAGAAAATCTGCATTCTTTAAGtATGAtATGGGATGAaGATGAACGTCCACaTAgATATGAATCAGAAgATG>
         ||||*||||||||||||||||||||||||||*||||*|||||||||*||||||||||||*||*|||||||||||||*|*|
Sbu11    ATCTGCAAAAGAAAATCTGCATTCTTTAAGCATGAAATGGGATGACGATGAACGTCCACGTATATATGAATCAGAAAAAG

Sbu11    TTGAAGTGCTTGAAGCTCTCAAACCACACTCCAATCTGACTTGTTTAACAATCAGGGGCTTCAGAGGAATCCGTCTCCCA
         ValGluValLeuGluAlaLeuLysProHisSerAsnLeuThrCysLeuThrIleArgGlyPheArgGlyIleArgLeuPro>
         _____EXON2_____>

Sbu12    TTGAAGTGCTTGAAGCcCTCAAACCACACTCCAATCTGACTTGTTTAACAATtAttGGCTTCAGAGGAATCCGTCTCCCA>
         |||||||||||||||*||||||||||||||||||||||||||||||||||*|**|||||||||||||||||||||||||
Sbu11    TTGAAGTGCTTGAAGCTCTCAAACCACACTCCAATCTGACTTGTTTAACAATCAGGGGCTTCAGAGGAATCCGTCTCCCA

Sbu11    GACTGGATGAATCACTCAGTTTTGAAAAATGTTGTCTCTATTGAAATCATCAGTTGCAAAAACTGCTCATGCTTACCACC
         AspTrpMetAsnHisSerValLeuLysAsnValValSerIleGluIleIleSerCysLysAsnCysSerCysLeuProPro>
         _____EXON2_____>

Sbu12    GACTGGATGAATCACTCAGTTTTGAAAAATGTTGTCTCTcTTGAAATCAgCgaTTGCAAAAACTGCTCATGCTTACCACC>
         |||||||||||||||||||||||||||||||||||||||*|||||||||*|**|||||||||||||||||||||||||||
Sbu11    GACTGGATGAATCACTCAGTTTTGAAAAATGTTGTCTCTATTGAAATCATCAGTTGCAAAAACTGCTCATGCTTACCACC

Sbu11    CTTTGGTGAGCTGCCTTGTCTAAAAAGTCTAGAGTTATGGAGGGGGTCTGCGGAAGTGGAGTATGTTGATTCTGGATTCC
         PheGlyGluLeuProCysLeuLysSerLeuGluLeuTrpArgGlySerAlaGluValGluTyrValAspSerGlyPhe>
         _____EXON2_____>

Sbu12    CTTTGGTGAaCTGCCTTGTCTAAAtAGTCTAcAGTTATGGAGtGGGTCTGCaGAAGTGGAGTATaTTGATTCTGGATTCC>
         |||||||||*|||||||||||||*||||||*||||||||||*|||||||*||||||||||||*|||||||||||||||||
Sbu11    CTTTGGTGAGCTGCCTTGTCTAAAAAGTCTAGAGTTATGGAGGGGGTCTGCGGAAGTGGAGTATGTTGATTCTGGATTCC

Sbu11    CTACAAGAAGAAGGTTTCCATCTCTGAGAAAACTTAATATACGCGAATTTGATAATCTGAAAGGATTGCTGAAAAAGGAA
         ProThrArgArgArgPheProSerLeuArgLysLeuAsnIleArgGluPheAspAsnLeuLysGlyLeuLeuLysLysGlu>
         _____EXON2_____>

Sbu12    CTACAAGAAGAAGGTTTCCATCTCTGAGAAAACTTAtTATAgGCGAATTTGATAATCTGAAAGGATTGgTGAAAAAGGAA>
         ||||||||||||||||||||||||||||||||||||*||||*|||||||||||||||||||||||||*||||||||||||
Sbu11    CTACAAGAAGAAGGTTTCCATCTCTGAGAAAACTTAATATACGCGAATTTGATAATCTGAAAGGATTGCTGAAAAAGGAA
```

FIG. 7G

```
Sbu11    GGAGAAGAGCAATGCCCTGTGCTTGAAGAGATAGAGATTAAATGTTGCCCTATGTTTGTTATTCCAACCCTTTCTTCTGT
          GlyGluGluGlnCysProValLeuGluGluIleGluIleLysCysCysProMetPheValIleProThrLeuSerSerVal>
         _____EXON2_____>

Sbu12    GGAGAAGAGCAATtCCCTGTGCTTGAAGAGATgGAGATTAAcTGgTGCCCTATGTTTGTTATTCCgACCCTTTCTTCTGT>
         ||||||||||||*||||||||||||||||||*|||||||||*||*||||||||||||||||||||||*||||||||||||
Sbu11    GGAGAAGAGCAATGCCCTGTGCTTGAAGAGATAGAGATTAAATGTTGCCCTATGTTTGTTATTCCAACCCTTTCTTCTGT

Sbu11    CAAGAAATTGGTAGTTAGTGGGGACAAGTCAGATGCAATAGGTTTCAGTTCCATATCTAATCTCATGGCTCTTACTTCCC
          LysLysLeuValValSerGlyAspLysSerAspAlaIleGlyPheSerSerIleSerAsnLeuMetAlaLeuThrSer>
         _____EXON2_____>

Sbu12    CAAcAAATTGGTAGTTAGTGGGGAagAGTCAGATGCAATAGGcTTCAGTTCCATATCTAATCTCAgGGCTCTTACTTCtC>
         |||*||||||||||||||||||||**||||||||||||||*|||||||||||||||||||||||*|||||||||||||*|
Sbu11    CAAGAAATTGGTAGTTAGTGGGGACAAGTCAGATGCAATAGGTTTCAGTTCCATATCTAATCTCATGGCTCTTACTTCCC

Sbu11    TCCAAATTCGCTATAACAAAGAAGATGCTTCACTCCCAGAAGAGATGTTCAAAAGCCTTGCAAATCTCAAATACTTGAAT
          LeuGlnIleArgTyrAsnLysGluAspAlaSerLeuProGluGluMetPheLysSerLeuAlaAsnLeuLysTyrLeuAsn>
         _____EXON2_____>

Sbu12    TCaAtATTaGCTATAACtctGAAGcTaCTTCACTCCCAGAAGAGATGTTCAAAAGCCTTGCAAATCTaAAATACTTGAAT>
         ||*|*|||*|||||||***|||*|*|||||||||||||||||||||||||||||||||||||||||*||||||||||||
Sbu11    TCCAAATTCGCTATAACAAAGAAGATGCTTCACTCCCAGAAGAGATGTTCAAAAGCCTTGCAAATCTCAAATACTTGAAT Sbu11    ATCTCTTTTTACTTCAATCTTAAAGAGCTGCCTACCAGCCTGGCTAGTCTCAATGCTTTGAAGCATCTGGAAATTCATAG
          IleSerPheTyrPheAsnLeuLysGluLeuProThrSerLeuAlaSerLeuAsnAlaLeuLysHisLeuGluIleHisSer>
         _____EXON2_____>

Sbu12    ATCTaTTacTtCaagAATCTcAAAGAGCTGCCTACCAaCCTGGCTAGTCTtAATGCTTTGAAGaATCTGGAAATTgAaAG>
         ||||*||**|*|***|||||*||||||||||||||||*||||||||||||*|||||||||||*||||||||||||*|*||
Sbu11    ATCTCTTTTTACTTCAATCTTAAAGAGCTGCCTACCAGCCTGGCTAGTCTCAATGCTTTGAAGCATCTGGAAATTCATAG Sbu11    TTGTTATGCACTAGAGAGTCTCCCCGAGGAAGGTGTGAAAGGTTTAATTTCACTCACACAGTTATCCATAACATACTGTG
          CysTyrAlaLeuGluSerLeuProGluGluGlyValLysGlyLeuIleSerLeuThrGlnLeuSerIleThrTyrCys>
         _____EXON2_____>

Sbu12    TTGTTATGCACTAGAGAGTCTCCCCGAGGAAGGTGTGAAAGGTTTAAcTTCACTtACACAaTTATCCATAACATACTGca>
         |||||||||||||||||||||||||||||||||||||||||||||||*||||||*|||||*||||||||||||||||**
Sbu11    TTGTTATGCACTAGAGAGTCTCCCCGAGGAAGGTGTGAAAGGTTTAATTTCACTCACACAGTTATCCATAACATACTGTG
```

FIG. 7H

```
Sbu11    AAATGCTACAATGTTTACCGGAGGGATTGCAGCACCTAACAGCCCTCACAAATTTATCAGTTGAGTTTTGTCCAACACTG
         GluMetLeuGlnCysLeuProGluGlyLeuGlnHisLeuThrAlaLeuThrAsnLeuSerValGluPheCysProThrLeu>
         ――――――――――――――――――――――――――――――――EXON2――――――――――――――――――――――――――――――――――――――>

Sbu12    cgATGCTACAATGTTTAtCGGAGGGATTGCAGCACCTAACAGCCCTCACAAATTTATCAGTTagGgaTTGTCCAACACTG>
         **|||||||||||||||*||||||||||||||||||||||||||||||||||||||||||**|**|||||||||||||
Sbu11    AAATGCTACAATGTTTACCGGAGGGATTGCAGCACCTAACAGCCCTCACAAATTTATCAGTTGAGTTTTGTCCAACACTG

Sbu11    GCCAAGCGGTGTGAGAAGGGAATAGGAGAAGACTGGTACAAAATTGCTCACATTCCTCGTGTGTTTATTTATTAGTATTC
         AlaLysArgCysGluLysGlyIleGlyGluAspTrpTyrLysIleAlaHisIleProArgValPheIleTyr***>
         ――――――――――――――――――――――――――――――――EXON2――――――――――――――――――――――――――――――――――――――>

Sbu12    GCCAAGCGaTGTGAGAAGGGAATAGGAGAAGACTGGTACAAAATTGCTCACATTCCTgaTGTGTTTATccgTTAagTctTATTC>
         |||||||*|||||||||||||||||||||||||||||||||||||||||||||**|||||||***||**|**|||||
Sbu11    GCCAAGCGGTGTGAGAAGGGAATAGGAGAAGACTGGTACAAAATTGCTCACATTCCTCGTGTGTTTAT---TTA-TTAGTATTC Sbu11    CCAATTAGATGTAATTTTCTGATTTTCTTTTGGAAACAAATCAACTATTTGTAAGATCTATTTGTATTATACTTGATTTT
Sbu12    CtAATTAGATGTAATTTTCTGATTTTtCTTTTGgAAaCAAATCAAtTATTTGTA-------------TTATACTTGATTTT
         |*|||||||||||||||||||||||**|||*|*||*|||||||||*|||||||*************|||||||||||||
Sbu11    CCAATTAGATGTAATTTTCTGATTTTCTTTTGGAAA-CAAATCAACTATTTGTAAGATCTATTTGTATTATACTTGATTTT Sbu11    TCTTGGGTCTGTAACAATAAATATTTGAAATTTTTCATATTAAGATTCAGAATTAGTCTTATAGCTAACGGTATC
Sbu12    TCTTGGGTCTaTAACAATAAATATTTGAAATTTTTCATATTAAGATTCAGAATTAGTCTTATAGCaAACtGTAcC>
         ||||||||||*|||||||||||||||||||||||||||||||||||||||||||||||||||||||*|||*|||*|
Sbu11    TCTTGGGTCTGTAACAATAAATATTTGAAATTTTTCATATTAAGATTCAGAATTAGTCTTATAGCTAACGGTATC
```

FIG. 7I

SEQUENCE LISTING

```
<160> NUMBER OF SEQ ID NOS: 10

<210> SEQ ID NO 1
<211> LENGTH: 3193
<212> TYPE: DNA
<213> ORGANISM: Solanum bulbocastanum
<220> FEATURE:
<221> NAME/KEY: CDS
<222> LOCATION: (52)..(3018)

<400> SEQUENCE: 1
atcttacttc atttcaaaaa atatagattc attgcgtact cacaatactc t atg gct      57
                                                          Met Ala
                                                            1 gaa gct ttc ctt caa gtt ctg tta gac aat ctg act tgt ttc atc caa    105
Glu Ala Phe Leu Gln Val Leu Leu Asp Asn Leu Thr Cys Phe Ile Gln
        5                  10                  15 ggg gaa ctt gga ttg att ctt ggt ttt aag gat gag ttc gaa aag ctt    153
Gly Glu Leu Gly Leu Ile Leu Gly Phe Lys Asp Glu Phe Glu Lys Leu
 20                  25                  30 caa agc acg ttt act aca atc caa gct gtg cta gaa gat gct cag aag    201
Gln Ser Thr Phe Thr Thr Ile Gln Ala Val Leu Glu Asp Ala Gln Lys
 35                  40                  45                  50 aag caa ttg aag gac aag gca ata gaa aat tgg ttg cag aaa ctc aat    249
Lys Gln Leu Lys Asp Lys Ala Ile Glu Asn Trp Leu Gln Lys Leu Asn
                 55                  60                  65 gct gct gca tat gag gct gat gac atc ttg gac gaa tgt aaa act gag    297
Ala Ala Ala Tyr Glu Ala Asp Asp Ile Leu Asp Glu Cys Lys Thr Glu
             70                  75                  80 gca cca att aga cag aag aag aac aaa tat ggg tgt tat cat cca aac    345
Ala Pro Ile Arg Gln Lys Lys Asn Lys Tyr Gly Cys Tyr His Pro Asn
         85                  90                  95 gtt atc act ttt cgt cac aag att ggg aaa agg atg aaa aag att atg    393
Val Ile Thr Phe Arg His Lys Ile Gly Lys Arg Met Lys Lys Ile Met
    100                 105                 110 gag aaa cta gat gta att gca gcg gaa cga att aag ttt cat ttg gat    441
Glu Lys Leu Asp Val Ile Ala Ala Glu Arg Ile Lys Phe His Leu Asp
115                 120                 125                 130 gaa agg act ata gag aga caa gtt gct aca cgc caa aca ggt ttt gtt    489
Glu Arg Thr Ile Glu Arg Gln Val Ala Thr Arg Gln Thr Gly Phe Val
                135                 140                 145 ttg aat gaa cca caa gtt tat gga aga gac aaa gaa aag gac gag ata    537
Leu Asn Glu Pro Gln Val Tyr Gly Arg Asp Lys Glu Lys Asp Glu Ile
            150                 155                 160 gtg aaa atc cta ata aac aat gtt agc aat gcc caa aca ctt cca gtc    585
Val Lys Ile Leu Ile Asn Asn Val Ser Asn Ala Gln Thr Leu Pro Val
        165                 170                 175
```

-continued

```
ctc cca ata ctt ggt atg ggg gga cta gga aag acg act ctt gcc caa      633
Leu Pro Ile Leu Gly Met Gly Gly Leu Gly Lys Thr Thr Leu Ala Gln
    180                 185                 190 atg gtc ttc aat gat cag aga gta att gag cat ttc cat ccc aaa ata      681
Met Val Phe Asn Asp Gln Arg Val Ile Glu His Phe His Pro Lys Ile
195                 200                 205                 210 tgg att tgt gtc tcg gaa gat ttt aat gag aag agg ttg ata aag gaa      729
Trp Ile Cys Val Ser Glu Asp Phe Asn Glu Lys Arg Leu Ile Lys Glu
                215                 220                 225 att gta gaa tct att gaa gaa aag tca ctt ggt ggc atg gac ttg gct      777
Ile Val Glu Ser Ile Glu Glu Lys Ser Leu Gly Gly Met Asp Leu Ala
                230                 235                 240 cca ctt caa aag aag ctt cgg gac ttg ctg aat gga aaa aaa tat ttg      825
Pro Leu Gln Lys Lys Leu Arg Asp Leu Leu Asn Gly Lys Lys Tyr Leu
            245                 250                 255 ctc gtc tta gat gat gtt tgg aat gaa gat caa gat aag tgg gct aag      873
Leu Val Leu Asp Asp Val Trp Asn Glu Asp Gln Asp Lys Trp Ala Lys
260                 265                 270 tta aga caa gtc ttg aag gtt gga gca agt ggc gct tct gtt cta acc      921
Leu Arg Gln Val Leu Lys Val Gly Ala Ser Gly Ala Ser Val Leu Thr
275                 280                 285                 290 act act cgt ctt gaa aag gtt gga tca att atg gga aca ttg caa cca      969
Thr Thr Arg Leu Glu Lys Val Gly Ser Ile Met Gly Thr Leu Gln Pro
                295                 300                 305 tat gaa ttg tca aat ttg tct caa gaa gat tgt tgg ttg ttc atg         1017
Tyr Glu Leu Ser Asn Leu Ser Gln Glu Asp Cys Trp Leu Leu Phe Met
                310                 315                 320 caa cgt gca ttt ggg cac caa gaa gaa ata aat ctt aat ctt gtg gct     1065
Gln Arg Ala Phe Gly His Gln Glu Glu Ile Asn Leu Asn Leu Val Ala
            325                 330                 335 atc gga aag gag att gtg aaa aaa tgt ggt ggt gtg cct cta gca gct     1113
Ile Gly Lys Glu Ile Val Lys Lys Cys Gly Gly Val Pro Leu Ala Ala
340                 345                 350 aaa act ctt gga ggt att ttg cgc ttt aag aga gaa gaa aga cag tgg     1161
Lys Thr Leu Gly Gly Ile Leu Arg Phe Lys Arg Glu Glu Arg Gln Trp
355                 360                 365                 370 gaa cat gtg aga gat agt gag att tgg aaa ttg cct caa gaa gaa agt     1209
Glu His Val Arg Asp Ser Glu Ile Trp Lys Leu Pro Gln Glu Glu Ser
                375                 380                 385 tct att ctg cct gcc ctg aga ctt agt tac cat cac ctt cca ctt gat     1257
Ser Ile Leu Pro Ala Leu Arg Leu Ser Tyr His His Leu Pro Leu Asp
                390                 395                 400 ttg aga caa tgc ttt aca tat tgt gca gta ttc cca aag gat acc gaa     1305
Leu Arg Gln Cys Phe Thr Tyr Cys Ala Val Phe Pro Lys Asp Thr Glu
            405                 410                 415 atg gaa aag gga aat cta atc tct ctc tgg atg gca cat ggt ttt att     1353
Met Glu Lys Gly Asn Leu Ile Ser Leu Trp Met Ala His Gly Phe Ile
420                 425                 430 tta tcg aaa gga aac ttg gag cta gag aat gta ggt aat gaa gta tgg     1401
Leu Ser Lys Gly Asn Leu Glu Leu Glu Asn Val Gly Asn Glu Val Trp
435                 440                 445                 450 aat gaa tta tac ttg agg tct ttc ttc caa gag att gaa gtt aaa tct     1449
Asn Glu Leu Tyr Leu Arg Ser Phe Phe Gln Glu Ile Glu Val Lys Ser
                455                 460                 465 ggt caa act tat ttc aag atg cat gat ctc att cat gat ctg gca aca     1497
Gly Gln Thr Tyr Phe Lys Met His Asp Leu Ile His Asp Leu Ala Thr
            470                 475                 480 tct cta ttt tcg gca agc aca tca agc agc aat atc cga gaa ata att     1545
Ser Leu Phe Ser Ala Ser Thr Ser Ser Ser Asn Ile Arg Glu Ile Ile
```

```
                485                 490                 495
gta gaa aat tac ata cat atg atg tcc att ggt ttc act aaa gtg gta    1593
Val Glu Asn Tyr Ile His Met Met Ser Ile Gly Phe Thr Lys Val Val
    500                 505                 510 tct tct tac tct ctt tcc cac ttg cag aag ttt gtc tcg ttg agg gtg    1641
Ser Ser Tyr Ser Leu Ser His Leu Gln Lys Phe Val Ser Leu Arg Val
515                 520                 525                 530 ctt aat cta agt gac ata aaa ctt aag cag tta ccg tct tcc att gga    1689
Leu Asn Leu Ser Asp Ile Lys Leu Lys Gln Leu Pro Ser Ser Ile Gly
                535                 540                 545 gat cta gta cat tta aga tac cta aac ttg tct ggc aat act agt att    1737
Asp Leu Val His Leu Arg Tyr Leu Asn Leu Ser Gly Asn Thr Ser Ile
                550                 555                 560 cgt agt ctt cca aac cag tta tgc aag ctt caa aat ctg cag act ctt    1785
Arg Ser Leu Pro Asn Gln Leu Cys Lys Leu Gln Asn Leu Gln Thr Leu
                565                 570                 575 gat cta cat ggc tgt cat tca ctt tgt tgt ttg cca aaa gaa aca agc    1833
Asp Leu His Gly Cys His Ser Leu Cys Cys Leu Pro Lys Glu Thr Ser
                580                 585                 590 aaa ctt ggt agt ctt cga aat ctt tta ctt gat ggt tgc tat gga ttg    1881
Lys Leu Gly Ser Leu Arg Asn Leu Leu Leu Asp Gly Cys Tyr Gly Leu
595                 600                 605                 610 act tgt atg cca cca agg ata gga tct ttg aca tgc ctt aag act cta    1929
Thr Cys Met Pro Pro Arg Ile Gly Ser Leu Thr Cys Leu Lys Thr Leu
                615                 620                 625 agt aga ttt gtg gtg gga att cag aag aaa agt tgt caa ctt ggt gaa    1977
Ser Arg Phe Val Val Gly Ile Gln Lys Lys Ser Cys Gln Leu Gly Glu
                630                 635                 640 tta cga aac ctg aat ctc tat ggc tca att gaa atc acg cat ctt gag    2025
Leu Arg Asn Leu Asn Leu Tyr Gly Ser Ile Glu Ile Thr His Leu Glu
                645                 650                 655 aga gtg aag aat gat atg gat gca aaa gaa gcc aat tta tct gca aaa    2073
Arg Val Lys Asn Asp Met Asp Ala Lys Glu Ala Asn Leu Ser Ala Lys
                660                 665                 670 gaa aat ctg cat tct tta agc atg aaa tgg gat gac gat gaa cgt cca    2121
Glu Asn Leu His Ser Leu Ser Met Lys Trp Asp Asp Asp Glu Arg Pro
675                 680                 685                 690 cgt ata tat gaa tca gaa aaa gtt gaa gtg ctt gaa gct ctc aaa cca    2169
Arg Ile Tyr Glu Ser Glu Lys Val Glu Val Leu Glu Ala Leu Lys Pro
                695                 700                 705 cac tcc aat ctg act tgt tta aca atc agg ggc ttc aga gga atc cgt    2217
His Ser Asn Leu Thr Cys Leu Thr Ile Arg Gly Phe Arg Gly Ile Arg
                710                 715                 720 ctc cca gac tgg atg aat cac tca gtt tgt aaa aat gtt gtc tct att    2265
Leu Pro Asp Trp Met Asn His Ser Val Leu Lys Asn Val Val Ser Ile
                725                 730                 735 gaa atc atc agt tgc aaa aac tgc tca tgc tta cca ccc ttt ggt gag    2313
Glu Ile Ile Ser Cys Lys Asn Cys Ser Cys Leu Pro Pro Phe Gly Glu
740                 745                 750 ctg cct tgt cta aaa agt cta gag ttg tgg agg ggg tct gcg gaa gtg    2361
Leu Pro Cys Leu Lys Ser Leu Glu Leu Trp Arg Gly Ser Ala Glu Val
755                 760                 765                 770 gag tat gtt gat tct gga ttc cct aca aga aga agg ttt cca tct ctg    2409
Glu Tyr Val Asp Ser Gly Phe Pro Thr Arg Arg Arg Phe Pro Ser Leu
                775                 780                 785 aga aaa ctt aat ata cgc gaa ttt ggt aat ctg aaa gga ttg ctg aaa    2457
Arg Lys Leu Asn Ile Arg Glu Phe Gly Asn Leu Lys Gly Leu Leu Lys
                790                 795                 800 aag gaa gga gaa gag caa tgc cct gtg ctt gaa gag ata gag att aaa    2505
```

|                                                                 |      |
|-----------------------------------------------------------------|------|
| tgt tgc cct atg ttt gtt att cca acc ctt tct tct gtc aag aaa ttg | 2553 |
| Cys Cys Pro Met Phe Val Ile Pro Thr Leu Ser Ser Val Lys Lys Leu |      |
|     820             825                 830                     |      |
| gta gtt agt ggg gac aag tca gat gca ata ggt ttc agt tcc ata tct | 2601 |
| Val Val Ser Gly Asp Lys Ser Asp Ala Ile Gly Phe Ser Ser Ile Ser |      |
| 835                 840                 845                 850 |      |
| aat ctc atg gct ctt act tcc ctc caa att cgc tat aac aaa gaa gat | 2649 |
| Asn Leu Met Ala Leu Thr Ser Leu Gln Ile Arg Tyr Asn Lys Glu Asp |      |
|                 855                 860                 865     |      |
| gct tca ctc cca gaa gag atg ttc aaa agc ctt gca aat ctc aaa tac | 2697 |
| Ala Ser Leu Pro Glu Glu Met Phe Lys Ser Leu Ala Asn Leu Lys Tyr |      |
|             870                 875                 880         |      |
| ttg aat atc tct ttt tac ttc aat ctt aaa gag ctg cct acc agc ctg | 2745 |
| Leu Asn Ile Ser Phe Tyr Phe Asn Leu Lys Glu Leu Pro Thr Ser Leu |      |
|         885                 890                 895             |      |
| gct agt ctc aat gct ttg aag cat ctg gaa att cat agt tgt tat gca | 2793 |
| Ala Ser Leu Asn Ala Leu Lys His Leu Glu Ile His Ser Cys Tyr Ala |      |
|     900                 905                 910                 |      |
| cta gag agt ctc ccc gag gaa ggt gtg aaa ggt tta att tca ctc aca | 2841 |
| Leu Glu Ser Leu Pro Glu Glu Gly Val Lys Gly Leu Ile Ser Leu Thr |      |
| 915                 920                 925                 930 |      |
| cag tta tcc ata aca tac tgt gaa atg cta caa tgt tta ccg gag gga | 2889 |
| Gln Leu Ser Ile Thr Tyr Cys Glu Met Leu Gln Cys Leu Pro Glu Gly |      |
|                 935                 940                 945     |      |
| ttg cag cac cta aca gcc ctc aca aat tta tca gtt gag ttt tgt cca | 2937 |
| Leu Gln His Leu Thr Ala Leu Thr Asn Leu Ser Val Glu Phe Cys Pro |      |
|             950                 955                 960         |      |
| aca ctg gcc aag cgg tgt gag aag gga ata gga gaa gac tgg tac aaa | 2985 |
| Thr Leu Ala Lys Arg Cys Glu Lys Gly Ile Gly Glu Asp Trp Tyr Lys |      |
|         965                 970                 975             |      |
| att gct cac att cct cgt gtg ttt att tat tag tattcccaat tagatgtaat | 3038 |
| Ile Ala His Ile Pro Arg Val Phe Ile Tyr                         |      |
|     980                 985                                     |      |
| tttctgattt tcttttggaa acaaatcaac tatttgtaag atctatttgt attatacttg | 3098 |
| attttcttg ggtctgtaac aataaatatt tgaatttttt catattaaga ttcagaatta | 3158 |
| gtcttatagt caaaaaaaaa aaaaaaaaaa aaaaa                          | 3193 |

<210> SEQ ID NO 2
<211> LENGTH: 988
<212> TYPE: PRT
<213> ORGANISM: Solanum bulbocastanum

<400> SEQUENCE: 2

Met Ala Glu Ala Phe Leu Gln Val Leu Leu Asp Asn Leu Thr Cys Phe
1               5                   10                  15

Ile Gln Gly Glu Leu Gly Leu Ile Leu Gly Phe Lys Asp Glu Phe Glu
            20                  25                  30

Lys Leu Gln Ser Thr Phe Thr Thr Ile Gln Ala Val Leu Glu Asp Ala
        35                  40                  45

Gln Lys Lys Gln Leu Lys Asp Lys Ala Ile Glu Asn Trp Leu Gln Lys
    50                  55                  60

Leu Asn Ala Ala Ala Tyr Glu Ala Asp Asp Ile Leu Asp Glu Cys Lys
65                  70                  75                  80

Thr Glu Ala Pro Ile Arg Gln Lys Lys Asn Lys Tyr Gly Cys Tyr His
                85                  90                  95

-continued

```
Pro Asn Val Ile Thr Phe Arg His Lys Ile Gly Lys Arg Met Lys Lys
            100                 105                 110

Ile Met Glu Lys Leu Asp Val Ile Ala Ala Glu Arg Ile Lys Phe His
            115                 120                 125

Leu Asp Glu Arg Thr Ile Glu Arg Gln Val Ala Thr Arg Gln Thr Gly
            130                 135                 140

Phe Val Leu Asn Glu Pro Gln Val Tyr Gly Arg Asp Lys Glu Lys Asp
145                 150                 155                 160

Glu Ile Val Lys Ile Leu Ile Asn Asn Val Ser Asn Ala Gln Thr Leu
                165                 170                 175

Pro Val Leu Pro Ile Leu Gly Met Gly Leu Gly Lys Thr Thr Leu
            180                 185                 190

Ala Gln Met Val Phe Asn Asp Gln Arg Val Ile Glu His Phe His Pro
            195                 200                 205

Lys Ile Trp Ile Cys Val Ser Glu Asp Phe Asn Glu Lys Arg Leu Ile
            210                 215                 220

Lys Glu Ile Val Glu Ser Ile Glu Glu Lys Ser Leu Gly Gly Met Asp
225                 230                 235                 240

Leu Ala Pro Leu Gln Lys Lys Leu Arg Asp Leu Leu Asn Gly Lys Lys
                245                 250                 255

Tyr Leu Leu Val Leu Asp Asp Val Trp Asn Glu Asp Gln Asp Lys Trp
            260                 265                 270

Ala Lys Leu Arg Gln Val Leu Lys Val Gly Ala Ser Gly Ala Ser Val
            275                 280                 285

Leu Thr Thr Arg Leu Glu Lys Val Gly Ser Ile Met Gly Thr Leu
290                 295                 300

Gln Pro Tyr Glu Leu Ser Asn Leu Ser Gln Glu Asp Cys Trp Leu Leu
305                 310                 315                 320

Phe Met Gln Arg Ala Phe Gly His Gln Glu Glu Ile Asn Leu Asn Leu
                325                 330                 335

Val Ala Ile Gly Lys Glu Ile Val Lys Lys Cys Gly Gly Val Pro Leu
            340                 345                 350

Ala Ala Lys Thr Leu Gly Gly Ile Leu Arg Phe Lys Arg Glu Glu Arg
            355                 360                 365

Gln Trp Glu His Val Arg Asp Ser Glu Ile Trp Lys Leu Pro Gln Glu
            370                 375                 380

Glu Ser Ser Ile Leu Pro Ala Leu Arg Leu Ser Tyr His His Leu Pro
385                 390                 395                 400

Leu Asp Leu Arg Gln Cys Phe Thr Tyr Cys Ala Val Phe Pro Lys Asp
                405                 410                 415

Thr Glu Met Glu Lys Gly Asn Leu Ile Ser Leu Trp Met Ala His Gly
            420                 425                 430

Phe Ile Leu Ser Lys Gly Asn Leu Glu Leu Glu Asn Val Gly Asn Glu
            435                 440                 445

Val Trp Asn Glu Leu Tyr Leu Arg Ser Phe Phe Gln Glu Ile Glu Val
            450                 455                 460

Lys Ser Gly Gln Thr Tyr Phe Lys Met His Asp Leu Ile His Asp Leu
465                 470                 475                 480

Ala Thr Ser Leu Phe Ser Ala Ser Thr Ser Ser Asn Ile Arg Glu
                485                 490                 495

Ile Ile Val Glu Asn Tyr Ile His Met Met Ser Ile Gly Phe Thr Lys
            500                 505                 510

Val Val Ser Ser Tyr Ser Leu Ser His Leu Gln Lys Phe Val Ser Leu
```

```
                 515                 520                 525
Arg Val Leu Asn Leu Ser Asp Ile Lys Leu Lys Gln Leu Pro Ser Ser
        530                 535                 540
Ile Gly Asp Leu Val His Leu Arg Tyr Leu Asn Leu Ser Gly Asn Thr
545                 550                 555                 560
Ser Ile Arg Ser Leu Pro Asn Gln Leu Cys Lys Leu Gln Asn Leu Gln
                565                 570                 575
Thr Leu Asp Leu His Gly Cys His Ser Leu Cys Cys Leu Pro Lys Glu
        580                 585                 590
Thr Ser Lys Leu Gly Ser Leu Arg Asn Leu Leu Leu Asp Gly Cys Tyr
        595                 600                 605
Gly Leu Thr Cys Met Pro Pro Arg Ile Gly Ser Leu Thr Cys Leu Lys
        610                 615                 620
Thr Leu Ser Arg Phe Val Val Gly Ile Gln Lys Lys Ser Cys Gln Leu
625                 630                 635                 640
Gly Glu Leu Arg Asn Leu Asn Leu Tyr Gly Ser Ile Glu Ile Thr His
                645                 650                 655
Leu Glu Arg Val Lys Asn Asp Met Asp Ala Lys Glu Ala Asn Leu Ser
        660                 665                 670
Ala Lys Glu Asn Leu His Ser Leu Ser Met Lys Trp Asp Asp Asp Glu
        675                 680                 685
Arg Pro Arg Ile Tyr Glu Ser Glu Lys Val Glu Val Leu Glu Ala Leu
        690                 695                 700
Lys Pro His Ser Asn Leu Thr Cys Leu Thr Ile Arg Gly Phe Arg Gly
705                 710                 715                 720
Ile Arg Leu Pro Asp Trp Met Asn His Ser Val Leu Lys Asn Val Val
                725                 730                 735
Ser Ile Glu Ile Ile Ser Cys Lys Asn Cys Ser Cys Leu Pro Pro Phe
        740                 745                 750
Gly Glu Leu Pro Cys Leu Lys Ser Leu Glu Leu Trp Arg Gly Ser Ala
        755                 760                 765
Glu Val Glu Tyr Val Asp Ser Gly Phe Pro Thr Arg Arg Phe Pro
        770                 775                 780
Ser Leu Arg Lys Leu Asn Ile Arg Glu Phe Gly Asn Leu Lys Gly Leu
785                 790                 795                 800
Leu Lys Lys Glu Gly Glu Gln Cys Pro Val Leu Glu Glu Ile Glu
                805                 810                 815
Ile Lys Cys Cys Pro Met Phe Val Ile Pro Thr Leu Ser Ser Val Lys
        820                 825                 830
Lys Leu Val Val Ser Gly Asp Lys Ser Asp Ala Ile Gly Phe Ser Ser
        835                 840                 845
Ile Ser Asn Leu Met Ala Leu Thr Ser Leu Gln Ile Arg Tyr Asn Lys
850                 855                 860
Glu Asp Ala Ser Leu Pro Glu Glu Met Phe Lys Ser Leu Ala Asn Leu
865                 870                 875                 880
Lys Tyr Leu Asn Ile Ser Phe Tyr Phe Asn Leu Lys Glu Leu Pro Thr
                885                 890                 895
Ser Leu Ala Ser Leu Asn Ala Leu Lys His Leu Glu Ile His Ser Cys
                900                 905                 910
Tyr Ala Leu Glu Ser Leu Pro Glu Glu Gly Val Lys Gly Leu Ile Ser
        915                 920                 925
Leu Thr Gln Leu Ser Ile Thr Tyr Cys Glu Met Leu Gln Cys Leu Pro
        930                 935                 940
```

```
Glu Gly Leu Gln His Leu Thr Ala Leu Thr Asn Leu Ser Val Glu Phe
945                 950                 955                 960

Cys Pro Thr Leu Ala Lys Arg Cys Glu Lys Gly Ile Gly Glu Asp Trp
            965                 970                 975

Tyr Lys Ile Ala His Ile Pro Arg Val Phe Ile Tyr
            980                 985

<210> SEQ ID NO 3
<211> LENGTH: 3595
<212> TYPE: DNA
<213> ORGANISM: Solanum bulbocastanum
<220> FEATURE:
<221> NAME/KEY: CDS
<222> LOCATION: (57)..(487)
<223> OTHER INFORMATION: Sbu11 protein
<220> FEATURE:
<221> NAME/KEY: Intron
<222> LOCATION: (488)..(899)
<220> FEATURE:
<221> NAME/KEY: CDS
<222> LOCATION: (900)..(3432)

<400> SEQUENCE: 3
```

| | |
|---|---:|
| ccaacatctt acttcatttc aaaaaatata gattcattgc gtactcacaa tactct atg<br>                                                   Met<br>                                                   1 | 59 |

```
gct gaa gct ttc ctt caa gtt ctg tta gac aat ctg act tgt ttc atc      107
Ala Glu Ala Phe Leu Gln Val Leu Leu Asp Asn Leu Thr Cys Phe Ile
        5                   10                  15 caa ggg gaa ctt gga ttg att ctt ggt ttt aag gat gag ttc gaa aag      155
Gln Gly Glu Leu Gly Leu Ile Leu Gly Phe Lys Asp Glu Phe Glu Lys
    20                  25                  30 ctt caa agc acg ttt act aca atc caa gct gtg cta gaa gat gct cag      203
Leu Gln Ser Thr Phe Thr Thr Ile Gln Ala Val Leu Glu Asp Ala Gln
35                  40                  45 aag aag caa ttg aag gac aag gca ata gaa aat tgg ttg cag aaa ctc      251
Lys Lys Gln Leu Lys Asp Lys Ala Ile Glu Asn Trp Leu Gln Lys Leu
50              55                  60                  65 aat gct gct gca tat gag gct gat gac atc ttg gac gaa tgt aaa act      299
Asn Ala Ala Ala Tyr Glu Ala Asp Asp Ile Leu Asp Glu Cys Lys Thr
            70                  75                  80 gag gca cca att aga cag aag aag aac aaa tat ggg tgt tat cat cca      347
Glu Ala Pro Ile Arg Gln Lys Lys Asn Lys Tyr Gly Cys Tyr His Pro
        85                  90                  95 aac gtt atc act ttt cgt cac aag att ggg aaa agg atg aaa aag att      395
Asn Val Ile Thr Phe Arg His Lys Ile Gly Lys Arg Met Lys Lys Ile
    100                 105                 110 atg gag aaa cta gat gta att gca gcg gaa cga att aag ttt cat ttg      443
Met Glu Lys Leu Asp Val Ile Ala Ala Glu Arg Ile Lys Phe His Leu
115                 120                 125 gat gaa agg act ata gag aga caa gtt gct aca cgc caa aca gg           487
Asp Glu Arg Thr Ile Glu Arg Gln Val Ala Thr Arg Gln Thr Gly
130                 135                 140 tgctcatctt agatattttt ctgaaaaaac agctttatat catcaaattc atgtgtgttt    547
tgggaattcg tctaatctaa atgttcgtct caagtctaag tagataagtg gatccagctt    607
tggatttatt aatctattag ctaaatcgt ttagtgaagt ttttaacata taaccctca      667 gataaatcca tagcttactc ataggattag gataggcccc caagtctaaa tgacaggata    727
aagccagagt tgttttagct cttataaatt aacaatgata ataatgtgaa ttcaaaaaag    787 tgcattttt taatttgaaa tatttctgct gcttctcaag cttatcattg tctttttact    847
```

-continued

| | |
|---|---|
| gtgcaaaatt ctactttgta tttttgctga ctcctaccga gcttgggcca gg t ttt<br>　　　　　　　　　　　　　　　　　　　　　　　　　　　　　　Phe<br>　　　　　　　　　　　　　　　　　　　　　　　　　　　　　　145 | 903 |
| gtt ttg aat gaa cca caa gtt tat gga aga gac aaa gaa aag gac gag<br>Val Leu Asn Glu Pro Gln Val Tyr Gly Arg Asp Lys Glu Lys Asp Glu<br>　　　　　　　150　　　　　　　　155　　　　　　　　160 | 951 |
| ata gtg aaa atc ctg ata aac aat gtt agc aat gcc caa aca ctt cca<br>Ile Val Lys Ile Leu Ile Asn Asn Val Ser Asn Ala Gln Thr Leu Pro<br>　　　165　　　　　　　　170　　　　　　　　175 | 999 |
| gtc ctc cca ata ctt ggt atg ggg gga cta gga aag acg act ctt gcc<br>Val Leu Pro Ile Leu Gly Met Gly Gly Leu Gly Lys Thr Thr Leu Ala<br>180　　　　　　　　185　　　　　　　　190 | 1047 |
| caa atg gtc ttc aat gat cag aga gta att gag cat ttc cat ccc aaa<br>Gln Met Val Phe Asn Asp Gln Arg Val Ile Glu His Phe His Pro Lys<br>　　195　　　　　　　　200　　　　　　　　205 | 1095 |
| ata tgg att tgt gtc tcg gaa gat ttt aat gag aag agg ttg ata aag<br>Ile Trp Ile Cys Val Ser Glu Asp Phe Asn Glu Lys Arg Leu Ile Lys<br>210　　　　　　　　215　　　　　　　　220　　　　　　　　225 | 1143 |
| gaa att gta gaa tct att gaa gaa aag tca ctt ggt ggc atg gac ttg<br>Glu Ile Val Glu Ser Ile Glu Glu Lys Ser Leu Gly Gly Met Asp Leu<br>　　　　　　　230　　　　　　　　235　　　　　　　　240 | 1191 |
| gct cca ctt caa aag aag ctt cgg gac ttg ctg aat gga aaa aaa tat<br>Ala Pro Leu Gln Lys Lys Leu Arg Asp Leu Leu Asn Gly Lys Lys Tyr<br>　　　245　　　　　　　　250　　　　　　　　255 | 1239 |
| ttg ctc gtc tta gat gat gtt tgg aat gaa gat caa gat aag tgg gct<br>Leu Leu Val Leu Asp Asp Val Trp Asn Glu Asp Gln Asp Lys Trp Ala<br>260　　　　　　　　265　　　　　　　　270 | 1287 |
| aag tta aga caa gtc ttg aag gtt gga gca agt ggc gct tct gtt cta<br>Lys Leu Arg Gln Val Leu Lys Val Gly Ala Ser Gly Ala Ser Val Leu<br>　　275　　　　　　　　280　　　　　　　　285 | 1335 |
| acc act act cgt ctt gaa aag gtt gga tca att atg gga aca ttg caa<br>Thr Thr Thr Arg Leu Glu Lys Val Gly Ser Ile Met Gly Thr Leu Gln<br>290　　　　　　　　295　　　　　　　　300　　　　　　　　305 | 1383 |
| cca tat gaa ttg tca aat ttg tct caa gaa gat tgt tgg ttg ttc<br>Pro Tyr Glu Leu Ser Asn Leu Ser Gln Glu Asp Cys Trp Leu Leu Phe<br>　　　　　　　310　　　　　　　　315　　　　　　　　320 | 1431 |
| atg caa cgt gca ttt ggg cac caa gaa gaa ata aat ctt aat ctt gtg<br>Met Gln Arg Ala Phe Gly His Gln Glu Glu Ile Asn Leu Asn Leu Val<br>　　　325　　　　　　　　330　　　　　　　　335 | 1479 |
| gct atc gga aag gag att gtg aaa aaa tgt ggt ggt gtg cct cta gca<br>Ala Ile Gly Lys Glu Ile Val Lys Lys Cys Gly Gly Val Pro Leu Ala<br>340　　　　　　　　345　　　　　　　　350 | 1527 |
| gct aaa act ctt gga ggt att ttg cgc ttt aag aga gaa gaa aga cag<br>Ala Lys Thr Leu Gly Gly Ile Leu Arg Phe Lys Arg Glu Glu Arg Gln<br>　　355　　　　　　　　360　　　　　　　　365 | 1575 |
| tgg gaa cat gtg aga gat agt gag att tgg aaa ttg cct caa gaa gaa<br>Trp Glu His Val Arg Asp Ser Glu Ile Trp Lys Leu Pro Gln Glu Glu<br>370　　　　　　　　375　　　　　　　　380　　　　　　　　385 | 1623 |
| agt tct att ctg cct gcc ctg aga ctt agt tac cat cac ctt cca ctt<br>Ser Ser Ile Leu Pro Ala Leu Arg Leu Ser Tyr His His Leu Pro Leu<br>　　　　　　　390　　　　　　　　395　　　　　　　　400 | 1671 |
| gat ttg aga caa tgc ttt aca tat tgt gca gta ttc cca aag gat acc<br>Asp Leu Arg Gln Cys Phe Thr Tyr Cys Ala Val Phe Pro Lys Asp Thr<br>　　　405　　　　　　　　410　　　　　　　　415 | 1719 |
| gaa atg gaa aag gga aat cta atc tct ctc tgg atg gca cat ggt ttt<br>Glu Met Glu Lys Gly Asn Leu Ile Ser Leu Trp Met Ala His Gly Phe<br>420　　　　　　　　425　　　　　　　　430 | 1767 |
| att tta tcg aaa gga aac ttg gag cta gag aat gta ggt aat gaa gta<br>Ile Leu Ser Lys Gly Asn Leu Glu Leu Glu Asn Val Gly Asn Glu Val | 1815 |

```
              435                 440                 445
tgg aat gaa tta tac ttg agg tct ttc ttc caa gag att gaa gtt aaa    1863
Trp Asn Glu Leu Tyr Leu Arg Ser Phe Phe Gln Glu Ile Glu Val Lys
450                 455                 460                 465 tct ggt caa act tat ttc aag atg cat gat ctc att cat gat ctg gca    1911
Ser Gly Gln Thr Tyr Phe Lys Met His Asp Leu Ile His Asp Leu Ala
                470                 475                 480 aca tct cta ttt tcg gca agc aca tca agc agc aat atc cga gaa ata    1959
Thr Ser Leu Phe Ser Ala Ser Thr Ser Ser Ser Asn Ile Arg Glu Ile
                    485                 490                 495 att gta gaa aat tac ata cat atg atg tcc att ggt ttc act aaa gtg    2007
Ile Val Glu Asn Tyr Ile His Met Met Ser Ile Gly Phe Thr Lys Val
                500                 505                 510 gta tct tct tac tct ctt tcc cac ttg cag aag ttt gtc tcg ttg agg    2055
Val Ser Ser Tyr Ser Leu Ser His Leu Gln Lys Phe Val Ser Leu Arg
    515                 520                 525 gtg ctt aat cta agt gac ata aaa ctt aag cag tta ccg tct tcc att    2103
Val Leu Asn Leu Ser Asp Ile Lys Leu Lys Gln Leu Pro Ser Ser Ile
530                 535                 540                 545 gga gat cta gta cat tta aga tac cta aac ttg tct ggc aat act agt    2151
Gly Asp Leu Val His Leu Arg Tyr Leu Asn Leu Ser Gly Asn Thr Ser
                550                 555                 560 att cgt agt ctt cca aac cag tta tgc aag ctt caa aat ctg cag act    2199
Ile Arg Ser Leu Pro Asn Gln Leu Cys Lys Leu Gln Asn Leu Gln Thr
                    565                 570                 575 ctt gat cta cat ggc tgt cat tca ctt tgt tgt ttg cca aaa gaa aca    2247
Leu Asp Leu His Gly Cys His Ser Leu Cys Cys Leu Pro Lys Glu Thr
                580                 585                 590 agc aaa ctt ggt agt ctt cga aat ctt tta ctt gat ggt tgc tat gga    2295
Ser Lys Leu Gly Ser Leu Arg Asn Leu Leu Leu Asp Gly Cys Tyr Gly
    595                 600                 605 ttg act tgt atg cca cca agg ata gga tct ttg aca tgc ctt aag act    2343
Leu Thr Cys Met Pro Pro Arg Ile Gly Ser Leu Thr Cys Leu Lys Thr
610                 615                 620                 625 cta agt aga ttt gtg gtg gga att cag aag aaa agt tgt caa ctt ggt    2391
Leu Ser Arg Phe Val Val Gly Ile Gln Lys Lys Ser Cys Gln Leu Gly
                630                 635                 640 gaa tta cga aac ctg aat ctc tat ggc tca att gaa atc acg cat ctt    2439
Glu Leu Arg Asn Leu Asn Leu Tyr Gly Ser Ile Glu Ile Thr His Leu
                    645                 650                 655 gag aga gtg aag aat gat atg gat gca aaa gaa gcc aat tta tct gca    2487
Glu Arg Val Lys Asn Asp Met Asp Ala Lys Glu Ala Asn Leu Ser Ala
                660                 665                 670 aaa gaa aat ctg cat tct tta agc atg aaa tgg gat gac gat gaa cgt    2535
Lys Glu Asn Leu His Ser Leu Ser Met Lys Trp Asp Asp Asp Glu Arg
    675                 680                 685 cca cgt ata tat gaa tca gaa aaa gtt gaa gtg ctt gaa gct ctc aaa    2583
Pro Arg Ile Tyr Glu Ser Glu Lys Val Glu Val Leu Glu Ala Leu Lys
690                 695                 700                 705 cca cac tcc aat ctg act tgt tta aca atc agg ggc ttc aga gga atc    2631
Pro His Ser Asn Leu Thr Cys Leu Thr Ile Arg Gly Phe Arg Gly Ile
                710                 715                 720 cgt ctc cca gac tgg atg aat cac tca gtt ttg aaa aat gtt gtc tct    2679
Arg Leu Pro Asp Trp Met Asn His Ser Val Leu Lys Asn Val Val Ser
                    725                 730                 735 att gaa atc atc agt tgc aaa aac tgc tca tgc tta cca ccc ttt ggt    2727
Ile Glu Ile Ile Ser Cys Lys Asn Cys Ser Cys Leu Pro Pro Phe Gly
                740                 745                 750 gag ctg cct tgt cta aaa agt cta gag tta tgg agg ggg tct gcg gaa    2775
```

```
                Glu Leu Pro Cys Leu Lys Ser Leu Glu Leu Trp Arg Gly Ser Ala Glu
                    755                 760                 765 gtg gag tat gtt gat tct gga ttc cct aca aga aga agg ttt cca tct          2823
Val Glu Tyr Val Asp Ser Gly Phe Pro Thr Arg Arg Arg Phe Pro Ser
770                 775                 780                 785 ctg aga aaa ctt aat ata cgc gaa ttt gat aat ctg aaa gga ttg ctg          2871
Leu Arg Lys Leu Asn Ile Arg Glu Phe Asp Asn Leu Lys Gly Leu Leu
                790                 795                 800 aaa aag gaa gga gaa gag caa tgc cct gtg ctt gaa gag ata gag att          2919
Lys Lys Glu Gly Glu Glu Gln Cys Pro Val Leu Glu Glu Ile Glu Ile
            805                 810                 815 aaa tgt tgc cct atg ttt gtt att cca acc ctt tct tct gtc aag aaa          2967
Lys Cys Cys Pro Met Phe Val Ile Pro Thr Leu Ser Ser Val Lys Lys
        820                 825                 830 ttg gta gtt agt ggg gac aag tca gat gca ata ggt ttc agt tcc ata          3015
Leu Val Val Ser Gly Asp Lys Ser Asp Ala Ile Gly Phe Ser Ser Ile
    835                 840                 845 tct aat ctc atg gct ctt act tcc ctc caa att cgc tat aac aaa gaa          3063
Ser Asn Leu Met Ala Leu Thr Ser Leu Gln Ile Arg Tyr Asn Lys Glu
850                 855                 860                 865 gat gct tca ctc cca gaa gag atg ttc aaa agc ctt gca aat ctc aaa          3111
Asp Ala Ser Leu Pro Glu Glu Met Phe Lys Ser Leu Ala Asn Leu Lys
                870                 875                 880 tac ttg aat atc tct ttt tac ttc aat ctt aaa gag ctg cct acc agc          3159
Tyr Leu Asn Ile Ser Phe Tyr Phe Asn Leu Lys Glu Leu Pro Thr Ser
                885                 890                 895 ctg gct agt ctc aat gct ttg aag cat ctg gaa att cat agt tgt tat          3207
Leu Ala Ser Leu Asn Ala Leu Lys His Leu Glu Ile His Ser Cys Tyr
            900                 905                 910 gca cta gag agt ctc ccc gag gaa ggt gtg aaa ggt tta att tca ctc          3255
Ala Leu Glu Ser Leu Pro Glu Glu Gly Val Lys Gly Leu Ile Ser Leu
        915                 920                 925 aca cag tta tcc ata aca tac tgt gaa atg cta caa tgt tta ccg gag          3303
Thr Gln Leu Ser Ile Thr Tyr Cys Glu Met Leu Gln Cys Leu Pro Glu
930                 935                 940                 945 gga ttg cag cac cta aca gcc ctc aca aat tta tca gtt gag ttt tgt          3351
Gly Leu Gln His Leu Thr Ala Leu Thr Asn Leu Ser Val Glu Phe Cys
                950                 955                 960 cca aca ctg gcc aag cgg tgt gag aag gga ata gga gaa gac tgg tac          3399
Pro Thr Leu Ala Lys Arg Cys Glu Lys Gly Ile Gly Glu Asp Trp Tyr
                965                 970                 975 aaa att gct cac att cct cgt gtg ttt att tat tagtattccc aattagatgt        3452
Lys Ile Ala His Ile Pro Arg Val Phe Ile Tyr
            980                 985 aattttctga tttcttttg gaaacaaatc aactatttgt aagatctatt tgtattatac         3512 ttgattttc ttgggtctgt aacaataaat atttgaaatt tttcatatta agattcagaa         3572
ttagtcttat agctaacggt atc                                                3595

<210> SEQ ID NO 4
<211> LENGTH: 988
<212> TYPE: PRT
<213> ORGANISM: Solanum bulbocastanum

<400> SEQUENCE: 4

Met Ala Glu Ala Phe Leu Gln Val Leu Leu Asp Asn Leu Thr Cys Phe
1               5                   10                  15

Ile Gln Gly Glu Leu Gly Leu Ile Leu Gly Phe Lys Asp Glu Phe Glu
            20                  25                  30
```

-continued

```
Lys Leu Gln Ser Thr Phe Thr Thr Ile Gln Ala Val Leu Glu Asp Ala
            35                  40                  45
Gln Lys Lys Gln Leu Lys Asp Lys Ala Ile Glu Asn Trp Leu Gln Lys
        50                  55                  60
Leu Asn Ala Ala Ala Tyr Glu Ala Asp Asp Ile Leu Asp Glu Cys Lys
 65                  70                  75                  80
Thr Glu Ala Pro Ile Arg Gln Lys Lys Asn Lys Tyr Gly Cys Tyr His
                85                  90                  95
Pro Asn Val Ile Thr Phe Arg His Lys Ile Gly Lys Arg Met Lys Lys
            100                 105                 110
Ile Met Glu Lys Leu Asp Val Ile Ala Ala Glu Arg Ile Lys Phe His
            115                 120                 125
Leu Asp Glu Arg Thr Ile Glu Arg Gln Val Ala Thr Arg Gln Thr Gly
        130                 135                 140
Phe Val Leu Asn Glu Pro Gln Val Tyr Gly Arg Asp Lys Glu Lys Asp
145                 150                 155                 160
Glu Ile Val Lys Ile Leu Ile Asn Asn Val Ser Asn Ala Gln Thr Leu
                165                 170                 175
Pro Val Leu Pro Ile Leu Gly Met Gly Gly Leu Gly Lys Thr Thr Leu
            180                 185                 190
Ala Gln Met Val Phe Asn Asp Gln Arg Val Ile Glu His Phe His Pro
        195                 200                 205
Lys Ile Trp Ile Cys Val Ser Glu Asp Phe Asn Glu Lys Arg Leu Ile
        210                 215                 220
Lys Glu Ile Val Glu Ser Ile Glu Glu Lys Ser Leu Gly Gly Met Asp
225                 230                 235                 240
Leu Ala Pro Leu Gln Lys Lys Leu Arg Asp Leu Leu Asn Gly Lys Lys
                245                 250                 255
Tyr Leu Val Leu Asp Asp Val Trp Asn Glu Asp Gln Asp Lys Trp
            260                 265                 270
Ala Lys Leu Arg Gln Val Leu Lys Val Gly Ala Ser Gly Ala Ser Val
        275                 280                 285
Leu Thr Thr Thr Arg Leu Glu Lys Val Gly Ser Ile Met Gly Thr Leu
        290                 295                 300
Gln Pro Tyr Glu Leu Ser Asn Leu Ser Gln Glu Asp Cys Trp Leu Leu
305                 310                 315                 320
Phe Met Gln Arg Ala Phe Gly His Gln Glu Glu Ile Asn Leu Asn Leu
                325                 330                 335
Val Ala Ile Gly Lys Glu Ile Val Lys Lys Cys Gly Gly Val Pro Leu
            340                 345                 350
Ala Ala Lys Thr Leu Gly Gly Ile Leu Arg Phe Lys Arg Glu Glu Arg
        355                 360                 365
Gln Trp Glu His Val Arg Asp Ser Glu Ile Trp Lys Leu Pro Gln Glu
        370                 375                 380
Glu Ser Ser Ile Leu Pro Ala Leu Arg Leu Ser Tyr His His Leu Pro
385                 390                 395                 400
Leu Asp Leu Arg Gln Cys Phe Thr Tyr Cys Ala Val Phe Pro Lys Asp
                405                 410                 415
Thr Glu Met Glu Lys Gly Asn Leu Ile Ser Leu Trp Met Ala His Gly
            420                 425                 430
Phe Ile Leu Ser Lys Gly Asn Leu Glu Leu Glu Asn Val Gly Asn Glu
        435                 440                 445
Val Trp Asn Glu Leu Tyr Leu Arg Ser Phe Phe Gln Glu Ile Glu Val
```

-continued

```
            450                 455                 460
Lys Ser Gly Gln Thr Tyr Phe Lys Met His Asp Leu Ile His Asp Leu
465                 470                 475                 480

Ala Thr Ser Leu Phe Ser Ala Ser Thr Ser Ser Ser Asn Ile Arg Glu
                    485                 490                 495

Ile Ile Val Glu Asn Tyr Ile His Met Met Ser Ile Gly Phe Thr Lys
                500                 505                 510

Val Val Ser Ser Tyr Ser Leu Ser His Leu Gln Lys Phe Val Ser Leu
                515                 520                 525

Arg Val Leu Asn Leu Ser Asp Ile Lys Leu Lys Gln Leu Pro Ser Ser
530                 535                 540

Ile Gly Asp Leu Val His Leu Arg Tyr Leu Asn Leu Ser Gly Asn Thr
545                 550                 555                 560

Ser Ile Arg Ser Leu Pro Asn Gln Leu Cys Lys Leu Gln Asn Leu Gln
                565                 570                 575

Thr Leu Asp Leu His Gly Cys His Ser Leu Cys Cys Leu Pro Lys Glu
                580                 585                 590

Thr Ser Lys Leu Gly Ser Leu Arg Asn Leu Leu Leu Asp Gly Cys Tyr
                595                 600                 605

Gly Leu Thr Cys Met Pro Pro Arg Ile Gly Ser Leu Thr Cys Leu Lys
                610                 615                 620

Thr Leu Ser Arg Phe Val Val Gly Ile Gln Lys Lys Ser Cys Gln Leu
625                 630                 635                 640

Gly Glu Leu Arg Asn Leu Asn Leu Tyr Gly Ser Ile Glu Ile Thr His
                645                 650                 655

Leu Glu Arg Val Lys Asn Asp Met Asp Ala Lys Glu Ala Asn Leu Ser
                660                 665                 670

Ala Lys Glu Asn Leu His Ser Leu Ser Met Lys Trp Asp Asp Asp Glu
                675                 680                 685

Arg Pro Arg Ile Tyr Glu Ser Glu Lys Val Glu Val Leu Glu Ala Leu
                690                 695                 700

Lys Pro His Ser Asn Leu Thr Cys Leu Thr Ile Arg Gly Phe Arg Gly
705                 710                 715                 720

Ile Arg Leu Pro Asp Trp Met Asn His Ser Val Leu Lys Asn Val Val
                725                 730                 735

Ser Ile Glu Ile Ile Ser Cys Lys Asn Cys Ser Cys Leu Pro Pro Phe
                740                 745                 750

Gly Glu Leu Pro Cys Leu Lys Ser Leu Glu Leu Trp Arg Gly Ser Ala
                755                 760                 765

Glu Val Glu Tyr Val Asp Ser Gly Phe Pro Thr Arg Arg Arg Phe Pro
770                 775                 780

Ser Leu Arg Lys Leu Asn Ile Arg Glu Phe Asp Asn Leu Lys Gly Leu
785                 790                 795                 800

Leu Lys Lys Glu Gly Glu Glu Gln Cys Pro Val Leu Glu Glu Ile Glu
                805                 810                 815

Ile Lys Cys Cys Pro Met Phe Val Ile Pro Thr Leu Ser Ser Val Lys
                820                 825                 830

Lys Leu Val Val Ser Gly Asp Lys Ser Asp Ala Ile Gly Phe Ser Ser
                835                 840                 845

Ile Ser Asn Leu Met Ala Leu Thr Ser Leu Gln Ile Arg Tyr Asn Lys
850                 855                 860

Glu Asp Ala Ser Leu Pro Glu Glu Met Phe Lys Ser Leu Ala Asn Leu
865                 870                 875                 880
```

```
Lys Tyr Leu Asn Ile Ser Phe Tyr Phe Asn Leu Lys Glu Leu Pro Thr
                885                 890                 895
Ser Leu Ala Ser Leu Asn Ala Leu Lys His Leu Glu Ile His Ser Cys
                900                 905                 910
Tyr Ala Leu Glu Ser Leu Pro Glu Glu Gly Val Lys Gly Leu Ile Ser
                915                 920                 925
Leu Thr Gln Leu Ser Ile Thr Tyr Cys Glu Met Leu Gln Cys Leu Pro
                930                 935                 940
Glu Gly Leu Gln His Leu Thr Ala Leu Thr Asn Leu Ser Val Glu Phe
945                 950                 955                 960
Cys Pro Thr Leu Ala Lys Arg Cys Glu Lys Gly Ile Gly Glu Asp Trp
                965                 970                 975
Tyr Lys Ile Ala His Ile Pro Arg Val Phe Ile Tyr
                980                 985

<210> SEQ ID NO 5
<211> LENGTH: 3347
<212> TYPE: DNA
<213> ORGANISM: Solanum bulbocastanum
<220> FEATURE:
<221> NAME/KEY: CDS
<222> LOCATION: (57)..(509)
<220> FEATURE:
<221> NAME/KEY: Intron
<222> LOCATION: (510)..(788)
<220> FEATURE:
<221> NAME/KEY: CDS
<222> LOCATION: (789)..(3344)

<400> SEQUENCE: 5
ccaacatctt acttcatttc aaaaaatata gattcattgc ttcctcacaa tactct atg    59
                                                               Met
                                                                 1 gct gaa gct ttc ctt caa gtt ctg tta gac aat ctg act tgt ttc atc    107
Ala Glu Ala Phe Leu Gln Val Leu Leu Asp Asn Leu Thr Cys Phe Ile
              5                  10                  15 caa ggg gaa gtt gga ttg att ctt ggt ttt aag gat gag ttc gaa aag    155
Gln Gly Glu Val Gly Leu Ile Leu Gly Phe Lys Asp Glu Phe Glu Lys
         20                  25                  30 ctt caa agc aca ttt act aca atc caa gct gtg cta gaa gat gct cag    203
Leu Gln Ser Thr Phe Thr Thr Ile Gln Ala Val Leu Glu Asp Ala Gln
     35                  40                  45 aag aag caa ttg aag gac aag gca ata gaa aat tgg ttg cag aaa ctc    251
Lys Lys Gln Leu Lys Asp Lys Ala Ile Glu Asn Trp Leu Gln Lys Leu
 50                  55                  60                  65 aat gct gct gta tat gaa gct gac gac atc ttg gac gaa tgt aaa act    299
Asn Ala Ala Val Tyr Glu Ala Asp Asp Ile Leu Asp Glu Cys Lys Thr
                 70                  75                  80 gag gca cca att aga cag aag aag aac aaa tat ggg tgt tat cat cca    347
Glu Ala Pro Ile Arg Gln Lys Lys Asn Lys Tyr Gly Cys Tyr His Pro
             85                  90                  95 aac gtt atc gct ttc cgt cac aag att ggg aaa agg atg aaa aag att    395
Asn Val Ile Ala Phe Arg His Lys Ile Gly Lys Arg Met Lys Lys Ile
        100                 105                 110 atg gag aaa cta gat gta att gca gcg gaa cga att aag ttt cat ttg    443
Met Glu Lys Leu Asp Val Ile Ala Ala Glu Arg Ile Lys Phe His Leu
    115                 120                 125 gct gaa agg act aca gag aga caa gtt gct aca cgc caa aca ggt gct    491
Ala Glu Arg Thr Thr Glu Arg Gln Val Ala Thr Arg Gln Thr Gly Ala
130                 135                 140                 145
```

```
cat ctt aga tat ttt tct aaaaaaacag ctttatatca tgaaattcat          539
His Leu Arg Tyr Phe Ser
             150 gtgtgtttgg gattttttct aatctaaatg ttgtctcaag tctaagtaga taagtggatc  599 cagatttgga tatattaata tattatctaa atttgtttcg tgaaattttt aacagataaa  659 gcctgagttg ttttagacat tataaattaa caatgataat aatgtgaatt caaaaaagtg  719 cattatgtct gctgcttctc aagcttatca ttgtctcttt attgtgcaaa attcttcttc  779 gttttttg ctg act cct act gag ctt gga cca ggt ttt gtt tta aat gaa  830
         Leu Thr Pro Thr Glu Leu Gly Pro Gly Phe Val Leu Asn Glu
                      155                 160                 165 cca caa gtt tat gga aga gac aaa gaa aag gat gag ata gtg aaa atc   878
Pro Gln Val Tyr Gly Arg Asp Lys Glu Lys Asp Glu Ile Val Lys Ile
                170                 175                 180 ctg ata aac att gtt agc gat gcc caa aca ctt tca gtc ctc cca ata  926
Leu Ile Asn Ile Val Ser Asp Ala Gln Thr Leu Ser Val Leu Pro Ile
                185                 190                 195 ctt ggt atg ggg gga tta gga aag acg aca ctt gcc caa atg gtc ttc  974
Leu Gly Met Gly Gly Leu Gly Lys Thr Thr Leu Ala Gln Met Val Phe
            200                 205                 210 aat gat cag aga gta att gag cat ttc ctt ccc aaa ata tgg att tgt  1022
Asn Asp Gln Arg Val Ile Glu His Phe Leu Pro Lys Ile Trp Ile Cys
            215                 220                 225 gtc tcg gaa gat ttt aat gag aag agg ttg ata aag gaa att gta gaa  1070
Val Ser Glu Asp Phe Asn Glu Lys Arg Leu Ile Lys Glu Ile Val Glu
230                 235                 240                 245 tct att gaa gaa aag tca ctt ggt gac atg gac ttg gct cca ctt caa  1118
Ser Ile Glu Glu Lys Ser Leu Gly Asp Met Asp Leu Ala Pro Leu Gln
                250                 255                 260 aag aag ctt cag gac ttg ctg aat gga aaa aaa tat ttg ctt gtc tta  1166
Lys Lys Leu Gln Asp Leu Leu Asn Gly Lys Lys Tyr Leu Leu Val Leu
                265                 270                 275 gat gat att tgg aat gaa gat caa gat aag tgg gct aag tta cga gaa  1214
Asp Asp Ile Trp Asn Glu Asp Gln Asp Lys Trp Ala Lys Leu Arg Glu
            280                 285                 290 gtg ttg aag gtt gga gca agt ggt gct tct atc cta acc act act cgt  1262
Val Leu Lys Val Gly Ala Ser Gly Ala Ser Ile Leu Thr Thr Thr Arg
295                 300                 305 ctt gaa aag gtt gga tca att atg caa act ttg caa cca tat gaa ttg  1310
Leu Glu Lys Val Gly Ser Ile Met Gln Thr Leu Gln Pro Tyr Glu Leu
310                 315                 320                 325 tca aac ttg tgt caa gaa gat tgc tgg ttg ttg ttc atg caa cgt gca  1358
Ser Asn Leu Cys Gln Glu Asp Cys Trp Leu Leu Phe Met Gln Arg Ala
                330                 335                 340 ttt ggg cac caa gaa gaa ata aat cat aat ctt gtg gct atc gga aag  1406
Phe Gly His Gln Glu Glu Ile Asn His Asn Leu Val Ala Ile Gly Lys
            345                 350                 355 gag ata gtg aaa aaa tgt ggt ggt gtg cct cta gca gct aaa act ctt  1454
Glu Ile Val Lys Lys Cys Gly Gly Val Pro Leu Ala Ala Lys Thr Leu
            360                 365                 370 gga ggt att ttg cga ttc aag aga caa gaa aga cag tgg gaa cat gtg  1502
Gly Gly Ile Leu Arg Phe Lys Arg Gln Glu Arg Gln Trp Glu His Val
            375                 380                 385 aga gat agt gag att tgg aaa ttg cct caa gaa gaa agt tct att ctg  1550
Arg Asp Ser Glu Ile Trp Lys Leu Pro Gln Glu Glu Ser Ser Ile Leu
390                 395                 400                 405 ccg gcc ctg aaa ctt agt tac cat cat ctt cca ctt gat ttg aga caa  1598
Pro Ala Leu Lys Leu Ser Tyr His His Leu Pro Leu Asp Leu Arg Gln
```

-continued

```
              410                 415                 420
tgc ttt tca tat tgt gca gta ttc cca aag gat acc aaa atg gaa aag    1646
Cys Phe Ser Tyr Cys Ala Val Phe Pro Lys Asp Thr Lys Met Glu Lys
            425                 430                 435 gaa aat cta atc tct ctc tgg atg gca cat ggt ttt ctt tta tcg aaa    1694
Glu Asn Leu Ile Ser Leu Trp Met Ala His Gly Phe Leu Leu Ser Lys
            440                 445                 450 gga aac ttg gag cta gag gat gta ggt aat gaa gta tgg aat gaa tta    1742
Gly Asn Leu Glu Leu Glu Asp Val Gly Asn Glu Val Trp Asn Glu Leu
        455                 460                 465 tac ttg agg tct ttc ttc caa gag att gaa gtt aca tat ggt aaa act    1790
Tyr Leu Arg Ser Phe Phe Gln Glu Ile Glu Val Thr Tyr Gly Lys Thr
470                 475                 480                 485 tat ttc aag atg cat gat ctc atc cat gat ttg gct aca tct cta ttt    1838
Tyr Phe Lys Met His Asp Leu Ile His Asp Leu Ala Thr Ser Leu Phe
                490                 495                 500 tcg gca agc gca tca agc aac aat atc cgt gaa ata aat gta aaa ggt    1886
Ser Ala Ser Ala Ser Ser Asn Asn Ile Arg Glu Ile Asn Val Lys Gly
            505                 510                 515 tac cca cat atg atg tcg att ggc ttt gca aaa gtg gtg tct ttt tac    1934
Tyr Pro His Met Met Ser Ile Gly Phe Ala Lys Val Val Ser Phe Tyr
        520                 525                 530 tct cgt tct cac ttc caa aag ttt gtc tcg tta agg gtg ctt aat cta    1982
Ser Arg Ser His Phe Gln Lys Phe Val Ser Leu Arg Val Leu Asn Leu
535                 540                 545 agt aac tta gaa ctc aag cag tta cca tct tca att ggg gat cta gta    2030
Ser Asn Leu Glu Leu Lys Gln Leu Pro Ser Ser Ile Gly Asp Leu Val
550                 555                 560                 565 cat tta aga tac cta aac ttg tct gac aat aat aga att cgt agt ctt    2078
His Leu Arg Tyr Leu Asn Leu Ser Asp Asn Asn Arg Ile Arg Ser Leu
                570                 575                 580 ccc aag cag tta tgc aag ctt caa aat ctg cag act ctt gat cta cgt    2126
Pro Lys Gln Leu Cys Lys Leu Gln Asn Leu Gln Thr Leu Asp Leu Arg
            585                 590                 595 tgt tgc tac aga ctt tct tgt ttg cca aaa gaa aca agc aaa ctt ggt    2174
Cys Cys Tyr Arg Leu Ser Cys Leu Pro Lys Glu Thr Ser Lys Leu Gly
        600                 605                 610 agt ctc cga aat ctt tta ctt gat cgt tgc cat gga ttg act tgt atg    2222
Ser Leu Arg Asn Leu Leu Leu Asp Arg Cys His Gly Leu Thr Cys Met
615                 620                 625 cca cca agg ata gga tca ttg aca tgc ctt aag act cta gat cgc ttt    2270
Pro Pro Arg Ile Gly Ser Leu Thr Cys Leu Lys Thr Leu Asp Arg Phe
630                 635                 640                 645 gca atg gga agg gag aaa agt cct caa att ggt gaa tta cga aac ctg    2318
Ala Met Gly Arg Glu Lys Ser Pro Gln Ile Gly Glu Leu Arg Asn Leu
                650                 655                 660 aat ctc tat ggc tca att tca atc acg cat ctt gag aga gtg aag aat    2366
Asn Leu Tyr Gly Ser Ile Ser Ile Thr His Leu Glu Arg Val Lys Asn
            665                 670                 675 gat atg gat gca aaa gaa gcc aat tta tct tca aaa gaa aat ctg cat    2414
Asp Met Asp Ala Lys Glu Ala Asn Leu Ser Ser Lys Glu Asn Leu His
        680                 685                 690 tct tta agt atg ata tgg gat gaa gat gaa cgt cca cat aga tat gaa    2462
Ser Leu Ser Met Ile Trp Asp Glu Asp Glu Arg Pro His Arg Tyr Glu
695                 700                 705 tca gaa gat gtt gaa gtg ctt gaa gcc ctc aaa cca cac tcc aat ctg    2510
Ser Glu Asp Val Glu Val Leu Glu Ala Leu Lys Pro His Ser Asn Leu
710                 715                 720                 725 act tgt tta aca att att ggc ttc aga gga atc cgt ctc cca gac tgg    2558
```

```
                                          -continued

Thr Cys Leu Thr Ile Ile Gly Phe Arg Gly Ile Arg Leu Pro Asp Trp
                730                 735                 740 atg aat cac tca gtt ttg aaa aat gtt gtc tct ctt gaa atc agc gat       2606
Met Asn His Ser Val Leu Lys Asn Val Val Ser Leu Glu Ile Ser Asp
            745                 750                 755 tgc aaa aac tgc tca tgc tta cca ccc ttt ggt gaa ctg cct tgt cta       2654
Cys Lys Asn Cys Ser Cys Leu Pro Pro Phe Gly Glu Leu Pro Cys Leu
        760                 765                 770 aat agt cta cag tta tgg agt ggg tct gca gaa gtg gag tat att gat       2702
Asn Ser Leu Gln Leu Trp Ser Gly Ser Ala Glu Val Glu Tyr Ile Asp
    775                 780                 785 tct gga ttc cct aca aga aga agg ttt cca tct ctg aga aaa ctt att       2750
Ser Gly Phe Pro Thr Arg Arg Arg Phe Pro Ser Leu Arg Lys Leu Ile
790                 795                 800                 805 ata ggc gaa ttt gat aat ctg aaa gga ttg gtg aaa aag gaa gga gaa       2798
Ile Gly Glu Phe Asp Asn Leu Lys Gly Leu Val Lys Lys Glu Gly Glu
                810                 815                 820 gag caa ttc cct gtg ctt gaa gag atg gag att aac tgg tgc cct atg       2846
Glu Gln Phe Pro Val Leu Glu Glu Met Glu Ile Asn Trp Cys Pro Met
            825                 830                 835 ttt gtt att ccg acc ctt tct tct gtc aac aaa ttg gta gtt agt ggg       2894
Phe Val Ile Pro Thr Leu Ser Ser Val Asn Lys Leu Val Val Ser Gly
        840                 845                 850 gaa gag tca gat gca ata ggc ttc agt tcc ata tct aat ctc agg gct       2942
Glu Glu Ser Asp Ala Ile Gly Phe Ser Ser Ile Ser Asn Leu Arg Ala
    855                 860                 865 ctt act tct ctc aat att agc tat aac tct gaa gct act tca ctc cca       2990
Leu Thr Ser Leu Asn Ile Ser Tyr Asn Ser Glu Ala Thr Ser Leu Pro
870                 875                 880                 885 gaa gag atg ttc aaa agc ctt gca aat cta aaa tac ttg aat atc tat       3038
Glu Glu Met Phe Lys Ser Leu Ala Asn Leu Lys Tyr Leu Asn Ile Tyr
                890                 895                 900 tac ttc aag aat ctc aaa gag ctg cct acc aac ctg gct agt ctt aat       3086
Tyr Phe Lys Asn Leu Lys Glu Leu Pro Thr Asn Leu Ala Ser Leu Asn
            905                 910                 915 gct ttg aag aat ctg gaa att gaa agt tgt tat gca cta gag agt ctc       3134
Ala Leu Lys Asn Leu Glu Ile Glu Ser Cys Tyr Ala Leu Glu Ser Leu
        920                 925                 930 ccc gag gaa ggt gtg aaa ggt tta act tca ctt aca caa tta tcc ata       3182
Pro Glu Glu Gly Val Lys Gly Leu Thr Ser Leu Thr Gln Leu Ser Ile
    935                 940                 945 aca tac tgc acg atg cta caa tgt tta tcg gag gga ttg cag cac cta       3230
Thr Tyr Cys Thr Met Leu Gln Cys Leu Ser Glu Gly Leu Gln His Leu
950                 955                 960                 965 aca gcc ctc aca aat tta tca gtt agg gat tgt cca aca ctg gcc aag       3278
Thr Ala Leu Thr Asn Leu Ser Val Arg Asp Cys Pro Thr Leu Ala Lys
                970                 975                 980 cga tgt gag aag gga ata gga gaa gac tgg tac aaa att gct cac att       3326
Arg Cys Glu Lys Gly Ile Gly Glu Asp Trp Tyr Lys Ile Ala His Ile
            985                 990                 995 cct gat gtg  ttt atc cgt taa                                          3347
Pro Asp Val  Phe Ile Arg
        1000

<210> SEQ ID NO 6
<211> LENGTH: 1003
<212> TYPE: PRT
<213> ORGANISM: Solanum bulbocastanum

<400> SEQUENCE: 6
```

-continued

```
Met Ala Glu Ala Phe Leu Gln Val Leu Leu Asp Asn Leu Thr Cys Phe
1               5                   10                  15

Ile Gln Gly Glu Val Gly Leu Ile Leu Gly Phe Lys Asp Glu Phe Glu
            20                  25                  30

Lys Leu Gln Ser Thr Phe Thr Thr Ile Gln Ala Val Leu Glu Asp Ala
        35                  40                  45

Gln Lys Lys Gln Leu Lys Asp Lys Ala Ile Glu Asn Trp Leu Gln Lys
    50                  55                  60

Leu Asn Ala Ala Val Tyr Glu Ala Asp Asp Ile Leu Asp Glu Cys Lys
65              70                  75                  80

Thr Glu Ala Pro Ile Arg Gln Lys Lys Asn Lys Tyr Gly Cys Tyr His
                85                  90                  95

Pro Asn Val Ile Ala Phe Arg His Lys Ile Gly Lys Arg Met Lys Lys
            100                 105                 110

Ile Met Glu Lys Leu Asp Val Ile Ala Ala Glu Arg Ile Lys Phe His
        115                 120                 125

Leu Ala Glu Arg Thr Thr Glu Arg Gln Val Ala Thr Arg Gln Thr Gly
    130                 135                 140

Ala His Leu Arg Tyr Phe Ser Leu Thr Pro Thr Glu Leu Gly Pro Gly
145                 150                 155                 160

Phe Val Leu Asn Glu Pro Gln Val Tyr Gly Arg Asp Lys Glu Lys Asp
                165                 170                 175

Glu Ile Val Lys Ile Leu Ile Asn Ile Val Ser Asp Ala Gln Thr Leu
            180                 185                 190

Ser Val Leu Pro Ile Leu Gly Met Gly Gly Leu Gly Lys Thr Thr Leu
    195                 200                 205

Ala Gln Met Val Phe Asn Asp Gln Arg Val Ile Glu His Phe Leu Pro
210                 215                 220

Lys Ile Trp Ile Cys Val Ser Glu Asp Phe Asn Glu Lys Arg Leu Ile
225                 230                 235                 240

Lys Glu Ile Val Glu Ser Ile Glu Glu Lys Ser Leu Gly Asp Met Asp
                245                 250                 255

Leu Ala Pro Leu Gln Lys Lys Leu Gln Asp Leu Leu Asn Gly Lys Lys
            260                 265                 270

Tyr Leu Leu Val Leu Asp Asp Ile Trp Asn Glu Asp Gln Asp Lys Trp
    275                 280                 285

Ala Lys Leu Arg Glu Val Leu Lys Val Gly Ala Ser Gly Ala Ser Ile
290                 295                 300

Leu Thr Thr Thr Arg Leu Glu Lys Val Gly Ser Ile Met Gln Thr Leu
305                 310                 315                 320

Gln Pro Tyr Glu Leu Ser Asn Leu Cys Gln Glu Asp Cys Trp Leu Leu
                325                 330                 335

Phe Met Gln Arg Ala Phe Gly His Gln Glu Ile Asn His Asn Leu
            340                 345                 350

Val Ala Ile Gly Lys Glu Ile Val Lys Cys Gly Gly Val Pro Leu
    355                 360                 365

Ala Ala Lys Thr Leu Gly Gly Ile Leu Arg Phe Lys Arg Gln Glu Arg
370                 375                 380

Gln Trp Glu His Val Arg Asp Ser Glu Ile Trp Lys Leu Pro Gln Glu
385                 390                 395                 400

Glu Ser Ser Ile Leu Pro Ala Leu Lys Leu Ser Tyr His His Leu Pro
                405                 410                 415

Leu Asp Leu Arg Gln Cys Phe Ser Tyr Cys Ala Val Phe Pro Lys Asp
```

-continued

```
                420                 425                 430
Thr Lys Met Glu Lys Glu Asn Leu Ile Ser Leu Trp Met Ala His Gly
        435                 440                 445
Phe Leu Leu Ser Lys Gly Asn Leu Glu Leu Glu Asp Val Gly Asn Glu
    450                 455                 460
Val Trp Asn Glu Leu Tyr Leu Arg Ser Phe Phe Gln Glu Ile Glu Val
465                 470                 475                 480
Thr Tyr Gly Lys Thr Tyr Phe Lys Met His Asp Leu Ile His Asp Leu
                485                 490                 495
Ala Thr Ser Leu Phe Ser Ala Ser Ala Ser Ser Asn Asn Ile Arg Glu
            500                 505                 510
Ile Asn Val Lys Gly Tyr Pro His Met Met Ser Ile Gly Phe Ala Lys
        515                 520                 525
Val Val Ser Phe Tyr Ser Arg Ser His Phe Gln Lys Phe Val Ser Leu
    530                 535                 540
Arg Val Leu Asn Leu Ser Asn Leu Glu Leu Lys Gln Leu Pro Ser Ser
545                 550                 555                 560
Ile Gly Asp Leu Val His Leu Arg Tyr Leu Asn Leu Ser Asp Asn Asn
                565                 570                 575
Arg Ile Arg Ser Leu Pro Lys Gln Leu Cys Lys Leu Gln Asn Leu Gln
            580                 585                 590
Thr Leu Asp Leu Arg Cys Cys Tyr Arg Leu Ser Cys Leu Pro Lys Glu
        595                 600                 605
Thr Ser Lys Leu Gly Ser Leu Arg Asn Leu Leu Asp Arg Cys His
    610                 615                 620
Gly Leu Thr Cys Met Pro Pro Arg Ile Gly Ser Leu Thr Cys Leu Lys
625                 630                 635                 640
Thr Leu Asp Arg Phe Ala Met Gly Arg Glu Lys Ser Pro Gln Ile Gly
                645                 650                 655
Glu Leu Arg Asn Leu Asn Leu Tyr Gly Ser Ile Ser Ile Thr His Leu
            660                 665                 670
Glu Arg Val Lys Asn Asp Met Asp Ala Lys Glu Ala Asn Leu Ser Ser
        675                 680                 685
Lys Glu Asn Leu His Ser Leu Ser Met Ile Trp Asp Glu Asp Glu Arg
    690                 695                 700
Pro His Arg Tyr Glu Ser Glu Asp Val Glu Val Leu Glu Ala Leu Lys
705                 710                 715                 720
Pro His Ser Asn Leu Thr Cys Leu Thr Ile Ile Gly Phe Arg Gly Ile
                725                 730                 735
Arg Leu Pro Asp Trp Met Asn His Ser Val Leu Lys Asn Val Val Ser
            740                 745                 750
Leu Glu Ile Ser Asp Cys Lys Asn Cys Ser Cys Leu Pro Pro Phe Gly
        755                 760                 765
Glu Leu Pro Cys Leu Asn Ser Leu Gln Leu Trp Ser Gly Ser Ala Glu
    770                 775                 780
Val Glu Tyr Ile Asp Ser Gly Phe Pro Thr Arg Arg Arg Phe Pro Ser
785                 790                 795                 800
Leu Arg Lys Leu Ile Ile Gly Glu Phe Asp Asn Leu Lys Gly Leu Val
                805                 810                 815
Lys Lys Glu Gly Glu Glu Gln Phe Pro Val Leu Glu Glu Met Glu Ile
            820                 825                 830
Asn Trp Cys Pro Met Phe Val Ile Pro Thr Leu Ser Ser Val Asn Lys
        835                 840                 845
```

```
Leu Val Val Ser Gly Glu Glu Ser Asp Ala Ile Gly Phe Ser Ser Ile
    850             855                 860

Ser Asn Leu Arg Ala Leu Thr Ser Leu Asn Ile Ser Tyr Asn Ser Glu
865             870                 875                 880

Ala Thr Ser Leu Pro Glu Glu Met Phe Lys Ser Leu Ala Asn Leu Lys
            885                 890                 895

Tyr Leu Asn Ile Tyr Tyr Phe Lys Asn Leu Lys Glu Leu Pro Thr Asn
                900                 905                 910

Leu Ala Ser Leu Asn Ala Leu Lys Asn Leu Glu Ile Glu Ser Cys Tyr
            915                 920                 925

Ala Leu Glu Ser Leu Pro Glu Glu Gly Val Lys Gly Leu Thr Ser Leu
        930                 935                 940

Thr Gln Leu Ser Ile Thr Tyr Cys Thr Met Leu Gln Cys Leu Ser Glu
945                 950                 955                 960

Gly Leu Gln His Leu Thr Ala Leu Thr Asn Leu Ser Val Arg Asp Cys
                965                 970                 975

Pro Thr Leu Ala Lys Arg Cys Glu Lys Gly Ile Gly Glu Asp Trp Tyr
            980                 985                 990

Lys Ile Ala His Ile Pro Asp Val  Phe Ile Arg
            995                 1000

<210> SEQ ID NO 7
<211> LENGTH: 3222
<212> TYPE: DNA
<213> ORGANISM: Solanum Bulbocastanum
<220> FEATURE:
<221> NAME/KEY: CDS
<222> LOCATION: (58)..(528)
<220> FEATURE:
<221> NAME/KEY: Intron
<222> LOCATION: (529)..(690)
<220> FEATURE:
<221> NAME/KEY: CDS
<222> LOCATION: (691)..(3219)

<400> SEQUENCE: 7
aaatcagtca cttttaatctg tttcaattaa cttttgtgtt acagtgaatt ccaacat          57 atg gct gaa gct ttc ctt caa gtt ctg cta ggc aat atc act tct ttc        105
Met Ala Glu Ala Phe Leu Gln Val Leu Leu Gly Asn Ile Thr Ser Phe
1               5                   10                  15 atc caa ggg gaa ctt gta ttg ctt ttc ggt ttt gaa aac gac ttc aga        153
Ile Gln Gly Glu Leu Val Leu Leu Phe Gly Phe Glu Asn Asp Phe Arg
                20                  25                  30 aag ctt tca agc aca ttt tct acg atc caa ctt gtg ctt gaa gat gct        201
Lys Leu Ser Ser Thr Phe Ser Thr Ile Gln Leu Val Leu Glu Asp Ala
            35                  40                  45 tca gag aag caa ctg aag gac aag gca ata gag aat tgg ttg cag aaa        249
Ser Glu Lys Gln Leu Lys Asp Lys Ala Ile Glu Asn Trp Leu Gln Lys
        50                  55                  60 ctc aat ttt gct gca tat gaa gtc gat gac atc ttg gat gaa tgt aaa        297
Leu Asn Phe Ala Ala Tyr Glu Val Asp Asp Ile Leu Asp Glu Cys Lys
65                  70                  75                  80 aat gag gca gca aga ttc aat cag tcc tta tta ggg tat att cat cca        345
Asn Glu Ala Ala Arg Phe Asn Gln Ser Leu Leu Gly Tyr Ile His Pro
                85                  90                  95 aag atc atc att ttt cgt tac aag ctc gga aaa aga atg aaa aga atg        393
Lys Ile Ile Ile Phe Arg Tyr Lys Leu Gly Lys Arg Met Lys Arg Met
                100                 105                 110 atg gag aaa cta gat gca att gct gac gaa aga agg aag ttt cat ttg        441
```

```
                                              -continued

Met Glu Lys Leu Asp Ala Ile Ala Asp Glu Arg Arg Lys Phe His Leu
        115                 120                 125 cgt gca aag att gtc gag aaa caa gct tct aaa cgt gaa aca ggt gct        489
Arg Ala Lys Ile Val Glu Lys Gln Ala Ser Lys Arg Glu Thr Gly Ala
    130                 135                 140 cat ctt aaa ctg tgt tta gcc aag tac tta cta ata gct tagtttata          538
His Leu Lys Leu Cys Leu Ala Lys Tyr Leu Leu Ile Ala
145                 150                 155 ttcatctttt tgtagttacc agattctata catgtttgtt ccatgtcagc ccttccttgt      598 gtcttttgt tttgcaaaaa tcttctatta ttcctgctga ctccttttag tgagcttgaa       658
tttaataaaa tttgtgttcg cattgcttgt ga aca ggt ttt gtt tta gca gag        711
                                 Thr Gly Phe Val Leu Ala Glu
                                         160 cca aaa gtt tat gga agg gac aaa gag aag gat gag atg gtg aaa atc        759
Pro Lys Val Tyr Gly Arg Asp Lys Glu Lys Asp Glu Met Val Lys Ile
165                 170                 175                 180 ttg ata aac agt gtt agt aat gcc caa gaa cta tta gtg ctc cca ata        807
Leu Ile Asn Ser Val Ser Asn Ala Gln Glu Leu Leu Val Leu Pro Ile
                185                 190                 195 ctt ggt atg ggg gga cta gga aag aca aca ctt gcc caa atg att ttt        855
Leu Gly Met Gly Gly Leu Gly Lys Thr Thr Leu Ala Gln Met Ile Phe
            200                 205                 210 aat gat cag agc gtg act gca cat ttc aat cta aag ata tgg gtt tgt        903
Asn Asp Gln Ser Val Thr Ala His Phe Asn Leu Lys Ile Trp Val Cys
        215                 220                 225 gtc tca gat gat ttt gat gag aag agg ttg ata aag gca att gta gaa        951
Val Ser Asp Asp Phe Asp Glu Lys Arg Leu Ile Lys Ala Ile Val Glu
    230                 235                 240 tct att gaa aga agg cca ctt ggt gac ata gac ttg gct ccc ctc cag        999
Ser Ile Glu Arg Arg Pro Leu Gly Asp Ile Asp Leu Ala Pro Leu Gln
245                 250                 255                 260 aag aag ctt cag gag ttg ttg aat gga aaa aga tac ttt ctt gtt tta       1047
Lys Lys Leu Gln Glu Leu Leu Asn Gly Lys Arg Tyr Phe Leu Val Leu
                265                 270                 275 gat gat gtt tgg aat gaa gat caa gaa aag tgg gct aag ata aaa gca       1095
Asp Asp Val Trp Asn Glu Asp Gln Glu Lys Trp Ala Lys Ile Lys Ala
            280                 285                 290 gtc tta aag gtt gga gca caa ggt tct tct att cta gcc act act cgt       1143
Val Leu Lys Val Gly Ala Gln Gly Ser Ser Ile Leu Ala Thr Thr Arg
        295                 300                 305 ctt gaa agg gtc gga tca att atg gga act tgg caa cca tat cag tta       1191
Leu Glu Arg Val Gly Ser Ile Met Gly Thr Trp Gln Pro Tyr Gln Leu
    310                 315                 320 tca att ttg tct cca gaa tat tgt tgg ttg ttg ttc aag caa cgt gca       1239
Ser Ile Leu Ser Pro Glu Tyr Cys Trp Leu Leu Phe Lys Gln Arg Ala
325                 330                 335                 340 ttt ggc cac caa acg gaa aca aat cct gcc ctt gtg ggg att gga aaa       1287
Phe Gly His Gln Thr Glu Thr Asn Pro Ala Leu Val Gly Ile Gly Lys
                345                 350                 355 gag att gtg aag aaa tgt ggg ggt gtg cct cta gca gcc aag act ctt       1335
Glu Ile Val Lys Lys Cys Gly Gly Val Pro Leu Ala Ala Lys Thr Leu
            360                 365                 370 gga ggt ctt tta cgc ttc aag aga gaa gaa agt gaa tgg gaa cat gtg       1383
Gly Gly Leu Leu Arg Phe Lys Arg Glu Glu Ser Glu Trp Glu His Val
        375                 380                 385 aaa gat agt gag att tgg aat tta cct caa gat gaa aat tct gtt ttg       1431
Lys Asp Ser Glu Ile Trp Asn Leu Pro Gln Asp Glu Asn Ser Val Leu
    390                 395                 400
```

```
cct tcc ctg agg ctg agt tat cat cac ctt cca ctt aat ttg aga caa    1479
Pro Ser Leu Arg Leu Ser Tyr His His Leu Pro Leu Asn Leu Arg Gln
405                 410                 415                 420 tgt ttt gca tat tgt gcg gta ttc cca aag gac acc aaa ata gaa aag    1527
Cys Phe Ala Tyr Cys Ala Val Phe Pro Lys Asp Thr Lys Ile Glu Lys
            425                 430                 435 gaa tat ctc atc act ctc tgg atg gca cat ggt ttt ctt tta tca aaa   1575
Glu Tyr Leu Ile Thr Leu Trp Met Ala His Gly Phe Leu Leu Ser Lys
                440                 445                 450 gaa aat tca gag cta gag gat gtg ggt aat gaa gta tgg aaa gaa tta   1623
Glu Asn Ser Glu Leu Glu Asp Val Gly Asn Glu Val Trp Lys Glu Leu
            455                 460                 465 tac ttg agg tct ttc ttc caa gag gtc gaa gaa tat aaa ttt ggt aat   1671
Tyr Leu Arg Ser Phe Phe Gln Glu Val Glu Glu Tyr Lys Phe Gly Asn
        470                 475                 480 act tat ttc aag atg cat gat ctc atc cac gat ttg gct aca tct ctg   1719
Thr Tyr Phe Lys Met His Asp Leu Ile His Asp Leu Ala Thr Ser Leu
485                 490                 495                 500 ttc tca aca aac aca agg agc agc aaa att cgt caa ata aga gta gca   1767
Phe Ser Thr Asn Thr Arg Ser Ser Lys Ile Arg Gln Ile Arg Val Ala
                505                 510                 515 cag aaa aat aca att cct att ggt ttt gct gaa gtg gtg cct tct tat   1815
Gln Lys Asn Thr Ile Pro Ile Gly Phe Ala Glu Val Val Pro Ser Tyr
            520                 525                 530 tct cct tta atc ttt aaa agg ttt gtc tcg cta agg gtt ctt gat atg   1863
Ser Pro Leu Ile Phe Lys Arg Phe Val Ser Leu Arg Val Leu Asp Met
        535                 540                 545 aaa ttt tca aag ttt gat cag tta tca tct tcc atc gga gat cta ata   1911
Lys Phe Ser Lys Phe Asp Gln Leu Ser Ser Ser Ile Gly Asp Leu Ile
550                 555                 560 cat tta agg ttg ttg aac ttg cgt ggc agt agc att cgt agc ctt cca   1959
His Leu Arg Leu Leu Asn Leu Arg Gly Ser Ser Ile Arg Ser Leu Pro
565                 570                 575                 580 aag agg tta tgc aag ctt caa aat ctg cag aca ctt gat ata tca tgt   2007
Lys Arg Leu Cys Lys Leu Gln Asn Leu Gln Thr Leu Asp Ile Ser Cys
                585                 590                 595 tgt ttc tca ctt tct tat att cca aaa caa ata agt aaa tta agt agt   2055
Cys Phe Ser Leu Ser Tyr Ile Pro Lys Gln Ile Ser Lys Leu Ser Ser
            600                 605                 610 ctt aga aat ctt gtg ttc agt ggt tgt caa ata act tct atg cca cca   2103
Leu Arg Asn Leu Val Phe Ser Gly Cys Gln Ile Thr Ser Met Pro Pro
        615                 620                 625 aga ata gga tca ttg aca tgc ctt aag act cta gat tac ttt att gtc   2151
Arg Ile Gly Ser Leu Thr Cys Leu Lys Thr Leu Asp Tyr Phe Ile Val
630                 635                 640 ggc gag agg aaa ggt tat caa ctt ggt gaa cta cgg aat cta agc cta   2199
Gly Glu Arg Lys Gly Tyr Gln Leu Gly Glu Leu Arg Asn Leu Ser Leu
645                 650                 655                 660 cat ggt tca ctt tca atc tca cat ctt gag aga gtg aag agt gaa acg   2247
His Gly Ser Leu Ser Ile Ser His Leu Glu Arg Val Lys Ser Glu Thr
                665                 670                 675 gat gca aaa gaa gct aat tta tct acc aaa caa aaa ttg tac aat tta   2295
Asp Ala Lys Glu Ala Asn Leu Ser Thr Lys Gln Lys Leu Tyr Asn Leu
            680                 685                 690 tgc atg agt tgg gat att agg cca tat gga tat gaa tca gaa aac aat   2343
Cys Met Ser Trp Asp Ile Arg Pro Tyr Gly Tyr Glu Ser Glu Asn Asn
        695                 700                 705 ttg gat gaa aaa gtg ctt gaa gcc ctc aga cca cac tcc aac ctg aaa   2391
Leu Asp Glu Lys Val Leu Glu Ala Leu Arg Pro His Ser Asn Leu Lys
710                 715                 720
```

-continued

```
tca cta aag ctc att ggc ttc aga ggt ttt cat ttt cca aat tgg atg      2439
Ser Leu Lys Leu Ile Gly Phe Arg Gly Phe His Phe Pro Asn Trp Met
725             730                 735                 740 aac gct tcg gtt ttg aaa aat gtc gtc tct att gaa att gaa tgt gaa      2487
Asn Ala Ser Val Leu Lys Asn Val Val Ser Ile Glu Ile Glu Cys Glu
        745                 750                 755 aac tgc tgg cgt tta cca cca ttt gga gag ctg cct tgt cta gaa agt      2535
Asn Cys Trp Arg Leu Pro Pro Phe Gly Glu Leu Pro Cys Leu Glu Ser
    760                 765                 770 cta aag tta tac aac gga tct gcg gag gtg gag tat att gaa gag gat      2583
Leu Lys Leu Tyr Asn Gly Ser Ala Glu Val Glu Tyr Ile Glu Glu Asp
775                 780                 785 gat ggt cat tcc aca tta aag ttc cca tac ttg aaa cga ctt gct att      2631
Asp Gly His Ser Thr Leu Lys Phe Pro Tyr Leu Lys Arg Leu Ala Ile
790                 795                 800 gaa aga ttt cca aat ctg aaa gga ctg ctg aga agt gaa gga gaa gag      2679
Glu Arg Phe Pro Asn Leu Lys Gly Leu Leu Arg Ser Glu Gly Glu Glu
805             810                  815                 820 aaa ttc tcc atg ctt gaa gaa atg gaa att tgg cat tgc cct atg ttt      2727
Lys Phe Ser Met Leu Glu Glu Met Glu Ile Trp His Cys Pro Met Phe
            825                 830                  835 gtt ttt cca gca ttc tct tct gtc acg aaa ttg gat gtc tgg ggg gaa      2775
Val Phe Pro Ala Phe Ser Ser Val Thr Lys Leu Asp Val Trp Gly Glu
        840                 845                 850 ata gat gca gca agt ctt agc tcc ata tct aag ctt acc act ctt acg      2823
Ile Asp Ala Ala Ser Leu Ser Ser Ile Ser Lys Leu Thr Thr Leu Thr
    855                 860                 865 tct ctc tct att gat cat aac ttt gaa gca aca act ctc cca gaa gag      2871
Ser Leu Ser Ile Asp His Asn Phe Glu Ala Thr Thr Leu Pro Glu Glu
870                 875                 880 atg ttc aaa cgc ctt gta aat ctt gag tcc ttg agc att ata tac ttc      2919
Met Phe Lys Arg Leu Val Asn Leu Glu Ser Leu Ser Ile Ile Tyr Phe
885                 890                 895                 900 aaa aaa ctc aga gag ttg cca agc agc ctg gct agc ctc aat gct ttg      2967
Lys Lys Leu Arg Glu Leu Pro Ser Ser Leu Ala Ser Leu Asn Ala Leu
            905                 910                 915 aag tgt cta aaa att cat tat tgt tac gca cta gag agt ctc ccc gaa      3015
Lys Cys Leu Lys Ile His Tyr Cys Tyr Ala Leu Glu Ser Leu Pro Glu
        920                 925                 930 caa ggg atg gaa ggg tta act tca ctc acc gac tta tat gtt caa aac      3063
Gln Gly Met Glu Gly Leu Thr Ser Leu Thr Asp Leu Tyr Val Gln Asn
    935                 940                 945 tgt gag atg cta aaa tgt tta cct gag gga ttg cag cac cta aga gcc      3111
Cys Glu Met Leu Lys Cys Leu Pro Glu Gly Leu Gln His Leu Arg Ala
950                 955                 960 ctc act agt tta caa att tat ggc tgt cca gca ttg aaa aag cgg tgt      3159
Leu Thr Ser Leu Gln Ile Tyr Gly Cys Pro Ala Leu Lys Lys Arg Cys
965                 970                 975                 980 gcg aag ggg ata gga gag gac tgg cac aaa att gct cac att cct aat      3207
Ala Lys Gly Ile Gly Glu Asp Trp His Lys Ile Ala His Ile Pro Asn
            985                 990                 995 gta gat att tgt tag                                                   3222
Val Asp Ile Cys
        1000
```

<210> SEQ ID NO 8
<211> LENGTH: 1000
<212> TYPE: PRT
<213> ORGANISM: Solanum Bulbocastanum

<400> SEQUENCE: 8

```
Met Ala Glu Ala Phe Leu Gln Val Leu Leu Gly Asn Ile Thr Ser Phe
1               5                   10                  15

Ile Gln Gly Glu Leu Val Leu Leu Phe Gly Phe Glu Asn Asp Phe Arg
            20                  25                  30

Lys Leu Ser Ser Thr Phe Ser Thr Ile Gln Leu Val Leu Glu Asp Ala
            35                  40                  45

Ser Glu Lys Gln Leu Lys Asp Lys Ala Ile Glu Asn Trp Leu Gln Lys
    50                  55                  60

Leu Asn Phe Ala Ala Tyr Glu Val Asp Asp Ile Leu Asp Glu Cys Lys
65                  70                  75                  80

Asn Glu Ala Ala Arg Phe Asn Gln Ser Leu Leu Gly Tyr Ile His Pro
                85                  90                  95

Lys Ile Ile Ile Phe Arg Tyr Lys Leu Gly Lys Arg Met Lys Arg Met
            100                 105                 110

Met Glu Lys Leu Asp Ala Ile Ala Asp Glu Arg Arg Lys Phe His Leu
            115                 120                 125

Arg Ala Lys Ile Val Glu Lys Gln Ala Ser Lys Arg Glu Thr Gly Ala
130                 135                 140

His Leu Lys Leu Cys Leu Ala Lys Tyr Leu Leu Ile Ala Thr Gly Phe
145                 150                 155                 160

Val Leu Ala Glu Pro Lys Val Tyr Gly Arg Asp Lys Glu Lys Asp Glu
                165                 170                 175

Met Val Lys Ile Leu Ile Asn Ser Val Ser Asn Ala Gln Glu Leu Leu
            180                 185                 190

Val Leu Pro Ile Leu Gly Met Gly Gly Leu Gly Lys Thr Thr Leu Ala
            195                 200                 205

Gln Met Ile Phe Asn Asp Gln Ser Val Thr Ala His Phe Asn Leu Lys
210                 215                 220

Ile Trp Val Cys Val Ser Asp Asp Phe Asp Glu Lys Arg Leu Ile Lys
225                 230                 235                 240

Ala Ile Val Glu Ser Ile Glu Arg Arg Pro Leu Gly Asp Ile Asp Leu
                245                 250                 255

Ala Pro Leu Gln Lys Lys Leu Gln Glu Leu Leu Asn Gly Lys Arg Tyr
            260                 265                 270

Phe Leu Val Leu Asp Asp Val Trp Asn Glu Asp Gln Glu Lys Trp Ala
            275                 280                 285

Lys Ile Lys Ala Val Leu Lys Val Gly Ala Gln Gly Ser Ser Ile Leu
290                 295                 300

Ala Thr Thr Arg Leu Glu Arg Val Gly Ser Ile Met Gly Thr Trp Gln
305                 310                 315                 320

Pro Tyr Gln Leu Ser Ile Leu Ser Pro Glu Tyr Cys Trp Leu Leu Phe
                325                 330                 335

Lys Gln Arg Ala Phe Gly His Gln Thr Glu Thr Asn Pro Ala Leu Val
            340                 345                 350

Gly Ile Gly Lys Glu Ile Val Lys Lys Cys Gly Gly Val Pro Leu Ala
            355                 360                 365

Ala Lys Thr Leu Gly Gly Leu Leu Arg Phe Lys Arg Glu Glu Ser Glu
370                 375                 380

Trp Glu His Val Lys Asp Ser Glu Ile Trp Asn Leu Pro Gln Asp Glu
385                 390                 395                 400

Asn Ser Val Leu Pro Ser Leu Arg Leu Ser Tyr His His Leu Pro Leu
                405                 410                 415
```

```
Asn Leu Arg Gln Cys Phe Ala Tyr Cys Ala Val Phe Pro Lys Asp Thr
            420                 425                 430
Lys Ile Glu Lys Glu Tyr Leu Ile Thr Leu Trp Met Ala His Gly Phe
        435                 440                 445
Leu Leu Ser Lys Glu Asn Ser Glu Leu Glu Asp Val Gly Asn Glu Val
    450                 455                 460
Trp Lys Glu Leu Tyr Leu Arg Ser Phe Gln Glu Val Glu Tyr
465                 470                 475                 480
Lys Phe Gly Asn Thr Tyr Phe Lys Met His Asp Leu Ile His Asp Leu
                485                 490                 495
Ala Thr Ser Leu Phe Ser Thr Asn Thr Arg Ser Ser Lys Ile Arg Gln
            500                 505                 510
Ile Arg Val Ala Gln Lys Asn Thr Ile Pro Ile Gly Phe Ala Glu Val
        515                 520                 525
Val Pro Ser Tyr Ser Pro Leu Ile Phe Lys Arg Phe Val Ser Leu Arg
    530                 535                 540
Val Leu Asp Met Lys Phe Ser Lys Phe Asp Gln Leu Ser Ser Ser Ile
545                 550                 555                 560
Gly Asp Leu Ile His Leu Arg Leu Leu Asn Leu Arg Gly Ser Ser Ile
                565                 570                 575
Arg Ser Leu Pro Lys Arg Leu Cys Lys Leu Gln Asn Leu Gln Thr Leu
            580                 585                 590
Asp Ile Ser Cys Cys Phe Ser Leu Ser Tyr Ile Pro Lys Gln Ile Ser
        595                 600                 605
Lys Leu Ser Ser Leu Arg Asn Leu Val Phe Ser Gly Cys Gln Ile Thr
    610                 615                 620
Ser Met Pro Pro Arg Ile Gly Ser Leu Thr Cys Leu Lys Thr Leu Asp
625                 630                 635                 640
Tyr Phe Ile Val Gly Glu Arg Lys Gly Tyr Gln Leu Gly Glu Leu Arg
                645                 650                 655
Asn Leu Ser Leu His Gly Ser Leu Ser Ile Ser His Leu Glu Arg Val
            660                 665                 670
Lys Ser Glu Thr Asp Ala Lys Glu Ala Asn Leu Ser Thr Lys Gln Lys
        675                 680                 685
Leu Tyr Asn Leu Cys Met Ser Trp Asp Ile Arg Pro Tyr Gly Tyr Glu
    690                 695                 700
Ser Glu Asn Asn Leu Asp Glu Lys Val Leu Glu Ala Leu Arg Pro His
705                 710                 715                 720
Ser Asn Leu Lys Ser Leu Lys Leu Ile Gly Phe Arg Gly Phe His Phe
                725                 730                 735
Pro Asn Trp Met Asn Ala Ser Val Leu Lys Asn Val Val Ser Ile Glu
            740                 745                 750
Ile Glu Cys Glu Asn Cys Trp Arg Leu Pro Pro Phe Gly Glu Leu Pro
        755                 760                 765
Cys Leu Glu Ser Leu Lys Leu Tyr Asn Gly Ser Ala Glu Val Glu Tyr
    770                 775                 780
Ile Glu Glu Asp Asp Gly His Ser Thr Leu Lys Phe Pro Tyr Leu Lys
785                 790                 795                 800
Arg Leu Ala Ile Glu Arg Phe Pro Asn Leu Lys Gly Leu Leu Arg Ser
                805                 810                 815
Glu Gly Glu Glu Lys Phe Ser Met Leu Glu Glu Met Glu Ile Trp His
            820                 825                 830
```

```
Cys Pro Met Phe Val Phe Pro Ala Phe Ser Ser Val Thr Lys Leu Asp
        835                 840                 845

Val Trp Gly Glu Ile Asp Ala Ala Ser Leu Ser Ser Ile Ser Lys Leu
850                 855                 860

Thr Thr Leu Thr Ser Leu Ser Ile Asp His Asn Phe Glu Ala Thr Thr
865                 870                 875                 880

Leu Pro Glu Glu Met Phe Lys Arg Leu Val Asn Leu Glu Ser Leu Ser
                885                 890                 895

Ile Ile Tyr Phe Lys Lys Leu Arg Glu Leu Pro Ser Ser Leu Ala Ser
            900                 905                 910

Leu Asn Ala Leu Lys Cys Leu Lys Ile His Tyr Cys Tyr Ala Leu Glu
            915                 920                 925

Ser Leu Pro Glu Gln Gly Met Glu Gly Leu Thr Ser Leu Thr Asp Leu
        930                 935                 940

Tyr Val Gln Asn Cys Glu Met Leu Lys Cys Leu Pro Glu Gly Leu Gln
945                 950                 955                 960

His Leu Arg Ala Leu Thr Ser Leu Gln Ile Tyr Gly Cys Pro Ala Leu
                965                 970                 975

Lys Lys Arg Cys Ala Lys Gly Ile Gly Glu Asp Trp His Lys Ile Ala
            980                 985                 990

His Ile Pro Asn Val Asp Ile Cys
            995                 1000
```

<210> SEQ ID NO 9
<211> LENGTH: 5028
<212> TYPE: DNA
<213> ORGANISM: Solanum bulbocastanum
<220> FEATURE:
<221> NAME/KEY: promoter
<222> LOCATION: (1)..(953)
<223> OTHER INFORMATION: Potato Ubi3 promoter
<220> FEATURE:
<221> NAME/KEY: gene
<222> LOCATION: (973)..(4566)
<223> OTHER INFORMATION: Solanum bulbocastanum genomic Sbu11
<220> FEATURE:
<221> NAME/KEY: CDS
<222> LOCATION: (1029)..(1459)
<220> FEATURE:
<221> NAME/KEY: Intron
<222> LOCATION: (1460)..(1871)
<220> FEATURE:
<221> NAME/KEY: CDS
<222> LOCATION: (1872)..(4404)

<400> SEQUENCE: 9

```
aagcttgcat gcctgcaggt cgactctaga ggatccaaag cacatagtta tcgatttaaa    60
tttcatcgaa gagattaata tcgaataatc atatacatac tttaaataca taacaaattt   120
taaatacata tatctggtat ataattaatt ttttaaagtc atgaagtatg tatcaaatac   180
acatatggaa aaaattaact attcataatt taaaaaatag aaaagataca tctagtgaaa   240
ttaggtgcat gtatcaaata cattaggaaa agggcatata tcttgatcta gataattaac   300
gattttgatt tatgtataat ttccaaatga aggtttatat ctacttcaga aataacaata   360
tacttttatc agaacattca acaaagcaac aaccaactag agtgaaaaat acacattgtt   420
ctctagacat acaaaattga gaaagaatc tcaaaattta gagaaacaaa tctgaatttc    480
tagaagaaaa aaataattat gcactttgct attgctcgaa aaataaatga aagaaattag   540
acttttttaa aagatgttag actagatata ctcaaaagct attaaggag taatattctt     600
cttacattaa gtatttagt tacagtcctg taattaaaga cacattttag attgtatcta    660
```

```
                                                -continued aacttaaatg tatctagaat acatatattt gaatgcatca tatacatgta tccgacacac        720
caattctcat aaaaaacgta atatcctaaa ctaatttatc cttcaagtca acttaagccc        780
aatatacatt ttcatctcta aaggcccaag tggcacaaaa tgtcaggccc aattacgaag        840
aaaagggctt gtaaaaccct aataaagtgg cactggcaga gcttacactc tcattccatc        900
aacaaagaaa ccctaaaagc cgcagcgcca ctgatttctc tcctccaggc gaaggatccc        960
cgggggatcc ccccaacatc ttacttcatt tcaaaaaata tagattcatt gcgtactcac      1020 aatactct atg gct gaa gct ttc ctt caa gtt ctg tta gac aat ctg act        1070
         Met Ala Glu Ala Phe Leu Gln Val Leu Leu Asp Asn Leu Thr
         1               5                   10 tgt ttc atc caa ggg gaa ctt gga ttg att ctt ggt ttt aag gat gag         1118
Cys Phe Ile Gln Gly Glu Leu Gly Leu Ile Leu Gly Phe Lys Asp Glu
15                  20                  25                  30 ttc gaa aag ctt caa agc acg ttt act aca atc caa gct gtg cta gaa         1166
Phe Glu Lys Leu Gln Ser Thr Phe Thr Thr Ile Gln Ala Val Leu Glu
                35                  40                  45 gat gct cag aag aag caa ttg aag gac aag gca ata gaa aat tgg ttg         1214
Asp Ala Gln Lys Lys Gln Leu Lys Asp Lys Ala Ile Glu Asn Trp Leu
        50                  55                  60 cag aaa ctc aat gct gct gca tat gag gct gat gac atc ttg gac gaa         1262
Gln Lys Leu Asn Ala Ala Ala Tyr Glu Ala Asp Asp Ile Leu Asp Glu
65                  70                  75 tgt aaa act gag gca cca att aga cag aag aag aac aaa tat ggg tgt         1310
Cys Lys Thr Glu Ala Pro Ile Arg Gln Lys Lys Asn Lys Tyr Gly Cys
        80                  85                  90 tat cat cca aac gtt atc act ttt cgt cac aag att ggg aaa agg atg         1358
Tyr His Pro Asn Val Ile Thr Phe Arg His Lys Ile Gly Lys Arg Met
95                  100                 105                 110 aaa aag att atg gag aaa cta gat gta att gca gcg gaa cga att aag         1406
Lys Lys Ile Met Glu Lys Leu Asp Val Ile Ala Ala Glu Arg Ile Lys
                115                 120                 125 ttt cat ttg gat gaa agg act ata gag aga caa gtt gct aca cgc caa         1454
Phe His Leu Asp Glu Arg Thr Ile Glu Arg Gln Val Ala Thr Arg Gln
        130                 135                 140 aca gg  tgctcatctt agatattttt ctgaaaaaac agctttatat catcaaattc          1509
Thr Gly
atgtgtgttt tgggaattcg tctaatctaa atgttcgtct caagtctaag tagataagtg      1569
gatccagctt tggatttatt aatctattag ctaaatctgt ttagtgaagt ttttaacata      1629
tataacctca gataaatcca tagcttactc ataggattag gataggcccc caagtctaaa      1689
tgacaggata aagccagagt tgttttagct cttataaatt aacaatgata ataatgtgaa      1749
ttcaaaaaag tgcattttt taatttgaaa tatttctgct gcttctcaag cttatcattg       1809 tcttttact gtgcaaaatt ctactttgta tttttgctga ctcctaccga gcttgggcca       1869 gg t ttt gtt ttg aat gaa cca caa gtt tat gga aga gac aaa gaa aag       1917
    Phe Val Leu Asn Glu Pro Gln Val Tyr Gly Arg Asp Lys Glu Lys
    145                 150                 155 gac gag ata gtg aaa atc ctg ata aac aat gtt agc aat gcc caa aca        1965
Asp Glu Ile Val Lys Ile Leu Ile Asn Asn Val Ser Asn Ala Gln Thr
160                 165                 170                 175 ctt cca gtc ctc cca ata ctt ggt atg ggg gga cta gga aag acg act        2013
Leu Pro Val Leu Pro Ile Leu Gly Met Gly Gly Leu Gly Lys Thr Thr
                180                 185                 190 ctt gcc caa atg gtc ttc aat gat cag aga gta att gag cat ttc cat        2061
Leu Ala Gln Met Val Phe Asn Asp Gln Arg Val Ile Glu His Phe His
        195                 200                 205
```

```
ccc aaa ata tgg att tgt gtc tcg gaa gat ttt aat gag aag agg ttg    2109
Pro Lys Ile Trp Ile Cys Val Ser Glu Asp Phe Asn Glu Lys Arg Leu
        210                 215                 220 ata aag gaa att gta gaa tct att gaa gaa aag tca ctt ggt ggc atg    2157
Ile Lys Glu Ile Val Glu Ser Ile Glu Glu Lys Ser Leu Gly Gly Met
225                 230                 235 gac ttg gct cca ctt caa aag aag ctt cgg gac ttg ctg aat gga aaa    2205
Asp Leu Ala Pro Leu Gln Lys Lys Leu Arg Asp Leu Leu Asn Gly Lys
240                 245                 250                 255 aaa tat ttg ctc gtc tta gat gat gtt tgg aat gaa gat caa gat aag    2253
Lys Tyr Leu Leu Val Leu Asp Asp Val Trp Asn Glu Asp Gln Asp Lys
                260                 265                 270 tgg gct aag tta aga caa gtc ttg aag gtt gga gca agt ggc gct tct    2301
Trp Ala Lys Leu Arg Gln Val Leu Lys Val Gly Ala Ser Gly Ala Ser
            275                 280                 285 gtt cta acc act act cgt ctt gaa aag gtt gga tca att atg gga aca    2349
Val Leu Thr Thr Thr Arg Leu Glu Lys Val Gly Ser Ile Met Gly Thr
        290                 295                 300 ttg caa cca tat gaa ttg tca aat ttg tct caa gaa gat tgt tgg ttg    2397
Leu Gln Pro Tyr Glu Leu Ser Asn Leu Ser Gln Glu Asp Cys Trp Leu
305                 310                 315 ttg ttc atg caa cgt gca ttt ggg cac caa gaa gaa ata aat ctt aat    2445
Leu Phe Met Gln Arg Ala Phe Gly His Gln Glu Glu Ile Asn Leu Asn
320                 325                 330                 335 ctt gtg gct atc gga aag gag att gtg aaa aaa tgt ggt ggt gtg cct    2493
Leu Val Ala Ile Gly Lys Glu Ile Val Lys Lys Cys Gly Gly Val Pro
                340                 345                 350 cta gca gct aaa act ctt gga ggt att ttg cgc ttt aag aga gaa gaa    2541
Leu Ala Ala Lys Thr Leu Gly Gly Ile Leu Arg Phe Lys Arg Glu Glu
            355                 360                 365 aga cag tgg gaa cat gtg aga gat agt gag att tgg aaa ttg cct caa    2589
Arg Gln Trp Glu His Val Arg Asp Ser Glu Ile Trp Lys Leu Pro Gln
        370                 375                 380 gaa gaa agt tct att ctg cct gcc ctg aga ctt agt tac cat cac ctt    2637
Glu Glu Ser Ser Ile Leu Pro Ala Leu Arg Leu Ser Tyr His His Leu
385                 390                 395 cca ctt gat ttg aga caa tgc ttt aca tat tgt gca gta ttc cca aag    2685
Pro Leu Asp Leu Arg Gln Cys Phe Thr Tyr Cys Ala Val Phe Pro Lys
400                 405                 410                 415 gat acc gaa atg gaa aag gga aat cta atc tct ctc tgg atg gca cat    2733
Asp Thr Glu Met Glu Lys Gly Asn Leu Ile Ser Leu Trp Met Ala His
                420                 425                 430 ggt ttt att tta tcg aaa gga aac ttg gag cta gag aat gta ggt aat    2781
Gly Phe Ile Leu Ser Lys Gly Asn Leu Glu Leu Glu Asn Val Gly Asn
            435                 440                 445 gaa gta tgg aat gaa tta tac ttg agg tct ttc ttc caa gag att gaa    2829
Glu Val Trp Asn Glu Leu Tyr Leu Arg Ser Phe Phe Gln Glu Ile Glu
        450                 455                 460 gtt aaa tct ggt caa act tat ttc aag atg cat gat ctc att cat gat    2877
Val Lys Ser Gly Gln Thr Tyr Phe Lys Met His Asp Leu Ile His Asp
465                 470                 475 ctg gca aca tct cta ttt tcg gca agc aca tca agc agc aat atc cga    2925
Leu Ala Thr Ser Leu Phe Ser Ala Ser Thr Ser Ser Ser Asn Ile Arg
480                 485                 490                 495 gaa ata att gta gaa aat tac ata cat atg atg tcc att ggt ttc act    2973
Glu Ile Ile Val Glu Asn Tyr Ile His Met Met Ser Ile Gly Phe Thr
                500                 505                 510 aaa gtg gta tct tct tac tct ctt tcc cac ttg cag aag ttt gtc tcg    3021
Lys Val Val Ser Ser Tyr Ser Leu Ser His Leu Gln Lys Phe Val Ser
            515                 520                 525
```

-continued

| | | |
|---|---|---|
| ttg agg gtg ctt aat cta agt gac ata aaa ctt aag cag tta ccg tct<br>Leu Arg Val Leu Asn Leu Ser Asp Ile Lys Leu Lys Gln Leu Pro Ser<br>530 535 540 | | 3069 |
| tcc att gga gat cta gta cat tta aga tac cta aac ttg tct ggc aat<br>Ser Ile Gly Asp Leu Val His Leu Arg Tyr Leu Asn Leu Ser Gly Asn<br>545 550 555 | | 3117 |
| act agt att cgt agt ctt cca aac cag tta tgc aag ctt caa aat ctg<br>Thr Ser Ile Arg Ser Leu Pro Asn Gln Leu Cys Lys Leu Gln Asn Leu<br>560 565 570 575 | | 3165 |
| cag act ctt gat cta cat ggc tgt cat tca ctt tgt tgt ttg cca aaa<br>Gln Thr Leu Asp Leu His Gly Cys His Ser Leu Cys Cys Leu Pro Lys<br>580 585 590 | | 3213 |
| gaa aca agc aaa ctt ggt agt ctt cga aat ctt tta ctt gat ggt tgc<br>Glu Thr Ser Lys Leu Gly Ser Leu Arg Asn Leu Leu Leu Asp Gly Cys<br>595 600 605 | | 3261 |
| tat gga ttg act tgt atg cca cca agg ata gga tct ttg aca tgc ctt<br>Tyr Gly Leu Thr Cys Met Pro Pro Arg Ile Gly Ser Leu Thr Cys Leu<br>610 615 620 | | 3309 |
| aag act cta agt aga ttt gtg gtg gga att cag aag aaa agt tgt caa<br>Lys Thr Leu Ser Arg Phe Val Val Gly Ile Gln Lys Lys Ser Cys Gln<br>625 630 635 | | 3357 |
| ctt ggt gaa tta cga aac ctg aat ctc tat ggc tca att gaa atc acg<br>Leu Gly Glu Leu Arg Asn Leu Asn Leu Tyr Gly Ser Ile Glu Ile Thr<br>640 645 650 655 | | 3405 |
| cat ctt gag aga gtg aag aat gat atg gat gca aaa gaa gcc aat tta<br>His Leu Glu Arg Val Lys Asn Asp Met Asp Ala Lys Glu Ala Asn Leu<br>660 665 670 | | 3453 |
| tct gca aaa gaa aat ctg cat tct tta agc atg aaa tgg gat gac gat<br>Ser Ala Lys Glu Asn Leu His Ser Leu Ser Met Lys Trp Asp Asp Asp<br>675 680 685 | | 3501 |
| gaa cgt cca cgt ata tat gaa tca gaa aaa gtt gaa gtg ctt gaa gct<br>Glu Arg Pro Arg Ile Tyr Glu Ser Glu Lys Val Glu Val Leu Glu Ala<br>690 695 700 | | 3549 |
| ctc aaa cca cac tcc aat ctg act tgt tta aca atc agg ggc ttc aga<br>Leu Lys Pro His Ser Asn Leu Thr Cys Leu Thr Ile Arg Gly Phe Arg<br>705 710 715 | | 3597 |
| gga atc cgt ctc cca gac tgg atg aat cac tca gtt tgt aaa aat gtt<br>Gly Ile Arg Leu Pro Asp Trp Met Asn His Ser Val Leu Lys Asn Val<br>720 725 730 735 | | 3645 |
| gtc tct att gaa atc atc agt tgc aaa aac tgc tca tgc tta cca ccc<br>Val Ser Ile Glu Ile Ile Ser Cys Lys Asn Cys Ser Cys Leu Pro Pro<br>740 745 750 | | 3693 |
| ttt ggt gag ctg cct tgt cta aaa agt cta gag tta tgg agg ggg tct<br>Phe Gly Glu Leu Pro Cys Leu Lys Ser Leu Glu Leu Trp Arg Gly Ser<br>755 760 765 | | 3741 |
| gcg gaa gtg gag tat gtt gat tct gga ttc cct aca aga aga agg ttt<br>Ala Glu Val Glu Tyr Val Asp Ser Gly Phe Pro Thr Arg Arg Arg Phe<br>770 775 780 | | 3789 |
| cca tct ctg aga aaa ctt aat ata cgc gaa ttt gat aat ctg aaa gga<br>Pro Ser Leu Arg Lys Leu Asn Ile Arg Glu Phe Asp Asn Leu Lys Gly<br>785 790 795 | | 3837 |
| ttg ctg aaa aag gaa gga gaa gag caa tgc cct gtg ctt gaa gag ata<br>Leu Leu Lys Lys Glu Gly Glu Glu Gln Cys Pro Val Leu Glu Glu Ile<br>800 805 810 815 | | 3885 |
| gag att aaa tgt tgc cct atg ttt gtt att cca acc ctt tct tct gtc<br>Glu Ile Lys Cys Cys Pro Met Phe Val Ile Pro Thr Leu Ser Ser Val<br>820 825 830 | | 3933 |
| aag aaa ttg gta gtt agt ggg gac aag tca gat gca ata ggt ttc agt<br>Lys Lys Leu Val Val Ser Gly Asp Lys Ser Asp Ala Ile Gly Phe Ser | | 3981 |

```
                835                 840                 845
tcc ata tct aat ctc atg gct ctt act tcc ctc caa att cgc tat aac    4029
Ser Ile Ser Asn Leu Met Ala Leu Thr Ser Leu Gln Ile Arg Tyr Asn
        850                 855                 860 aaa gaa gat gct tca ctc cca gaa gag atg ttc aaa agc ctt gca aat    4077
Lys Glu Asp Ala Ser Leu Pro Glu Glu Met Phe Lys Ser Leu Ala Asn
865                 870                 875 ctc aaa tac ttg aat atc tct ttt tac ttc aat ctt aaa gag ctg cct    4125
Leu Lys Tyr Leu Asn Ile Ser Phe Tyr Phe Asn Leu Lys Glu Leu Pro
880                 885                 890                 895 acc agc ctg gct agt ctc aat gct ttg aag cat ctg gaa att cat agt    4173
Thr Ser Leu Ala Ser Leu Asn Ala Leu Lys His Leu Glu Ile His Ser
            900                 905                 910 tgt tat gca cta gag agt ctc ccc gag gaa ggt gtg aaa ggt tta att    4221
Cys Tyr Ala Leu Glu Ser Leu Pro Glu Glu Gly Val Lys Gly Leu Ile
        915                 920                 925 tca ctc aca cag tta tcc ata aca tac tgt gaa atg cta caa tgt tta    4269
Ser Leu Thr Gln Leu Ser Ile Thr Tyr Cys Glu Met Leu Gln Cys Leu
    930                 935                 940 ccg gag gga ttg cag cac cta aca gcc ctc aca aat tta tca gtt gag    4317
Pro Glu Gly Leu Gln His Leu Thr Ala Leu Thr Asn Leu Ser Val Glu
945                 950                 955 ttt tgt cca aca ctg gcc aag cgg tgt gag aag gga ata gga gaa gac    4365
Phe Cys Pro Thr Leu Ala Lys Arg Cys Glu Lys Gly Ile Gly Glu Asp
960                 965                 970                 975 tgg tac aaa att gct cac att cct cgt gtg ttt att tat tagtattccc    4414
Trp Tyr Lys Ile Ala His Ile Pro Arg Val Phe Ile Tyr
            980                 985 aattagatgt aatttctga ttttctttg gaaacaaatc aactatttgt aagatctatt    4474
tgtattatac ttgattttc ttgggtctgt aacaataaat atttgaaatt tttcatatta    4534
agattcagaa ttagtcttat agctaacggt atcgggtacc gagctcgaat tcggcttgat    4594
ccaaattttg attttaatgt ttagcaaatg tcctatcagt tttctctttt tgtcgaacgg    4654
taatttagag ttttttttgc tatatggatt ttcgttttg atgtatgtga caaccctcgg    4714
gattgttgat ttatttcaaa actaagagtt tttgcttatt gttctcgtct attttggata    4774
tcaatcttag ttttatatct tttctagttc tctacgtgtt aaatgttcaa cacactagca    4834
atttggctgc agcgtatgga ttatggaact atcaagtctg tgggatcgat aaatatgctt    4894
ctcaggaatt tgagatttta cagtcttat gctcattggg ttgagtataa atagtaaaa    4954
aaatagtaaa tttaagcaat aatgttaggt gctatgtgtc tgtcgagact attggccggc    5014
ctcaagccga attc                                                    5028
```

<210> SEQ ID NO 10
<211> LENGTH: 988
<212> TYPE: PRT
<213> ORGANISM: Solanum bulbocastanum

<400> SEQUENCE: 10

```
Met Ala Glu Ala Phe Leu Gln Val Leu Leu Asp Asn Leu Thr Cys Phe
1               5                   10                  15

Ile Gln Gly Glu Leu Gly Leu Ile Leu Gly Phe Lys Asp Glu Phe Glu
            20                  25                  30

Lys Leu Gln Ser Thr Phe Thr Thr Ile Gln Ala Val Leu Glu Asp Ala
        35                  40                  45

Gln Lys Lys Gln Leu Lys Asp Lys Ala Ile Glu Asn Trp Leu Gln Lys
    50                  55                  60
```

-continued

```
Leu Asn Ala Ala Ala Tyr Glu Ala Asp Asp Ile Leu Asp Glu Cys Lys
 65                  70                  75                  80

Thr Glu Ala Pro Ile Arg Gln Lys Lys Asn Lys Tyr Gly Cys Tyr His
                 85                  90                  95

Pro Asn Val Ile Thr Phe Arg His Lys Ile Gly Lys Arg Met Lys Lys
            100                 105                 110

Ile Met Glu Lys Leu Asp Val Ile Ala Ala Glu Arg Ile Lys Phe His
        115                 120                 125

Leu Asp Glu Arg Thr Ile Glu Arg Gln Val Ala Thr Arg Gln Thr Gly
130                 135                 140

Phe Val Leu Asn Glu Pro Gln Val Tyr Gly Arg Asp Lys Glu Lys Asp
145                 150                 155                 160

Glu Ile Val Lys Ile Leu Ile Asn Asn Val Ser Asn Ala Gln Thr Leu
                165                 170                 175

Pro Val Leu Pro Ile Leu Gly Met Gly Gly Leu Gly Lys Thr Thr Leu
            180                 185                 190

Ala Gln Met Val Phe Asn Asp Gln Arg Val Ile Glu His Phe His Pro
        195                 200                 205

Lys Ile Trp Ile Cys Val Ser Glu Asp Phe Asn Glu Lys Arg Leu Ile
    210                 215                 220

Lys Glu Ile Val Glu Ser Ile Glu Glu Lys Ser Leu Gly Gly Met Asp
225                 230                 235                 240

Leu Ala Pro Leu Gln Lys Lys Leu Arg Asp Leu Leu Asn Gly Lys Lys
                245                 250                 255

Tyr Leu Val Leu Asp Asp Val Trp Asn Glu Asp Gln Asp Lys Trp
            260                 265                 270

Ala Lys Leu Arg Gln Val Leu Lys Val Gly Ala Ser Gly Ala Ser Val
        275                 280                 285

Leu Thr Thr Thr Arg Leu Glu Lys Val Gly Ser Ile Met Gly Thr Leu
    290                 295                 300

Gln Pro Tyr Glu Leu Ser Asn Leu Ser Gln Glu Asp Cys Trp Leu Leu
305                 310                 315                 320

Phe Met Gln Arg Ala Phe Gly His Gln Glu Ile Asn Leu Asn Leu
                325                 330                 335

Val Ala Ile Gly Lys Glu Ile Val Lys Lys Cys Gly Gly Val Pro Leu
            340                 345                 350

Ala Ala Lys Thr Leu Gly Gly Ile Leu Arg Phe Lys Arg Glu Glu Arg
        355                 360                 365

Gln Trp Glu His Val Arg Asp Ser Glu Ile Trp Lys Leu Pro Gln Glu
    370                 375                 380

Glu Ser Ser Ile Leu Pro Ala Leu Arg Leu Ser Tyr His His Leu Pro
385                 390                 395                 400

Leu Asp Leu Arg Gln Cys Phe Thr Tyr Cys Ala Val Phe Pro Lys Asp
                405                 410                 415

Thr Glu Met Glu Lys Gly Asn Leu Ile Ser Leu Trp Met Ala His Gly
            420                 425                 430

Phe Ile Leu Ser Lys Gly Asn Leu Glu Leu Glu Asn Val Gly Asn Glu
        435                 440                 445

Val Trp Asn Glu Leu Tyr Leu Arg Ser Phe Phe Gln Glu Ile Glu Val
    450                 455                 460

Lys Ser Gly Gln Thr Tyr Phe Lys Met His Asp Leu Ile His Asp Leu
465                 470                 475                 480
```

```
Ala Thr Ser Leu Phe Ser Ala Ser Thr Ser Ser Ser Asn Ile Arg Glu
            485                 490                 495
Ile Ile Val Glu Asn Tyr Ile His Met Met Ser Ile Gly Phe Thr Lys
        500                 505                 510
Val Val Ser Ser Tyr Ser Leu Ser His Leu Gln Lys Phe Val Ser Leu
            515                 520                 525
Arg Val Leu Asn Leu Ser Asp Ile Lys Leu Lys Gln Leu Pro Ser Ser
    530                 535                 540
Ile Gly Asp Leu Val His Leu Arg Tyr Leu Asn Leu Ser Gly Asn Thr
545                 550                 555                 560
Ser Ile Arg Ser Leu Pro Asn Gln Leu Cys Lys Leu Gln Asn Leu Gln
            565                 570                 575
Thr Leu Asp Leu His Gly Cys His Ser Leu Cys Cys Leu Pro Lys Glu
            580                 585                 590
Thr Ser Lys Leu Gly Ser Leu Arg Asn Leu Leu Asp Gly Cys Tyr
            595                 600                 605
Gly Leu Thr Cys Met Pro Pro Arg Ile Gly Ser Leu Thr Cys Leu Lys
    610                 615                 620
Thr Leu Ser Arg Phe Val Val Gly Ile Gln Lys Lys Ser Cys Gln Leu
625                 630                 635                 640
Gly Glu Leu Arg Asn Leu Asn Leu Tyr Gly Ser Ile Glu Ile Thr His
            645                 650                 655
Leu Glu Arg Val Lys Asn Asp Met Asp Ala Lys Glu Ala Asn Leu Ser
            660                 665                 670
Ala Lys Glu Asn Leu His Ser Leu Ser Met Lys Trp Asp Asp Glu
    675                 680                 685
Arg Pro Arg Ile Tyr Glu Ser Glu Lys Val Glu Val Leu Glu Ala Leu
    690                 695                 700
Lys Pro His Ser Asn Leu Thr Cys Leu Thr Ile Arg Gly Phe Arg Gly
705                 710                 715                 720
Ile Arg Leu Pro Asp Trp Met Asn His Ser Val Leu Lys Asn Val Val
            725                 730                 735
Ser Ile Glu Ile Ile Ser Cys Lys Asn Cys Ser Cys Leu Pro Pro Phe
            740                 745                 750
Gly Glu Leu Pro Cys Leu Lys Ser Leu Glu Leu Trp Arg Gly Ser Ala
            755                 760                 765
Glu Val Glu Tyr Val Asp Ser Gly Phe Pro Thr Arg Arg Phe Pro
    770                 775                 780
Ser Leu Arg Lys Leu Asn Ile Arg Glu Phe Asp Asn Leu Lys Gly Leu
785                 790                 795                 800
Leu Lys Lys Glu Gly Glu Gln Cys Pro Val Leu Glu Glu Ile Glu
            805                 810                 815
Ile Lys Cys Cys Pro Met Phe Val Ile Pro Thr Leu Ser Ser Val Lys
            820                 825                 830
Lys Leu Val Val Ser Gly Asp Lys Ser Asp Ala Ile Gly Phe Ser Ser
            835                 840                 845
Ile Ser Asn Leu Met Ala Leu Thr Ser Leu Gln Ile Arg Tyr Asn Lys
    850                 855                 860
Glu Asp Ala Ser Leu Pro Glu Glu Met Phe Lys Ser Leu Ala Asn Leu
865                 870                 875                 880
Lys Tyr Leu Asn Ile Ser Phe Tyr Phe Asn Leu Lys Glu Leu Pro Thr
            885                 890                 895
Ser Leu Ala Ser Leu Asn Ala Leu Lys His Leu Glu Ile His Ser Cys
```

-continued

```
                900             905             910
Tyr Ala Leu Glu Ser Leu Pro Glu Glu Gly Val Lys Gly Leu Ile Ser
        915             920             925

Leu Thr Gln Leu Ser Ile Thr Tyr Cys Glu Met Leu Gln Cys Leu Pro
    930             935             940

Glu Gly Leu Gln His Leu Thr Ala Leu Thr Asn Leu Ser Val Glu Phe
945             950             955             960

Cys Pro Thr Leu Ala Lys Arg Cys Glu Lys Gly Ile Gly Glu Asp Trp
            965             970             975

Tyr Lys Ile Ala His Ile Pro Arg Val Phe Ile Tyr
            980             985
```

SOLANUM BULBOCASTANUM LATE BLIGHT RESISTANCE GENE AND USE THEREOF

CROSS-REFERENCE TO RELATED APPLICATIONS

This application claims the benefit of U.S. Provisional Application No. 60/407,100, filed Aug. 29, 2002. The disclosure of said provisional application is incorporated herein by reference in its entirety.

BACKGROUND OF THE INVENTION

1. Field of the Invention

The present invention is directed to pathogen resistance in plants. More particularly, the invention is directed to identification and use of a gene that provides resistance to late blight disease. Even more particularly, the invention is directed to a *Solanum bulbocastanum* late blight resistance gene, nucleic acid molecules encoding polypeptides which confer resistance to late blight, and methods of using the gene, including expression in plant cells to confer or enhance a plant's resistance to late blight.

2. Description of the Art

On a worldwide basis, late blight, caused by the fungus *Phytophthora infestans*, is the most important of potato diseases. Worldwide losses due to potato late blight are estimated to be about $3 billion annually. Conservatively, *P. infestans* costs the potato industry in the United States $200 to $400 million annually.

Currently, late blight is controlled by application of fungicides. The cost of chemical control in the U.S., now applied in essentially all potato producing regions, is approximately $100–$200 per acre. Given that approximately 1.2 million acres are planted to potatoes annually in the U.S., the control costs alone are significant. In addition, in many years storage losses due to this pathogen are in the same range as the cost of control.

In the U.S., the recent migration from Mexico of highly aggressive and virulent new forms of *P. infestans* poses a serious threat to all potato producing regions. In particular, the presence of A2 mating type and fungicide resistant forms in field populations of the fungus limits producers' options in control practices.

*P. infestans* also causes late blight in other crops, including tomato, eggplant, and other solanaceous species. The new, aggressive strains of *P. infestans* also represent a serious threat to commercial tomato production.

Identification of a late blight resistance gene and development of transgenic plants resistant to *P. infestans*, is important goal in plant research to reduce crop losses and to reduce the need for fungicide application and costs of chemical control.

A wide variety of genetic loci that confer resistance to pathogens have been identified in plant species. These resistance loci often encode dominant resistance genes, or R genes. The R genes confer either vertical race-specific or horizontal nonspecific resistance to a pathogen (Plank, 1968). Vertical resistance is based upon an induced hypersensitive response in which the pathogen infection is contained by localized host cell death at infection sites. The mechanism for vertical resistance has been proposed to involve activation of the cell death response when a specific plant receptor (the R gene product) interacts with an elicitor produced by a corresponding Avr gene in the invading pathogen (Flor, 1971). Pathogen races are defined by distinct Avr gene profiles and resistance results from the interaction between specific R gene and Avr gene products (the gene for gene interaction).

In contrast to vertical resistance, horizontal resistance generally involves multiple plant genes and provides a general, stable, pathogen resistance in a race-nonspecific manner. Horizontal resistance is not correlated with the hypersensitive response, involving instead limiting pathogen spread in the host. *Solanum bulbocastanum* contains a dominant R gene locus which confers horizontal resistance to *P. infestans* when introgressed into the cultivated potato (Naess et al., 2000; Naess et al., 2001).

Map-based cloning has been employed to identify a variety of R genes from crop plants (Ballvora et al., 2002; Brueggeman et al., 2002; Dixon et al., 1996; Feuillet et al., 1997; Lagudah et al., 1997; Ori et al., 1997; Yoshimura et al., 1998).

SUMMARY OF THE INVENTION

We have now isolated a gene from the wild potato species *Solanum bulbocastanum* which confers horizontal resistance to *Phytophthora infestans*, the fungal pathogen that causes late blight disease. cDNA and genomic DNA sequences of the *Solanum bulbocastanum* late blight resistance gene, hereinafter denoted as Sbu1l, are specifically exemplified herein (SEQ ID NO:1 and 3, respectively). The deduced amino acid sequence is shown in SEQ ID NO:2 and 4. The resistance protein is in the class of Nucleotide Binding Site-Leucine-Rich Repeat Proteins (NBS-LRRP), and the gene in *S. bulbocastanum* is flanked by related NBS-LRRP gene sequences.

DNA encoding the resistance protein has been introduced into potato plants and confers resistance to *P. infestans*. A comparison of the deduced amino acid sequence of Sbu1l, which confers late blight resistance in transgenic plants, and the deduced amino acid sequence encoded by the *S. bulbocastanum* gene denoted herein as Sbu2l, which does not confer resistance, reveals 101 differences between the two proteins over 989 residues, or 90% identity. A comparison of the nucleic acid sequences of Sbu1l and Sbu2l reveals 221 differences between the two genes over 3174 bp of coding sequence, or 93% identity.

Accordingly, the invention is directed to nucleic acid molecules encoding a pathogen resistance gene, the gene being characterized in that it encodes the amino acid sequence shown in SEQ ID NO:4, or an amino acid sequence showing greater than about 90% sequence identity with SEQ ID NO:4 and which encodes a polypeptide having ability to confer or enhance a plant's resistance to late blight. Exemplary nucleic acid molecules include the exemplified cDNA and genomic DNA sequences and nucleic acid sequences having greater than about 93% sequence identity with the coding domain of the exemplified sequences and which confer or enhance a plant's resistance to late blight.

The invention is also directed to recombinant nucleic acid molecules containing the sequences encoding the polypeptides which confer late blight resistance, including, for example, recombinant vectors, such as cloning, expression or transformation vectors.

Another aspect of the invention is the provision of cells which are transformed by the vectors or DNA sequences of the invention.

Methods of using the sequences are also encompassed by the invention. A particular use of the invention is the provision of plants or plant cells transformed with one or more nucleic acid sequences encoding a polypeptide which confers late blight resistance to provide plants having resistance to *P. infestans*, or to provide plants having enhanced resistance to *P. infestans* or related plant pathogens. Such plants include, for example, solanaceous plants. Prominent food crops are in the Solanaceae family. These include potato (*Solanum tuberosum*); tomato (*Lysopersicon*, e.g., *L. lycopersicum* and *L. esculentum*); pepper (*Capsicum*); eggplant (*Solanum melongena*). Most preferably, in the practice of the invention, the solanaceous plant is potato.

As described below, the locus containing the resistance gene was characterized by map-based cloning and chromosome walking using a *S. bulbocastanum* Bacterial Artificial Chromosome (BAC) library. The actual resistance gene was isolated using Polymerase Chain Reaction (PCR) as the allele of the locus which contains the gene was not represented in the library. Chimeric transgenes constructed with Sbul1 transcribed from a potato ubiquitin (Ubi3) promoter were introduced into a susceptible potato variety. Greenhouse tests confirmed that transgenic potato clones containing these transgenes are resistant to late blight.

Accordingly, it is an object of the invention to provide nucleic acid sequences encoding polypeptides that confer late blight resistance; isolated polypeptides having this activity; recombinant nucleic acid molecules including expression vectors encoding the polypeptides; and cells harboring the recombinant nucleic acid molecules or expression vectors.

It is also an object of the invention to provide transformation vectors comprising a recombinant molecule, which vectors are effective for stably introducing the recombinant molecule into a plant.

It is also an object of the invention to provide methods of producing and using polypeptides conferring late blight resistance.

It is another object of the invention to provide transgenic plants having resistance to late blight or related pathogen, wherein the resistance is a result of expression of a recombinant nucleic acid molecule of the invention. An important aspect is the conferral of horizontal resistance to late blight, thereby providing general rather than race-specific control of the pathogen.

A further aspect of the invention is the provision of oligonucleotide probes capable of detecting a late blight resistance gene or functional equivalents thereof and the use of the probes to isolate nucleic acid sequences encoding a late blight resistance polypeptide or functional equivalent thereof.

A major impact of this invention on agriculture will be in controlling *P. infestans* in potatoes. The introduction of the resistance gene into cultivated potatoes would be expected to significantly reduce costs of chemical control, as well as providing a novel method for controlling fungicide resistant pathogen populations.

An additional application of this invention is controlling late blight in other solanaceous plants, for example, tomato production. The new, aggressive strains of *P. infestans* also represent a serious threat to commercial tomato production. Introduction of this resistance gene into tomato will result in significant savings in chemical control of the pathogen in this commodity.

Other objects and advantages of the invention will become readily apparent from the ensuing description.

BRIEF DESCRIPTION OF THE DRAWINGS

FIG. 4 shows the structure of the Sbul1 transgenes. Sbul1 genomic (SEQ ID NO:3) and cDNA (SEQ ID NO:1) sequences were fused to promoter and terminator sequences from the potato Ubi3 gene (Garbarino et al., 1994a; Garbarino et al., 1994b).

FIG. 6 shows a comparison of the deduced amino acid sequences of Sbul1 (SEQ ID NO:4), which confers late blight resistance in transgenic plants, and Sbul2 (SEQ ID NO:6) which does not. Comparison reveals 101 differences between the two proteins over 989 residues, or 90% identity.

FIG. 7 shows a comparison of the nucleic acid sequences of Sbul (SEQ ID NO:4), which confers late blight resistance in transgenic plants, and Sbul2 (SEQ ID NO:6) which does not. Comparison reveals 221 differences between the two genes over 3174 bp of coding sequence, or 93% identity.

BRIEF DESCRIPTION OF THE SEQUENCES

Figure 1:
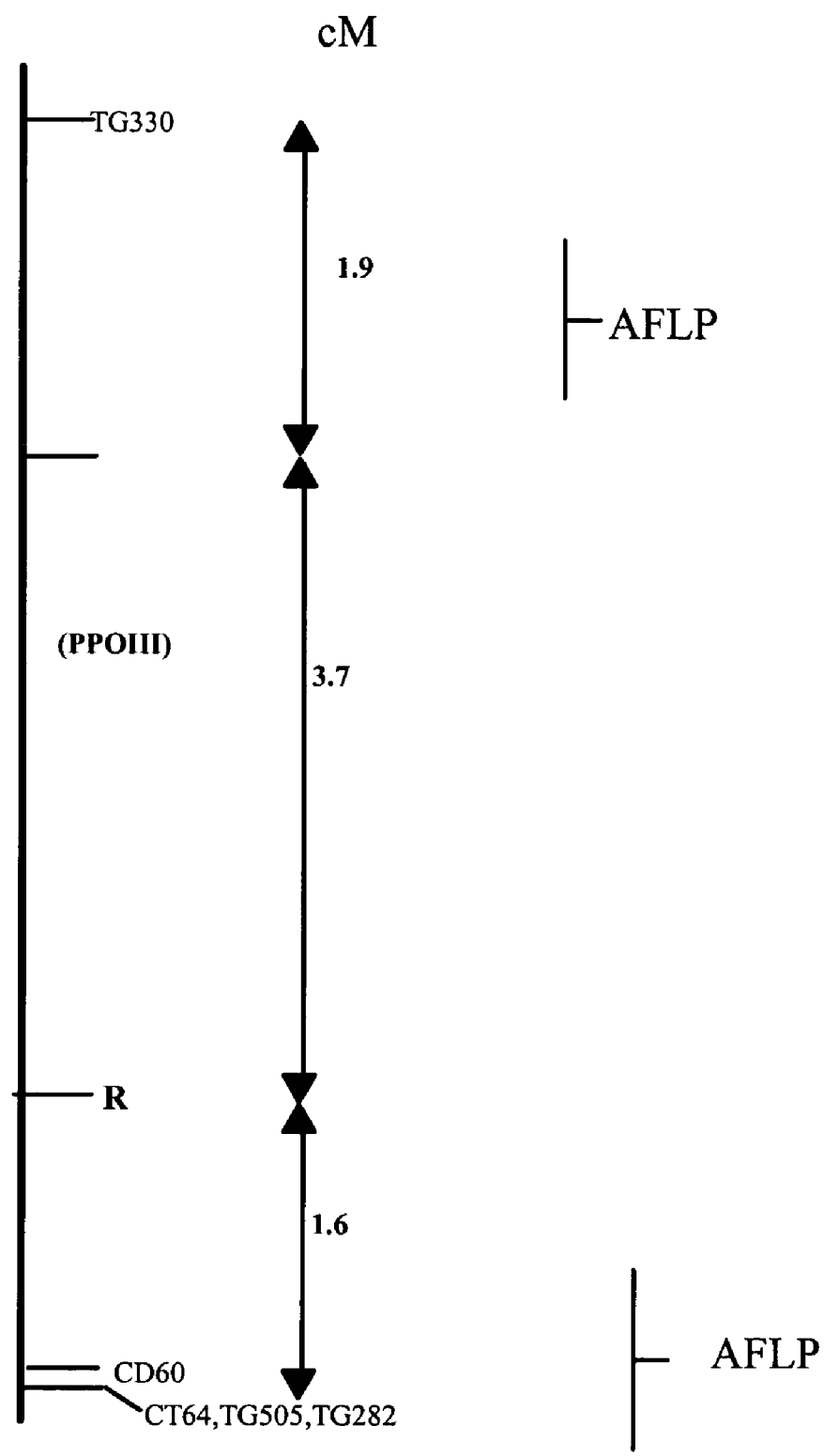
FIG. 1 shows the genetic map of the *S. bulbocastanum* late blight resistance gene locus. The approximate position of the locus is indicated by R. The positions of several RFLP markers relative to this locus are indicated. The relative positions of AFLP markers flanking the R gene are indicated.

SEQ ID NO:1 shows the cDNA sequence of the *Solanum bulbocastanum* late blight resistance gene Sbul1. Sequence feature information: *Solanum bulbocastanum* Sbul1 cDNA sequence: nucleotide 1 to 3193; coding region: nucleotide 52 to 3018; translation initiation codon: nucleotide 52 to 54; translation termination codon: nucleotide 3016 to 3018.

SEQ ID NO:2 shows the amino acid sequence encoded by SEQ ID NO:1.

SEQ ID NO:3 shows the DNA sequence of the active Sbul1 gene, a PCR product using template DNA from a late blight-resistant back cross 3 potato line containing *S. bulbocastanum* DNA. The sequence contains a 412 bp intron. Sequence feature information: *Solanum bulbocastanum* genomic Sbul1 sequence: nucleotide 1 to 3595; coding region: first coding domain: nucleotide 57 to 487; second coding domain: nucleotide 900 to 3435, wherein the 5' end of the second domain is linked to the 3' end of the first domain; intron: nucleotide 488 to 899; translation initiation codon: nucleotide 57 to 59; translation termination codon: nucleotide 3433 to 3435.

SEQ ID NO:4 shows the amino acid sequence encoded by SEQ ID NO:3.

SEQ ID NO:5 shows the DNA sequence of the Sbul2 gene. Sequence feature information: *Solanum bulbocastanum* genomic Sbul2 sequence: nucleotide 1 to 3347; coding region: first coding domain: nucleotide 57 to 509; second coding domain: nucleotide 789 to 3347, wherein the 5' end of the second domain is linked to the 3' end of the first domain; intron: nucleotide 510 to 788; translation initiation codon: nucleotide 57 to 59; translation termination codon: nucleotide 3345 to 3347.

SEQ ID NO:6 shows the amino acid sequence encoded by SEQ ID NO:5.

SEQ ID NO:7 shows the DNA sequence of the Sbul3 gene. Sequence feature information: *Solanum bulbocastanum* genomic Sbul3 sequence: nucleotide 1 to 3222; coding region: first coding domain: nucleotide 58 to 528; second coding domain: nucleotide 691 to 3222, wherein the 5' end of the second domain is linked to the 3' end of the first domain; intron: nucleotide 529 to 690; translation initiation codon: nucleotide 58 to 60; translation termination codon: nucleotide 3220 to 3222.

SEQ ID NO:8 shows the amino acid sequence encoded by SEQ ID NO:7.

SEQ ID NO:9 shows the sequence of the chimeric Ubi3/Sbul1 genomic transgene. Sequence feature information: Ubi3-*Solanum bulbocastanum* genomic Sbul1-Ubi3 sequence: nucleotide 1 to 5028; Potato Ubi3 promoter: nucleotide 1 to 953; *Solanum bulbocastanum* genomic Sbul1 gene: nucleotide 973 to 4566; coding region: first coding domain: nucleotide 1029 to 1459; second coding domain: nucleotide 1872 to 4407, wherein the 5' end of the second domain is linked to the 3' end of the first domain; intron: nucleotide 1460 to 1871; translation initiation codon: nucleotide 1029 to 1031; translation termination codon: nucleotide 4405 to 4407.

SEQ ID NO:10 shows the amino acid sequence encoded by SEQ ID NO:9.

Definitions

Unless defined otherwise, all technical and scientific terms used herein have the meaning commonly understood by a person skilled in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., Rieger, R., et al. (eds.), Springer Verlag (1991); and Hale & Marham, THE HARPER COLLINS DICTIONARY OF BIOLOGY (1991). References providing standard molecular biological procedures include Sambrook et al. (1989) *Molecular Cloning*, second edition, Cold Spring Harbor Laboratory, Plainview, N.Y.; *DNA Cloning*, Vols. I and II, IRL Press, Oxford, UK; and Hames and Higgins (eds.) (1985) *Nucleic Acid Hybridization*, IRL Press, Oxford, UK. References related to the manipulation and transformation of plant tissue include Kung and Arntzen (eds.) (1989) *Plant Biotechnology*, Butterworths, Stoneham, Mass.; R. A. Dixon (ed.) (1985) *Plant Cell Culture: A Practical Approach*, IRL Press, Oxford, UK; Schuler and Zielinski (1989) *Methods in Plant Molecular Biology*, Academic Press, San Diego, Calif.; Weissbach and Weissbach (eds.) (1988) Academic Press, San Diego, Calif.; I. Potrykus (1991) *Ann. Rev. Plant Physiol. Plant Mol. Biol.* 42:205; Weising et al. (1988) *Annu. Rev. Genet.* 22:421; van Wordragen et al. (1992) *Plant Mol. Biol. Rep.* 19:12; Davey et al. (1989) *Plant Mol. Biol.* 13:273; Walden and Schell (1990) *Eur. J. Biochem.* 192:563; Joersbo and Brunstedt (1991) *Physiol. Plant.* 81:256 and references cited in those references. The references cited in the list of References attached below also provides a description of the terms used herein. The following U.S. patents are incorporated herein by reference: U.S. Pat. Nos. 5,589,339; 6,084,156; 6,225,527; 6,287,865; 6225,532; 6,287,865; 6,100,449; and published application PCT/US00/23802 (WO 01/16353). All references cited in the present application are expressly incorporated by reference herein.

DETAILED DESCRIPTION OF THE INVENTION

We have now cloned a horizontal late blight resistance gene from *S. bulbocastanum*. As described below, the resistance gene Sbu11 was isolated by map-based cloning. In this technique the locus that confers resistance is mapped relative to amplified fragment length polymorphism (AFLP) and restriction fragment length polymorphism (RFLP) markers that are linked to the resistance gene. Four markers that appeared to be most closely linked to the resistance gene were used to probe a *S. bulbocastanum* genomic bacterial artificial chromosome (BAC) library and hybridizing BAC clones identified. The resistance locus was obtained by chromosome walking from an original anchor clone. The resistance gene was identified by introduction of candidate genes from the locus into transgenic potato and screening for late blight resistance.

The present invention is directed to isolated nucleic acid sequences derived from a *S. bulbocastanum* gene which encode polypeptides which confer horizontal late blight resistance. The specifically exemplified nucleic acid sequences include the Sbu11 cDNA sequence (SEQ ID NO:1) and the DNA sequence of the active Sbu11 gene, a PCR product using template DNA from a late blight-resistant back cross 3 potato line containing *S. bulbocastanum* DNA (SEQ ID NO:3). The latter sequence contains a 412 bp intron. SEQ ID NO:4 shows the deduced amino acid sequence of the Sbu11 gene product. The invention encompasses nucleic acid sequences which have greater than about 93% sequence identity with the coding domain of the exemplified sequences and encode a polypeptide which confers or enhances a plant's resistance to late blight. More preferably, the nucleic acid sequences have about 95% sequence identity with the coding domain of the exemplified sequences and encode a polypeptide which confers or enhances a plant's resistance to late blight. For purposes of the present invention, the degree of identity between two nucleic acid sequences is determined by any method know in the art, for example by the Clustal method (Thompson et al. 1994), using ClustalW 1.7 or 1.8. Further, nucleic acid sequences which hybridize under high stringency conditions with the coding region of the DNA sequence of SEQ ID NO:1 or 3 and which encode a polypeptide having the activity defined above, are also encompassed by the present invention.

The invention is directed to nucleic acid molecules encoding the amino acid sequence of SEQ ID NO:4, or an amino acid sequence showing greater than about 90% sequence identity with SEQ ID NO:4 and which encodes a polypeptide having ability to confer or enhance a plant's resistance to late blight. More preferably, the encoded amino acid sequence has at least about 95%, and most preferably at least about 97% sequence identity with SEQ ID NO:4 and has the activity defined above. For purposes of the present invention, the degree of identity between two amino acids is determined by any method known in the art, for example, by the FASTA/FASTP method of Pearson (1990), using ALIGN, with the BLOSUM50 or PAM250 scoring matrix.

Preferably, the polypeptides of the present invention comprise an amino acid sequence of SEQ ID NO:4 or an amino acid sequence showing greater than about 90% sequence identity with SEQ ID NO:4 and which encodes a polypeptide having ability to confer or enhance a plant's resistance to late blight.

The degeneracy of the genetic code is well known to the art; therefore, synonymous coding sequences with one or more codon substitutions can be readily determined by one of ordinary skill in the art. Synonymous coding sequences vary from the exemplified coding sequences but encode proteins of the same amino acid sequences as those specifically provided herein. Examples of conservative substitutions are within the groups of basic amino acids (such as arginine, lysine and histidine), acidic amino acids (such as glutamic acid and aspartic acid), polar amino acids (such as glutamine and asparagine), hydrophobic amino acids (such as leucine isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art as described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The present invention also relates to recombinant expression vectors comprising a nucleic acid sequence of the present invention, a promoter, and transcriptional and translational stop signals.

The present invention also relates to recombinant host cells, comprising a nucleic acid sequence of the invention, which are advantageously used in the recombinant production of the polypeptides. Preparation of transformed host cells and cloning methods are described by U.S. Pat. No. 5,374,540, which is incorporated herein by reference.

Preparation of Transgenic Plants: The transgenic plant or plant cell expressing an RNA transcript or polypeptide of the present invention may be constructed in accordance with methods known in the art. In brief, the plant or plant cell is constructed by incorporating one or more expression constructs encoding a polypeptide of the present invention into the plant host genome and propagating the resulting modified plant or plant cell into a transgenic plant or plant cell.

As discussed above, a particular use of the invention is the provision of plants or plant cells transformed with a DNA sequence encoding an amino acid sequence which confers resistance to late blight or related pathogens.

Another use of the invention is as probes and primers capable of detecting a late blight resistance gene or functional equivalent thereof in fungi of the genus *Phytophthora*. Using the nucleic acid sequences of the invention facilitates the isolation of homologous genes from hosts to obtain genes which protect host cells, including fungi and plants against other fungal pathogens.

EXAMPLES

The following examples are intended only to further illustrate the invention and are not intended to limit the scope of the invention.

Map-Based Cloning of the *S. bulbocastanum* Late Blight Resistance Gene (Sbul1)

*S. bulbocastanum* DNA was introgressed into potato by somatic fusion at the University of Wisconsin (Naess et al., 2001). Fertile progeny were then back crossed to potato. The position of the *S. bulbocastanum* late blight resistance gene locus was mapped using a back-cross 3 population segregating for *P. infestans* resistance using a combination of AFLP (Vos et al., 1995) and RFLP techniques. The late blight resistance locus maps to chromosome 8 (Naess et al., 2001). The segregating population was subjected to AFLP mapping, exhaustion of the commercially available primer/enzyme sets resulted in identification of over 400 polymorphic bands. RFLP mapping was also employed, the population was screened with a variety of chromosome 8 markers. The relative positions of the AFLP and RFLP markers closest to the Sbul1 locus are shown in FIG. 1. The clustering of these markers, together with the failure of AFLP to generate a marker within the flanking RFLP probes (CD60 and TG261) suggested that the resistance locus is located in an area of chromosome 8 with high rates of recombination resulting in very different genetic and physical maps. This interpretation suggested that additional mapping was unnecessary, and four RFLP markers (TG282, TG505, CD60, PPOIII) were selected to probe a *S. bulbocastanum* BAC library (Song et al., 2000).

Identification of Candidate Sbul1 genes.

Figure 2:
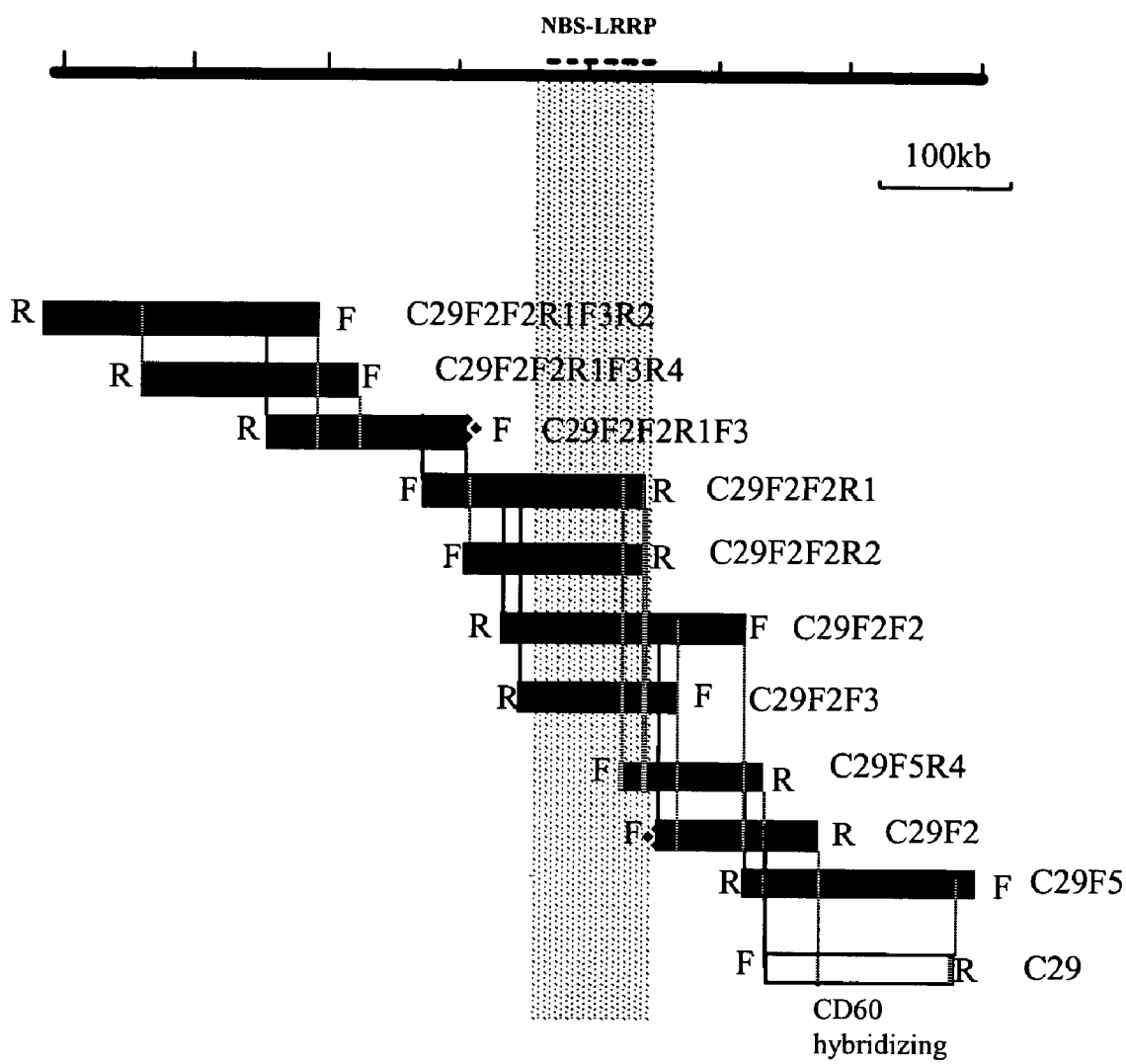
FIG. 2 shows the assembly of an approximately 600 kb contig on *S. bulbocastanum* anchored by a BAC clone hybridizing to the RFLP marker CD60. BAC C29 was cloned by hybridization of filters to the labeled RFLP marker. BAC end-sequence analysis allowed design of specific primer pairs for both ends of the insert (F and R indicate forward and reverse). For each walk subsets of the BAC library were pooled and screened by PCR using these specific primers. BAC end-sequence analysis also revealed the position of members of a family of nucleotide binding site-leucine-rich repeat proteins (NBS-LRRP) indicated.

BAC clones corresponding to each of the four RFLP markers were isolated and used to anchor PCR-based chromosome walking (FIG. 1). BAC end-sequences were used to generate specific primer pairs for screening of pooled BAC clones by PCR (Cai et al., 1995). The assembly of an approximately 600 kb contig proximal to the CD60 RFLP marker on *S. bulbocastanum* chromosome 8 is shown in FIG. 2. Computational (BLAST) alignment of the end sequences of BAC isolates C29F2F2R1 and C29F2F2R2 with the available database (Altschul et al., 1990) indicated the presence of sequences encoding nucleotide binding site-leucine-rich repeat proteins (NBS-LRRPs) similar to previously identified R genes (Ballvora et al., 2002; Lagudah et al., 1997; Simons et al., 1998; Yoshimura et al., 1998). Primers specific to the NBS-LRRP locus on the contig in FIG. 2 were employed in PCR screening of genomic DNA from the original population segregating for late blight resistance, and this locus was found to be linked to the resistance phenotype.

Figure 3:
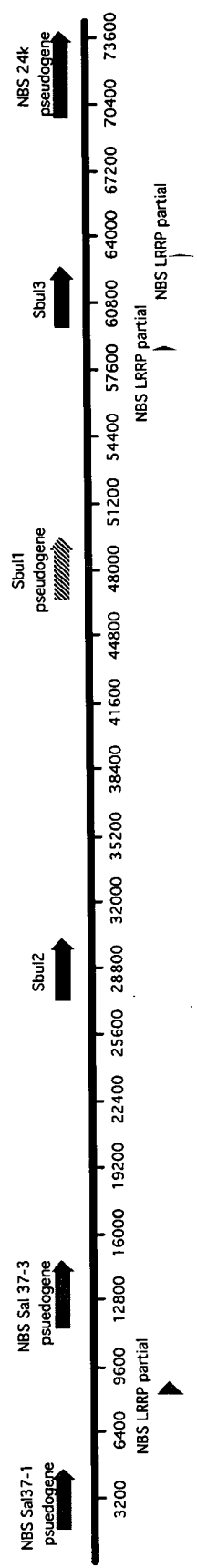
FIG. 3 shows the structure of the *S. bulbocastanum* chromosome 8 NBS-LRRP domain linked to late blight resistance. The domain contains six complete and three partial NBS-LRRP coding sequences. Only two of the six complete genes on the BAC contig, Sbul2 and Sbul3, were found to encode uninterrupted open reading frames. The remaining four NBS-LRRP genes are interrupted by frame shift mutations (NBS Sal 37-1 and Sbul1) or stop codons (NBS Sal 37-3 and NBS 24K).
Figure 5:
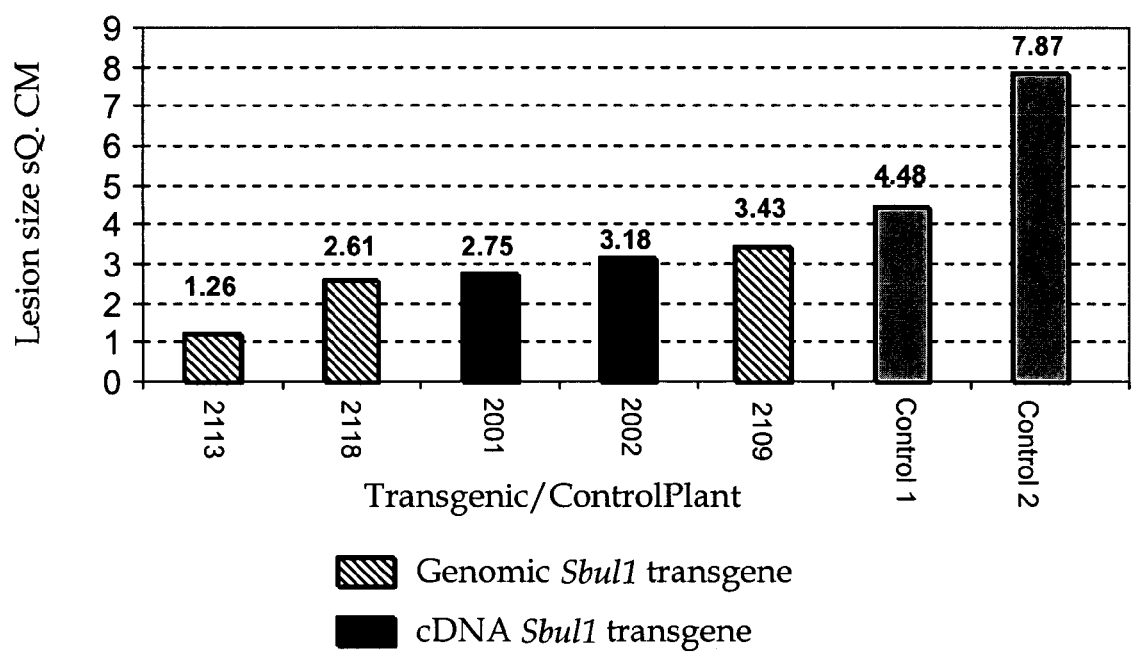
FIG. 5 shows transgenic potatoes expressing Sbul1 genomic and cDNA transgenes have improved resistance to *P. infestans* US8. Detached leaves of greenhouse-grown transgenic and control plants were inoculated with *P. infestans* and incubated for four days. Lesion size determined computationally (Bioquant Systems).
Figure 8:
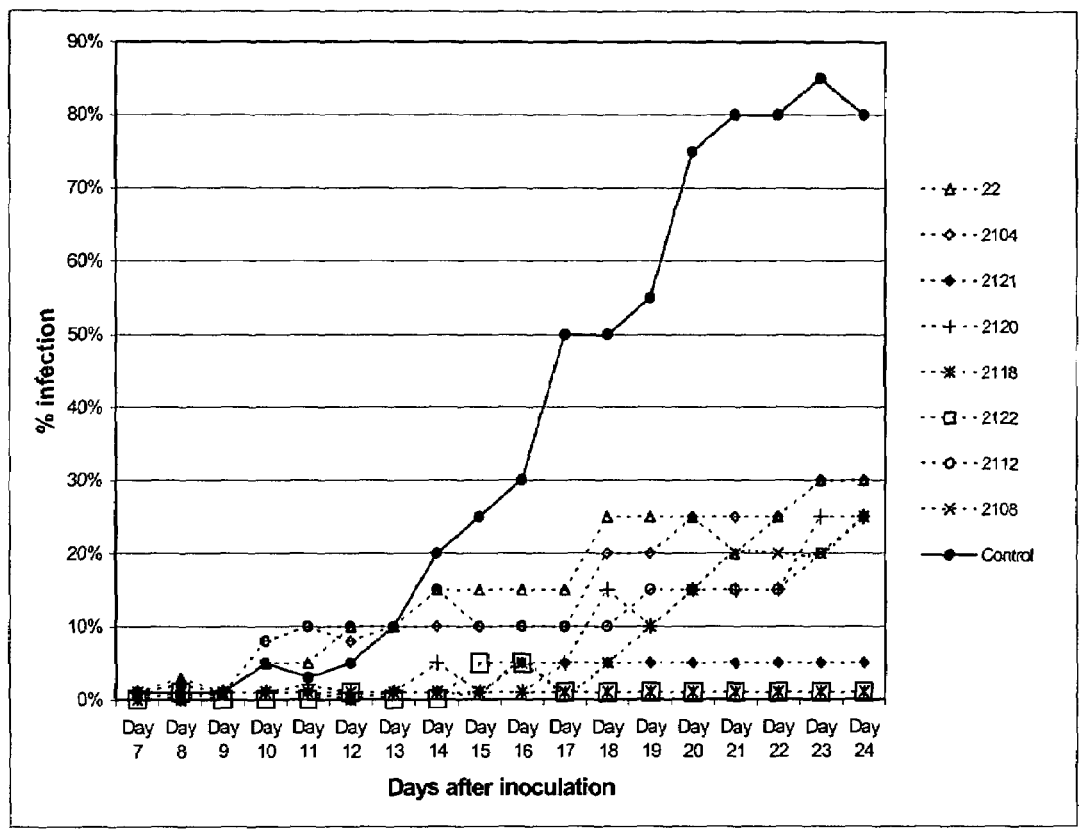
FIG. 8 shows potato lines transformed with the Sbul1 genomic transgene have enhanced resistance to *P. infestans* US8 in intact plant assays.

An approximately 75 kb region containing six complete NBS-LRRP genes was characterized. As shown in FIG. 3, four of the six complete genes were found to represent pseudogenes, with coding sequences interrupted by either frame shift mutations or stop codons. These data suggested that late blight resistance at this locus was associated with Sbul2 and/or Sbul3 expression.

Identification of the Sbul1 Late Blight Resistance Gene.

Experiments to determine the efficacy of either Sbul2 or Sbul3 (FIG. 3) in conferring late blight resistance were based on mobilization of these genes plus at least 3 kb of 5' and 3' flanking sequence into susceptible potatoes by *Agrobacterium*-mediated transformation. Sbul2 or Sbul3 and flanking sequences were mobilized into a binary transformation vector pCGN1547 (McBride et al., 1990). These binary vector constructs were used to introduce the Sbul2 or Sbul3 genes into potato varieties Lenape (Akeley et al., 1968) and Atlantic (Webb et al., 1978) by a standard transformation/selection protocol (Snyder et al., 1993). Transgenic potato plants containing either the Sbul2 or Sbul3 genes were screened for resistance to late blight by detached leaf assay (Trognitz et al., 1995). Neither the Sbul2 or Sbul3 genes conferred resistance to *P. infestans*.

The similarity of the NBS-LRRPs on the *S. bulbocastanum* contig (FIG. 3) to known disease resistance genes is significant. A BLAST database search (Altschul et al., 1990) using the deduced amino acid sequence of Sbul2 returns seven putative resistance genes from *Arabidopsis* at the highest identity ($P(N)<10^{-120}$) followed by the I2 *Fusarium oxysporum* resistance gene from tomato (Simons et al., 1998) ($P(N)<10^{-108}$). In addition, this PCR probes from this locus indicate linkage to the resistance gene in the segregating population. It therefore appeared possible that one or more of the four pseudogenes present on the *S. bulbocastanum* contig (FIG. 3) represented an inactive allele of a gene active on the other chromosome of this diploid species. Specific primers were prepared to the Sbul1, Sbul2, and Sbul3 genes on the locus, and RACE (Rapid Amplification of cDNA Ends)-PCR was employed to amplify potential mRNAs from $polyA^+$ RNA prepared from *P. infestans*-infected *S. bulbocastanum* leaves. Messenger RNA products corresponding to Sbul1, Sbul2 and Sbul3 were amplified. This suggested that active Sbul1 was heterozygous in *S. bulbocastanum*, with one allele active and the other interrupted by a frame shift mutation (Helgeson et al., 1988). PCR amplification of Sbul1 using genomic DNA from a late blight-resistant BC3 line as a template generated an amplified product encoding a mRNA essentially identical to the Sbul1 cDNA (SEQ ID NO:3).

The DNA sequence of the active Sbul1 cDNA is shown in SEQ ID NO:1. The deduced amino acid sequence is shown in SEQ ID NO:2. The DNA sequence of active Sbul1 gene, a PCR product from *S. bulbocastanum*-containing potato genomic DNA, containing a 412 bp intron is shown in SEQ ID NO:3. The deduced amino acid sequence of the Sbul1 gene product is shown in SEQ ID NO:4. The DNA sequence of the Sbul2 gene is shown in SEQ ID NO:5, and the deduced Sbul2 amino acid sequence is shown in SEQ ID NO:6. The DNA sequence of the Sbul3 gene is shown in SEQ ID NO:7, and the deduced Sbul3 amino acid sequence is shown in SEQ ID NO:8.

Expression of Sbul1 in Transgenic Plants

In order to express Sbul1 in transgenic plants two chimeric transgenes were constructed. Transcription of the Sbul1 gene is directed from the potato Ubi3 promoter, which will result in constitutive moderate-level expression (Garbarino et al., 1994 a; Garbarino et al., 1994b). The Ubi3 polyadenylation signal was fused to the 3' end of each sequence (FIG. 4).

The sequence of the genomic chimeric transgene is shown in SEQ ID NO:9. The transgenes shown in FIG. 4 were mobilized into the binary transformation vector pBINPLUS-ARS. This vector is a version of the pBINPLUS vector (Van Engelen et al., 1995) modified in our laboratory by replacement of selectable marker transcriptional control sequences (CaMV35S promoter, NOS terminator) with a promoter and terminator derived from the potato Ubi3 gene (Garbarino et al., 1994a). These binary vector constructs were used to introduce the transgenes into potato varieties Lenape (Akeley et al., 1968) and Atlantic (Webb et al., 1978) by a standard transformation/selection protocol (Snyder et al., 1993). Transgenic potato plants were screened for resistance to late blight by detached leaf assay (Trognitz et al., 1995).

Greenhouse Assay of Late Blight Resistance of Transgenic Potatoes Expressing Sbul1 Transgenes To assay for late blight resistance fully developed leaves from greenhouse-grown plants were detached. Inocula were obtained from two-week-old cultures of *P. infestans* (strain US8, Florida isolate) grown on rye agar. Inoculations were made by placing a 10 ul droplet of a sporangial suspension ($4\times10^4$ ml) that had been incubated at 8° C. for 2.5 hours (to liberate zoospores) on both sides of the midrib of the abaxial surface. The inoculated leaflets were placed in petri dishes containing moistened filter paper to maintain 100% relative humidity. Inoculated material was incubated for 1 day at 15° C. in darkness, then for four days at 15° C., 16-hour/day photoperiod (400 $E^{-m-2}S^{-1}$). A computer-driven image analysis system (Bioquant IV, R and M Biometrics, Nashville, Tenn.) was used to obtain measurements of lesions. The lesion diameter was determined by projecting the whole leaves onto a grid lining the Bioquant Digitizing Pad. The digitizing pad was coupled with an IBM PC and measurements were generated using Bioquant Systems software.

As shown in FIG. 5, both the Sbul1 genomic and cDNA transgenes conferred resistance to *P. infestans* in transgenic potatoes. As shown in FIG. 6, the deduced amino acid sequence of the Sbul2 gene, which does not confer resistance, has 90% identity to the Sbul1 deduced amino acid sequence. As shown in FIG. 7, the nucleic acid sequences of the Sbul1 and Sbul2 coding domains are 93% identical.

The data presented in FIG. 5 shows that Sbul1, when introduced into susceptible potato varieties, is capable of conferring resistance to late blight. While the Sbul2 and Sbul3 genes do not, individually, confer a resistant phenotype, this does not preclude a role for these gene products in enhancing Sbul1-mediated resistance originating from this locus.

Whole-Plant Glasshouse Test of Late Blight Resistance of Potato Plants Transformed with Sbul1.

To assay for late blight resistance, transgenic and control tubers were planted in 6 inch pots and grown 16 hr light and 8 hr dark photoperiod using high pressure sodium lamps as supplemental lighting. Transgenic lines used in these experiments contained the genomic Sbul1 transgene (SEQ ID NO:9). Inocula were obtained from cultures of *P. infestans* (strain MD-02-pet-1 an A2, US-8 genotype) grown in lima bean media in the dark at room temperature. After two weeks of incubation, the plates were flooded 2× with sterile water and scraped lightly using an L-shaped glass or plastic rod to collect sporangia. The liquid from the plates were filtered into a 1 liter glass beaker using two layers of cheesecloth. The total volume was roughly estimated and sporangia was counted using a hemacytometer. Using sterile water, the volume of the inoculum was adjusted that gave a final count of 5,000 sporangia/ml. The inoculum was transferred into a sprayer (approximately 2 ml/sec) and incubated at 4° C. for 1 hour followed by room temperature incubation for 30 minutes.

The whole-plant glasshouse test described by Stewart et al. (1983) was used to determine which of the plants were resistant to *P. infestans*. Plants of each clone in flower bud were inoculated with *P. infestans*. Each plant was scored daily using Malcolmson's scoring scale of increasing resistance (Cruickshank et al., 1982) starting 7 days after inoculation, and plants of each clone compared. As shown in FIG.

8, two of the transgenic lines exhibited no infection 24 days after inoculation, six additional transgenic lines had intermediate levels of resistance.

Description of Plasmids

The plasmid pBT1596 consists of the Sbu11 genomic transgene shown in SEQ ID NO:9 inserted into the multiple cloning site of the binary transformation vector pBINPLUS-ARS. The plasmid pBT1593 consists of the Sbu11 cDNA sequence (SEQ ID NO:1) inserted between the potato Ubi3 promoter and terminator sequences indicated in SEQ ID NO:9 in the multiple cloning site of the binary transformation vector pBINPLUS-ARS.

Statement of Deposit

The plasmids were introduced into the host *Escherichia coli* DH5α and the transformed *Escherichia coli* strains were deposited Aug. 18, 2003 under terms of the Budapest Treaty with Agricultural Research Service Culture Collection (NRRL) National Center for Agricultural Utilization Research, Agricultural Research Service, U.S. Department of Agriculture, 1815 North University Street, Peoria, Ill. 61604 USA and given the following accession numbers:

| Plasmid | Accession No. | SEQ ID NO |
|---------|---------------|-----------|
| pBT1596 | NRRL B-30685  | SEQ ID NO:9 |
| pBT1593 | NRRL B-30686  | SEQ ID NO:1 |

It is understood that the foregoing detailed description is given merely by way of illustration and that modification and variations may be made within, without departing from the spirit and scope of the invention. All publications, patents, and patent applications cited herein are hereby incorporated by reference in their entirety.

REFERENCES

Akeley, R. V., Mills, W. R., Cunningham, C. E., and Watts, J. 1968. Lenape: a new potato variety high in solids and chipping quality. *American Potato Journal* 45: 142–151.

Altschul, S. F., Gish, W., Miller, W., Myers, E. W., and Lipman, D. J. 1990. Basic local alignment search tool. *Journal of Molecular Biology* 215: 403–410.

Ballvora, A., Ercolano, M. R., Weiss, J., Meksem, K., Bormann, C. A., Oberhagemann, P., Salamini, F., and Gebhardt, C. 2002. The R1 gene for potato resistance to late blight (Phytophthora infestans) belongs to the leucine zipper/NBS/LRR class of plant resistance genes. *Plant J* 30: 361–371.

Brueggeman, R., Rostoks, N., Kudrna, D., Kilian, A., Han, F., Chen, J., Druka, A., Steffenson, B., and Kleinhofs, A. 2002. The barley stem rust-resistance gene Rpg1 is a novel disease-resistance gene with homology to receptor kinases. *Proc Natl Acad Sci USA* 99: 9328–9333.

Cai, L., Taylor, J. F., Wing, R. A., Gallagher, D. S., Woo, S. S., and Davis, S. K. 1995. Construction and characterization of a bovine bacterial artificial chromosome library. *Genomics* 29: 413–425.

Cruickshank, G., Stewart, H. E., Wastie, R. L. 1982. An illustrated assessment key for foliage blight of potatoes. *Potato Research* 25, 213–214.

Dixon, M. S., Jones, D. A., Keddie, J. S., Thomas, C. M., Harrison, K., and Jones, J. D. 1996. The tomato Cf-2 disease resistance locus comprises two functional genes encoding leucine-rich repeat proteins. *Cell* 84: 451–459.

Feuillet, C., Schachermayr, G., and Keller, B. 1997. Molecular cloning of a new receptor-like kinase gene encoded at the Lr10 disease resistance locus of wheat. *Plant J* 11: 45–52.

Flor, H. H. 1971. Current status of the gene-for-gene concept. *Annual Reviews of Phytopathology* 9: 275–296.

Garbarino, J. E., and Belknap, W. R. 1994a. Isolation of a ubiquitin-ribosomal protein gene (ubi3) from potato and expression of its promoter in transgenic plants. *Plant Mol Biol* 24: 119–127.

Garbarino, J. E., and Belknap, W. R. 1994b. Use of ubiquitin promoters for transgene expression in potato. In W. D. Park [ed.], Molecular and Cellular Biology of the Potato, Second Edition, 173–185. CAB International, Wallingford, UK.

Helgeson, J. P., Pohlman, J. D., Austin, S., Haberlach, G. T., Wielgus, S. M., Ronis, D., Zambolim, L., Tooley, P., McGrath, J. M., James, R. V., and Stevenson, W. R. 1988. Somatic hybrids between Solanum bulbocastanum and potato: a new source of resistance to late blight. *Theor Appl Genet* 96: 738–742.

Lagudah, E. S., Moullet, O., and Appels, R. 1997. Map-based cloning of a gene sequence encoding a nucleotide-binding domain and a leucine-rich region at the Cre3 nematode resistance locus of wheat. *Genome* 40: 659–665.

McBride, K. E., and Summerfelt, K. R. 1990. Improved binary vectors for *Agrobacterium*-mediated plant transformation. *Plant Mol Biol* 14: 269–276.

Naess, S. K., Bradeen, J. M., Wielgus, S. M., Haberlach, G. T., McGrath, J. M., and Helgeson, J. P. 2000. Resistance to late blight in Solanum bulbocastanum is mapped to Chromosome 8. *Theo Appl Genet* 101.

Naess, S. K., Bradeen, J. M., Wielgus, S. M., Haberlach, G. T., McGrath, J. M., and Helgeson, J. P. 2001. Analysis of the introgression of Solanum bulbocastanum DNA into potato breeding lines. *Mol Genet Genomics* 265: 694–704.

Ori, N., Eshed, Y., Paran, I., Presting, G., Aviv, D., Tanksley, S., Zamir, D., and Fluhr, R. 1997. The I2C family from the wilt disease resistance locus I2 belongs to the nucleotide binding, leucine-rich repeat superfamily of plant resistance genes. *Plant Cell* 9: 521–532.

Pearson, W. R. 1990. Rapid and sensitive sequence comparison with FASTP and FASTA. *Methods Enzymology* 183:63–98.

Plank, J. E. v.d. 1968. *Disease resistance in plants*. Academic, New York.

Simons, G., Groenendijk, J., Wijbrandi, J., Reijans, M., Groenen, J., Diergaarde, P., Van der Lee, T., Bleeker, M., Onstenk, J., de Both, M., Haring, M., Mes, J., Cornelissen, B., Zabeau, M., and Vos, P. 1998. Dissection of the fusarium I2 gene cluster in tomato reveals six homologs and one active gene copy. *Plant Cell* 10: 1055–1068.

Snyder, G. W., and Belknap, W. R. 1993. A modified method for routine *Agrobacterium*-mediated transformation of in vitro grown potato microtubers. *Plant Cell Reports* 12: 324–327.

Song, J., Dong, F., and Jiang, J. 2000. Construction of a bacterial artificial chromosome (BAC) library for potato molecular cytogenetics research. *Genome* 43: 199–204.

Stewart, H. E., Flavelle, P. H., McCalmont, D. C., Wastie, R. L. 1983. Correlation between glasshouse and field tests for resistance to foliage blight caused by Phytophthora infestans. *Potato Research* 26, 41.

Thompson, J. D., Higgins, D. G., and Gibson, T. J. 1994. CLUSTAL W: improving the sensitivity of progressive multiple sequence alignment through sequence weighting, positions-specific gap penalties and weight matrix choice. *Nucl Acids Res* 22: 4673-4680.

Trognitz, B. R., Chacón, G., Pinedo, H., and M., E. 1995. Screening for R genes causing race-specific resistance to late blight in wild potato species. *Am Potato J* 72: 662-670.

van Engelen, F. A., Molthoff, J. W., Conner, A. J., Nap, J. P., Pereira, A., and Stiekema, W. J. 1995. pBINPLUS —an Improved Plant Transformation Vector Based On pBIN19. *Transgenic Research* 4: 288-290.

Vos, P., Hogers, R., Bleeker, M., Reijans, M., van de Lee, T., Homes, M., Frijters, A., Pot, J., Peleman, J., and Kuiper, M. 1995. AFLP: a new technique for DNA fingerprinting. *Nucleic Acids Res* 23: 4407-4414.

Webb, R. E., Wilson, D. R., Shumaker, J. R., Graves, B., Henninger, M. R., Watts, J., Frank, J. A., and Murphy, H. J. 1978. "Atlantic": A new potato variety with high solids, good processing quality, and resistance to pests. *Amer Potato J* 55: 141-146.

Yoshimura, S., Yamanouchi, U., Katayose, Y., Toki, S., Wang, Z. X., Kono, I., Kurata, N., Yano, M., Iwata, N., and Sasaki, T. 1998. Expression of Xa1, a bacterial blight-resistance gene in rice, is induced by bacterial inoculation. *Proc Natl Acad Sci USA* 95: 1663-1668.

What is claimed is:

1. An isolated nucleic acid molecule encoding a plant disease resistance polypeptide, wherein the nucleic acid molecule is selected from the group consisting of:
   (a) a nucleic acid molecule with the polypeptide coding sequence of SEQ ID NO: 1 from nucleotide 52 to nucleotide 3018.
   (b) a nucleic acid molecule which encodes SEQ ID NO:2, SEQ ID NO:4 or SEQ ID NO:10.
   (c) the nucleic acid molecule of SEQ ID NO:1, SEQ ID NO: 3 or SEQ ID NO: 9.

2. The nucleic acid molecule of claim 1 which is contained in plasmid pBT1596 or plasmid pBT1593.

3. A nucleic acid construct comprising the isolated nucleic acid molecule of SEQ ID NO:1 or SEQ ID NO:3 operably linked to one or more control sequences.

4. An isolated host cell transformed with the isolated nucleic acid molecule of claim 1.

5. A plant transfomied with the isolated nucleic acid molecule of claim 1.

6. A transgenic seed of the plant according to claim 5.

7. The plant of claim 5, wherein the plant is a solanaceous plant.

8. The plant of claim 7, wherein the solanaceous plant is potato.

9. A transgenic progeny of the plant of claim 5.

10. A method of conferring or enhancing resistance in a plant, plant part or plant cell to a fungal pathogen, which comprises transforming the plant, plant part, or plant cell, with one or more of the isolated nucleic acid molecule of claim 1.

11. The method of claim 10, wherein the plant is a solanaceous plant.

12. The method of claim 11, wherein the solanaceous plant is potato.

13. The method of claim 10, wherein said resistance is to late blight disease, caused by the fungus *Phylophthora infestans*.

14. A method for producing a plant disease resistance polypeptide, which comprises cultivating the host cell of claim 4 under conditions suitable for production of the polypeptide; and recovering the polypeptide.

* * * * *